(12) United States Patent
Hubschwerlen et al.

(10) Patent No.: US 8,039,466 B2
(45) Date of Patent: Oct. 18, 2011

(54) 5-HYDROXYMETHYL-OXAZOLIDIN-2-ONE ANTIBACTERIALS

(75) Inventors: Christian Hubschwerlen, Durmenach (FR); Philippe Panchaud, Allschwil (CH); Jean-Luc Specklin, Kembs (FR)

(73) Assignee: Actelion Pharmaceutical Ltd., Allschwil (CH)

( * ) Notice: Subject to any disclaimer, the term of this patent is extended or adjusted under 35 U.S.C. 154(b) by 255 days.

(21) Appl. No.: 12/516,335

(22) PCT Filed: Nov. 23, 2007

(86) PCT No.: PCT/IB2007/054759
§ 371 (c)(1),
(2), (4) Date: May 26, 2009

(87) PCT Pub. No.: WO2008/062379
PCT Pub. Date: May 29, 2008

(65) Prior Publication Data
US 2010/0069376 A1 Mar. 18, 2010

(30) Foreign Application Priority Data
Nov. 24, 2006 (WO) .................. PCT/IB2006/054429

(51) Int. Cl.
C07D 498/14 (2006.01)
C07D 401/12 (2006.01)
A61K 31/5383 (2006.01)
(52) U.S. Cl. ...................................... 514/229.5; 544/99
(58) Field of Classification Search ............... 544/99; 514/229.5
See application file for complete search history.

(56) References Cited

U.S. PATENT DOCUMENTS

| | | | |
|---|---|---|---|
| 4,806,541 A | 2/1989 | Jolidon et al. | |
| 4,946,847 A | 8/1990 | Jolidon et al. | |
| 4,977,265 A | 12/1990 | Jolidon et al. | |
| 5,646,163 A * | 7/1997 | Demuth et al. | 514/312 |
| 2009/0247578 A1 | 10/2009 | Hubschwerlen et al. | |

FOREIGN PATENT DOCUMENTS

| | | |
|---|---|---|
| EP | 0 216 345 | 4/1987 |
| JP | 04 128288 | 4/1992 |
| WO | WO 03/031443 | 4/2003 |
| WO | WO 03/032962 | 4/2003 |
| WO | WO 2004/096221 | 11/2004 |
| WO | WO 2005/023801 | 3/2005 |
| WO | WO 2005/058888 | 6/2005 |
| WO | WO 2007/017828 | 2/2007 |
| WO | WO 2007017828 A2 * | 2/2007 |

OTHER PUBLICATIONS

Benz in Comprehensive Organic Synthesis, 8.M. Trost, I. Fleming, Eds, Pergamon Press: New York, vol. 6, pp. 381-481, (1991).

Del Valle et al., Journal of Organic Chemistry, vol. 68, pp. 3923-3931, (2003).
Gennaro, A., Index from "Remington: The Science and Practice of Pharmacy", 20th Edition, Philadelphia College of Pharmacy and Science, (2001).
Gibson, M., Index from "Pharmaceutical Preformulation and Formulation", IHS Health Group, Englewood, GO, USA, ISBN: 1574911201, (2001).
Gillard et al., Journal of Organic Chemistry, vol. 61, pp. 2226-2231, (1996).
Gould, P., "Salt Selction for Basic Drugs", International Journal of Pharmaceutics, vol. 33, pp. 201-217, Mar. 24, 1986.
Hamilton-Miller, Journal of Antimicrobial Chemotherapy, vol. 33, pp. 197-200, (1994).
Hubschwerlen et al., Bioorganic & Medicinal Chemistry Letters, vol. 13, pp. 4229-4233, Jul. 2003.
Hubschwerlen et al., Bioorganic & Medicinal Chemistry, vol. 11, pp. 2313-2319, Jan. 2003.
Knights, Journal of the American Chemical Society, vol. 90, p. 5281, Aug. 1968.
Kocienski, Protecting Groups, Foundations of Organic Chemistry Series—Thieme, (1994).
Mitsunobu, Synthesis—Reviews, vol. 1, pp. 1-28, Jan. 1981.
Sharpless et al., Journal of Organic Chemistry, vol. 57, No. 10, 2768, (1992).
International Search Report for International Application No. PCT/IB2006/052714, mailed Apr. 12, 2007.
Written Opinion for International Application No. PCT/IB2006/052714, mailed Apr. 12, 2007.

(Continued)

Primary Examiner — Kahsay T Habte
(74) Attorney, Agent, or Firm — Hunton & Williams LLP

(57) ABSTRACT

The invention relates to novel chimeric antibiotics of formula I

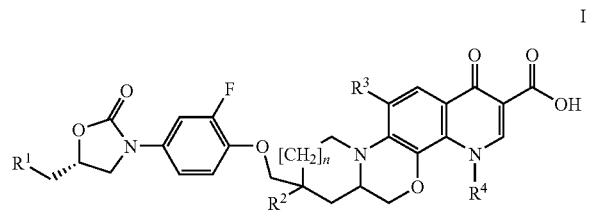

wherein
$R^1$ represents OH, $OPO_3H_2$ or $OCOR^5$;
$R^2$ represents H, OH or $OPO_3H_2$;
$R^3$ represents H or halogen;
$R^4$ is H, $(C_1\text{-}C_3)$alkyl, or cycloalkyl;
$R^5$ represents piperidin-4-yl or $R^5$ is the residue of a naturally occurring amino acid, of the enantiomer of a naturally occurring amino acid or of dimethylaminoglycine;
n is 0 or 1;
and to salts (in particular pharmaceutically acceptable salts) of compounds of formula I.
These chimeric compounds are useful in the manufacture of medicaments for the treatment of infections (e.g. bacterial infections).

18 Claims, No Drawings

OTHER PUBLICATIONS

International Preliminary Report on Patentability Opinion for International Application No. PCT/IB2006/052714, mailed Feb. 12, 2008.
Non-Final Office Action in U.S. Appl. No. 12/063,305, mailed May 20, 2011.
Response to Office Action in U.S. Appl. No. 12/063,305, filed Aug. 22, 2011.
Bennis et al., "Synthesis from lactose of new enantiomerically pure polyhydroxylated pyrrolidines with branched structures," Carbohydrate Research 279: 307-314 (1995).
Coates et al., "New Therapeutic Agents of the Quinoline Series. Part VI: Quinolyl-thiazoles, -amidines, and -pyrroles," J. Chem. Soc. Abstracts, pp. 419-420 (1943).
Fetter et al., "Simple and Condensed γ-Lactams. Part 23 Synthesis of Some Compounds related to the Monobactams, carrying Non-acylamino substituents in Position 3 and Various Heterocyclyl or Heterocyclylmethyl Substituents in Position 4 of the β-Lactam Ring," J. Chem. Research, Synopses 11: 444-445 (1995).
Frølund et al., "Novel Class of Potent 4-Arylalkyl Substituted 3-Isoxazolol $GABA_A$ Antagonists: Synthesis, Pharmacology, and Molecular Modeling," J. Med. Chem. 45: 2454-68 (2002).
Hearas et al., "A New Class of Fused Imidazoles by Intramolecular Nucleophilic ipso-Substitution in 2-Alkysulfonylimidazoles: Synthesis of 2,3-Dihydroimidazo[2,1- b][1,3]oxazoles," Synthesis 9: 1613-1624 (1999).

Iwai and Nakamura, "Compounds. SLIV. Synthesis of 3-Aminoisoxazoles and 3-Hydroxyisoxazoles (3-Isoxazolones)," Chem. Pharm. Bull., vol. 14, No. 11, pp. 1277-1286 (1966).
Larock, Comprehensive Organic Transformations, $2^{nd}$ Ed., Wiley-VCH, pp. 1932-1940 (1999).
Mäntylä et al., "Synthesis, in Vitro Evaluation, and Antileishmanial Activity of Water-soluble Prodrugs of Buparvaquone," J. Med. Chem. 47: 188-195 (2004).
Mihina and Herbst, "The Reaction of Nitriles with Hydrazoic Acid: Synthesis of Monosubstituted Tetrazoles," J. Org. Chem. 15: 1082-92 (1950).
Narukawa et al., "General and Efficient Synthesis of 2-Alkylcarbapenems: Synthesis of Dethiacarba Analogs of Clinically Useful Carbapenems via Palladium-Catalyzed Cross-Coupling Reaction," Tetrahedron 53(2): 539-556 (1997).
Reck et al., "Identification of 4-Substituted 1,2,3-Triazoles as Novel Oxazolidinone Antibaterial Agents with Reduced Activity against monoamine Oxidase A," J. Med. Chem. 48: 499-506 (2005).
Wikler et al., "Methods for Dilution Antimicrobial Susceptibility Tests for Bacteria that Grow Aerobically; Approved Standard—Seventh Edition," vol. 26, No. 2 (2006).

* cited by examiner

5-HYDROXYMETHYL-OXAZOLIDIN-2-ONE ANTIBACTERIALS

The present invention concerns novel chimeric antibiotics that are obtained from oxazolidinone derivatives linked to a quinolone via a spacer, pharmaceutical antibacterial compositions containing them and use thereof in the manufacture of a medicament for the treatment of infections (e.g. bacterial infections). These chimeric compounds are useful antimicrobial agents effective against a variety of human and veterinary pathogens including among others Gram-positive aerobic bacteria, Gram-negative bacteria, anaerobic organisms and acid-fast organisms.

The intensive use of antibiotics has exerted a selective evolutionary pressure on microorganisms to produce genetically based resistance mechanisms. Modern medicine and socio-economic behaviour exacerbate the problem of resistance development by creating slow growth situations for pathogenic microbes, e.g. in artificial joints, and by supporting long-term host reservoirs, e.g. in immuno-compromised patients.

In hospital settings, an increasing number of strains of *Staphylococcus aureus, Streptococcus pneumonia, Enterococcus* spp., and *Pseudomonas aeruginosa*, major sources of infections, are becoming multi-drug resistant and therefore difficult if not impossible to treat:

S. *aureus* is β-lactam, quinolone and now even vancomycin resistant;

S. *pneumoniae* is becoming resistant to penicillin, quinolone and even to new macrolides;

*Enteroccocci* are quinolone and vancomycin resistant and β-lactams were never efficacious against these strains.

Further new emerging organisms like *Acinetobacter* spp. or *C. difficile*, which have been selected during therapy with the currently used antibiotics, are becoming a real problem in hospital settings.

In addition, microorganisms that are causing persistent infections are increasingly being recognized as causative agents or cofactors of severe chronic diseases like peptic ulcers or heart diseases.

In a chimeric molecule two or more molecules that exist separately in their native state are joined together to form a single entity (i.e. molecule) having the desired functionality of all of its constituent molecules.

Molecules wherein two antibiotics that have two different modes of action have been linked have been reported in the literature (e.g. *Journal of Antimicrobial Chemotherapy* (1994), 33, 197-200). Many of them are however such that the two antibiotic parts are released after biological activation (e.g. central ester cleavage, beta-lactam cleavage). Chemically and biochemically stable chimeric molecules that bind, as such, in two different targets have been more seldom reported. For example, oxazolidinone-quinolone hybrids have been reported as useful antimicrobial agents effective against a variety of multi-drug resistant pathogens (WO 03/032962, WO 03/031443 and WO 2004/096221, WO 2005/023801 and WO 2005/058888). Further, synthesis and biological evaluation of these hybrids (*Bioorg. & Med. Chem.* (2003), 11, 2313-2319) and the influence of the central spacer on the antibacterial activity in the structure-activity relationship in the oxazolidinone-quinolone series have also been reported (*Bioorg. Med. Chem. Lett.* (2003), 13, 4229-4233). All these derivatives contain a 4-aminomethyl-oxazolidinone rest as part of the oxazolidinone pharmacophore.

It has now been surprisingly found that the chimeric derivatives of formula I as defined hereafter are useful antimicrobial agents that show effective against a variety of multi-drug resistant bacteria.

Thus, the present invention relates to compounds of formula I

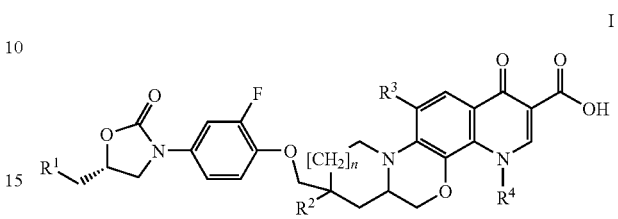

wherein
$R^1$ represents OH, $OPO_3H_2$ or $OCOR^5$;
$R^2$ represents H, OH or $OPO_3H_2$;
$R^3$ represents H or halogen;
$R^4$ represents H, $(C_1-C_3)$alkyl or cycloalkyl;
$R^5$ represents piperidin-4-yl or $R^5$ is the residue of a naturally occurring amino acid, of the enantiomer of a naturally occurring amino acid or of dimethylaminoglycine; and
n is 0 or 1;
and to salts (in particular pharmaceutically acceptable salts) of compounds of formula I.

The compounds of formula I may contain one or more stereogenic or asymmetric centers, such as one or more asymmetric carbon atoms. The compounds of formula I may thus be present as mixtures of stereoisomers or preferably as pure stereoisomers. Mixtures of stereoisomers may be separated in a manner known to a person skilled in the art.

The following paragraphs provide definitions of the various chemical moieties for the compounds according to the invention and are intended to apply uniformly throughout the specification and claims unless an otherwise expressly set out definition provides a broader or narrower definition.

Unless specified otherwise, the term "alkyl" (whether used alone or in combination) refers to a saturated straight or branched chain alkyl group containing 1 to 6 carbon atoms, and preferably 1 to 3 carbon atoms. Representative examples of alkyl groups include, but are not limited to, methyl, ethyl, propyl, iso-propyl, butyl, iso-butyl, sec-butyl, tert-butyl, n-pentyl, neopentyl, iso-pentyl, n-hexyl and iso-hexyl. The term "$(C_1-C_x)$alkyl" (x being an integer) refers to a saturated straight or branched chain alkyl group containing 1 to x carbon atoms.

The term "halogen" refers to fluorine, chlorine, bromine or iodine, and preferably to fluorine or chlorine.

The term "cycloalkyl", used alone or in combination, refers to a saturated cyclic hydrocarbon moiety containing 3 to 5 carbon atoms. Representative examples of cycloalkyl groups include, but are not limited to, cyclopropyl and cyclopentyl.

The term "tri-$(C_1-C_5)$alkylsilyl" refers to a silyl group wherein each of the three hydrogen atoms of the silyl group have been replaced by a $(C_1-C_5)$alkyl group, whereby the $(C_1-C_5)$alkyl groups may be the same or different. Representative examples of tri-$(C_1-C_5)$alkylsilyl groups include, but are not limited to, trimethylsilyl and tert-butyldimethylsilyl.

The term "diphenyl-$(C_1-C_5)$alkylsilyl" refers to a silyl group wherein two of the three hydrogen atoms of the silyl group have been replaced by phenyl groups and the third hydrogen atom of the silyl group has been replaced by a ($C_1$-$C_5$)alkyl group. An example of diphenyl-($C_1$-$C_5$)alkylsilyl group is tert-butyldiphenylsilyl.

When it is written that $R^5$ is the residue of an amino acid, it is meant thereby that $R^5$—COOH is the corresponding amino acid.

The term "pharmaceutically acceptable salts" refers to non-toxic, inorganic or organic acid and/or base addition salts. Reference can be made to "Salt selection for basic drugs", *Int. J. Pharm.* (1986), 33, 201-217.

Unless used regarding temperatures, the term "about" placed before a numerical value "X" refers in the current application to an interval extending from X minus 10% of X to X plus 10% of X, and preferably to an interval extending from X minus 5% of X to X plus 5% of X. In the particular case of temperatures, the term "about" placed before a temperature "Y" refers in the current application to an interval extending from the temperature Y minus 10° C. to Y plus 10° C., and preferably to an interval extending from Y minus 5° C. to Y plus 5° C.; besides, room temperature shall mean in the current patent application 25° C.

In particular, the invention relates to compounds of formula I that are also compounds of formula $I_{CE}$

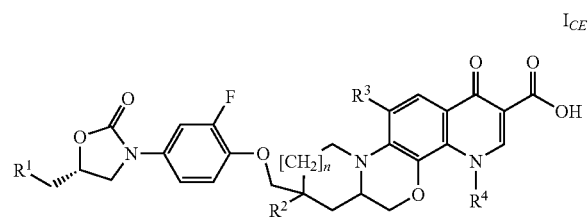

wherein
$R^1$ represents OH, $OPO_3H_2$ or $OCOR^5$;
$R^2$ represents H, OH or $OPO_3H_2$;
$R^3$ represents halogen (especially fluorine);
$R^4$ represents H, ($C_1$-$C_3$)alkyl or cycloalkyl;
$R^5$ represents piperidin-4-yl or $R^5$ is the residue of a naturally occurring amino acid or of the enantiomer of a naturally occurring amino acid (in particular the residue of D-Ala or L-Ala); and
n is 0 or 1;
and to salts (in particular pharmaceutically acceptable salts) of compounds of formula $I_{CE}$.

A particular embodiment of this invention relates to compounds of formula I that are also compounds of formula $I_P$

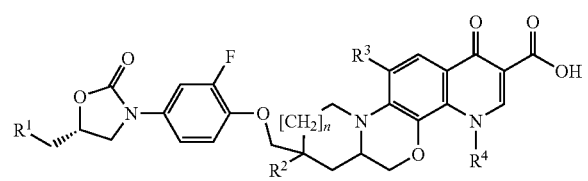

wherein
$R^1$ represents OH, $OPO_3H_2$ or $OCOR^5$;
$R^2$ represents H, OH or $OPO_3H_2$;
$R^3$ represents H or halogen;
$R^4$ represents H, ($C_1$-$C_3$)alkyl or cycloalkyl;
$R^5$ is the residue of a naturally occurring amino acid, of the enantiomer of a naturally occurring amino acid or of dimethylaminoglycine; and n is 0 or 1;
and to salts (in particular pharmaceutically acceptable salts) of compounds of formula $I_P$.

The compounds of formula $I_P$ will in particular be compounds of formula $I_{CEP}$,

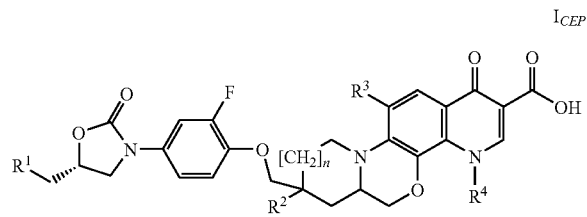

wherein
$R^1$ represents OH, $OPO_3H_2$ or $OCOR^5$;
$R^2$ represents H, OH or $OPO_3H_2$;
$R^3$ represents halogen (especially fluorine);
$R^4$ represents H, ($C_1$-$C_3$)alkyl or cycloalkyl;
$R^5$ is the residue of a naturally occurring amino acid or of the enantiomer of a naturally occurring amino acid (in particular the residue of D-Ala or L-Ala); and
n is 0 or 1.

According to a first main embodiment of this invention, the compounds of formula I or $I_P$ are such that n is 0. Such compounds will be hereafter referred to as "compounds of formula $I_5$".

According to a second main embodiment of this invention, the compounds of formula I or $I_P$ are such that n is 1. Such compounds will be hereafter referred to as "compounds of formula $I_6$".

According to one variant of the invention, the compounds of formula I or $I_P$ will be such that they have the following stereochemistry:

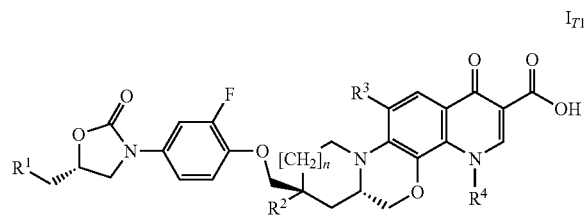

Compounds of formula $I_{T1}$ may be such that n is 0 (which compounds will be hereafter referred to as "compounds of formula $I_{5T1}$"), or may be such that n is 1 (which compounds will be hereafter referred to as "compounds of formula $I_{6T1}$").

According to another variant of the invention, the compounds of formula I will be such that they have the following stereochemistry:

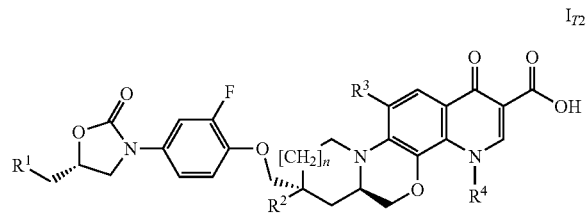

Compounds of formula $I_{T2}$ may be such that n is 0 (which compounds will be hereafter referred to as "compounds of formula $I_{5T2}$"), or may be such that n is 1 (which compounds will be hereafter referred to as "compounds of formula $I_{6T2}$").

According to yet another variant of the invention, the compounds of formula I or $I_P$ will be such that they have the following stereochemistry:

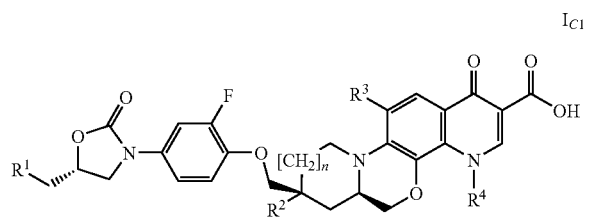

$I_{C1}$

Compounds of formula $I_{C1}$ may be such that n is 0 (which compounds will be hereafter referred to as "compounds of formula $I_{5C1}$"), or may be such that n is 1 (which compounds will be hereafter referred to as "compounds of formula $I_{6C1}$").

According to yet another variant of the invention, the compounds of formula I or $I_P$ will be such that they have the following stereochemistry:

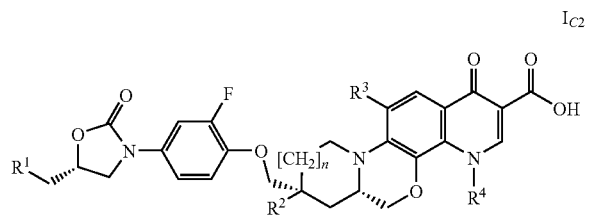

$I_{C2}$

Compounds of formula $I_{C2}$ may be such that n is 0 (which compounds will be hereafter referred to as "compounds of formula $I_{5C2}$"), or may be such that n is 1 (which compounds will be hereafter referred to as "compounds of formula $I_{6C2}$").

One main embodiment of this invention relates to the compounds of formula I that are also compounds of formula $I_D$

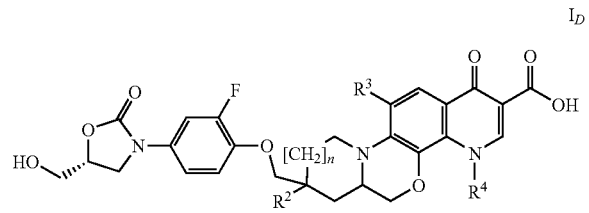

$I_D$ wherein
$R^2$ represents H or OH;
$R^3$ represents H or halogen;
$R^4$ represents H, $(C_1$-$C_3)$alkyl or cycloalkyl; and
n is 0 or 1;
and to salts (in particular pharmaceutically acceptable salts) of compounds of formula $I_D$.

Another main embodiment of this invention relates to the compounds of formula I that are also compounds of formula $I_{PDG}$

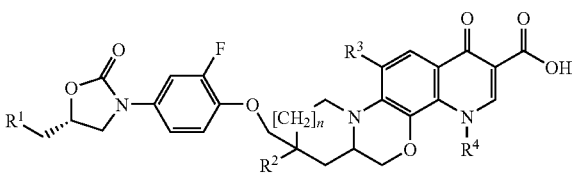

$I_{PDG}$ wherein
$R^1$ represents OH and $R^2$ represents $OPO_3H_2$, or $R^1$ represents $OPO_3H_2$ or $OCOR^5$ and
$R^2$ represents H, OH or $OPO_3H_2$;
$R^3$ represents H or halogen;
$R^4$ represents H, $(C_1$-$C_3)$alkyl or cycloalkyl;
$R^5$ represents piperidin-4-yl or $R^5$ is the residue of a naturally occurring amino acid, of the enantiomer of a naturally occurring amino acid or of dimethylaminoglycine; and
n is 0 or 1;
and to salts (in particular pharmaceutically acceptable salts) of compounds of formula $I_{PDG}$.

According to an important variant of this invention, the compounds of formula I or $I_P$ will be such that $R^1$ is OH.

According to another important variant of this invention, the compounds of formula I or $I_P$ will be such that $R^1$ is $OPO_3H_2$ or $OCOR^5$. One subvariant of said important variant relates to compounds of formula I wherein $R^1$ is $OPO_3H_2$. The other subvariant of said important variant relates to compounds of formula I wherein $R^1$ is $OCOR^5$; in this case, $R^5$ will preferably represent piperidin-4-yl 1 or be such that $R^5$—COOH represents L-Ala, and in particular represent piperidin-4-yl.

According to yet another important variant of this invention, the compounds of formula I or $I_P$ will be such that $R^2$ is H.

According to yet another important variant of this invention, the compounds of formula I or $I_P$ will be such that $R^2$ is OH.

According to a further important variant of this invention, the compounds of formula I or $I_P$ will be such that $R^2$ is $OPO_3H_2$.

Preferably, the amino acid residue $R^5$ is such that $R^5$—COOH represents a natural amino acid (notably L-Ala) or its enantiomer (notably D-Ala). More preferably, the amino acid residue $R^5$ is such that $R^5$—COOH represents a natural amino acid (notably L-Ala).

Preferred compounds of formula I are also those wherein at least one of the following characteristics is present:
  $R^1$ represents OH, $OPO_3H_2$ or $OCOR^5$ wherein $R^5$ is piperidin-4-yl;
  $R^2$ represents H or OH;
  $R^3$ represents halogen.

Preferred compounds of formula $I_P$ are also those wherein at least one of the following characteristics is present:
  $R^1$ represents OH or $OPO_3H_2$;
  $R^2$ represents H or OH;
  $R^3$ represents halogen.

More preferred compounds of formula I or $I_P$ are those wherein at least one of the following characteristics is present:
  n is 0;
  $R^1$ represents OH;
  $R^2$ represents H or OH;
  $R^3$ represents fluorine;
  $R^4$ represents $(C_1$-$C_3)$alkyl or cycloalkyl.

Even more preferred compounds of formula I or $I_P$ are those wherein at least one of the following characteristics is present:

n is 0;
$R^1$ represents OH;
$R^2$ represents H or OH (and notably OH);
$R^3$ represents fluorine;
$R^4$ represents cycloalkyl (and in particular cyclopropyl);
the compound of formula I is also a compound of formula $I_{T1}$ The following compounds of formula I are particularly preferred:

(13S,16S)-1-cyclopropyl-7-fluoro-16-[2-fluoro-4-((R)-5-hydroxymethyl-2-oxo-oxazolidin-3-yl)-phenoxymethyl]-16-hydroxy-4-oxo-1,4,13,15,16,17-hexahydro-12H-11-oxa-1,14-diaza-cyclopenta[a]phenanthrene-3-carboxylic acid;

(13S,16S)-16-{4-[(R)-5-((R)-2-amino-propionyloxymethyl)-2-oxo-oxazolidin-3-yl]-2-fluoro-phenoxymethyl}-1-cyclopropyl-7-fluoro-16-hydroxy-4-oxo-1,4,13,15,16,17-hexahydro-12H-11-oxa-1,14-diaza-cyclopenta[a]phenanthrene-3-carboxylic acid;

(13S,16S)-1-ethyl-7-fluoro-16-[2-fluoro-4-((R)-5-hydroxymethyl-2-oxo-oxazolidin-3-yl)-phenoxymethyl]-16-hydroxy-4-oxo-1,4,13,15,16,17-hexahydro-12H-11-oxa-1,14-diaza-cyclopenta[a]phenanthrene-3-carboxylic acid;

(13S,16R)-1-cyclopropyl-7-fluoro-16-[2-fluoro-4-((R)-5-hydroxymethyl-2-oxo-oxazolidin-3-yl)-phenoxymethyl]-4-oxo-1,4,13,15,16,17-hexahydro-12H-11-oxa-1,14-diaza-cyclopenta[a]phenanthrene-3-carboxylic acid;

(13S,16S)-1-cyclopropyl-7-fluoro-16-[2-fluoro-4-((R)-5-hydroxymethyl-2-oxo-oxazolidin-3-yl)-phenoxymethyl]-4-oxo-1,4,13,15,16,17-hexahydro-12H-11-oxa-1,14-diaza-cyclopenta[a]phenanthrene-3-carboxylic acid;

(6aS,8R)-4-cyclopropyl-11-fluoro-8-[2-fluoro-4-((R)-5-hydroxymethyl-2-oxo-oxazolidin-3-yl)-phenoxymethyl]-8-hydroxy-1-oxo-1,4,6,6a,7,8,9,10-octahydro-5-oxa-4,10a-diaza-chrysene-2-carboxylic acid;

(6aS,8S)-4-cyclopropyl-11-fluoro-8-[2-fluoro-4-((R)-5-hydroxymethyl-2-oxo-oxazolidin-3-yl)-phenoxymethyl]-8-hydroxy-1-oxo-1,4,6,6a,7,8,9,10-octahydro-5-oxa-4,10a-diaza-chrysene-2-carboxylic acid;

(6aR,8R)-4-cyclopropyl-11-fluoro-8-[2-fluoro-4-((R)-5-hydroxymethyl-2-oxo-oxazolidin-3-yl)-phenoxymethyl]-8-hydroxy-1-oxo-1,4,6,6a,7,8,9,10-octahydro-5-oxa-4,10a-diaza-chrysene-2-carboxylic acid;

(6aR,8S)-4-cyclopropyl-11-fluoro-8-[2-fluoro-4-((R)-5-hydroxymethyl-2-oxo-oxazolidin-3-yl)-phenoxymethyl]-8-hydroxy-1-oxo-1,4,6,6a,7,8,9,10-octahydro-5-oxa-4,10a-diaza-chrysene-2-carboxylic acid;

(13S,16S)-1-cyclopropyl-7-fluoro-16-[2-fluoro-4-((R)-5-hydroxymethyl-2-oxo-oxazolidin-3-yl)-phenoxymethyl]-4-oxo-16-phosphonooxy-1,4,13,15,16,17-hexahydro-12H-11-oxa-1,14-diaza-cyclopenta[a]phenanthrene-3-carboxylic acid;

(13S,16S)-7-fluoro-16-[2-fluoro-4-((R)-5-hydroxymethyl-2-oxo-oxazolidin-3-yl)-phenoxymethyl]-16-hydroxy-4-oxo-1,4,13,15,16,17-hexahydro-12H-11-oxa-1,14-diaza-cyclopenta[a]phenanthrene-3-carboxylic acid;

(13S,16S)-1-cyclopropyl-7-fluoro-16-[2-fluoro-4-((R)-2-oxo-5-phosphonooxymethyl-oxazolidin-3-yl)-phenoxymethyl]-4-oxo-16-phosphonooxy-1,4,13,15,16,17-hexahydro-12H-11-oxa-1,14-diaza-cyclopenta[a]phenanthrene-3-carboxylic acid;

(13S,16S)-1-cyclopropyl-7-fluoro-16-[2-fluoro-4-((R)-2-oxo-5-phosphonooxymethyl-oxazolidin-3-yl)-phenoxymethyl]-4-oxo-16-hydroxy-1,4,13,15,16,17-hexahydro-12H-11-oxa-1,14-diaza-cyclopenta[a]phenanthrene-3-carboxylic acid;

(13S,16S)-16-{4-[(R)-5-((S)-2-amino-propionyloxymethyl)-2-oxo-oxazolidin-3-yl]-2-fluoro-phenoxymethyl}-1-cyclopropyl-7-fluoro-16-hydroxy-4-oxo-1,4,13,15,16,17-hexahydro-12H-11-oxa-1,14-diaza-cyclopenta[a]phenanthrene-3-carboxylic acid;

(13S,16S)-1-cyclopropyl-7-fluoro-16-{2-fluoro-4-[(R)-2-oxo-5-(piperidine-4-carbonyloxymethyl)-oxazolidin-3-yl]-phenoxymethyl}-16-hydroxy-4-oxo-1,4,13,15,16,17-hexahydro-12H-11-oxa-1,14-diaza-cyclopenta[a]phenanthrene-3-carboxylic acid;

(13S,16S)-1-cyclopropyl-7-fluoro-16-[2-fluoro-4-((R)-2-oxo-5-phosphonooxymethyl-oxazolidin-3-yl)-phenoxymethyl]-16-hydroxy-4-oxo-1,4,13,15,16,17-hexahydro-12H-11-oxa-1,14-diaza-cyclopenta[a]phenanthrene-3-carboxylic acid;

as well as salts thereof (and in particular pharmaceutically acceptable salts thereof).

The following compounds of formula $I_P$ are particularly preferred:

(13S,16S)-1-cyclopropyl-7-fluoro-16-[2-fluoro-4-((R)-5-hydroxymethyl-2-oxo-oxazolidin-3-yl)-phenoxymethyl]-16-hydroxy-4-oxo-1,4,13,15,16,17-hexahydro-12H-11-oxa-1,14-diaza-cyclopenta[a]phenanthrene-3-carboxylic acid;

(13S,16S)-16-{4-[(R)-5-((R)-2-amino-propionyloxymethyl)-2-oxo-oxazolidin-3-yl]-2-fluoro-phenoxymethyl}-1-cyclopropyl-7-fluoro-16-hydroxy-4-oxo-1,4,13,15,16,17-hexahydro-12H-11-oxa-1,14-diaza-cyclopenta[a]phenanthrene-3-carboxylic acid;

(13S,16S)-1-ethyl-7-fluoro-16-[2-fluoro-4-((R)-5-hydroxymethyl-2-oxo-oxazolidin-3-yl)-phenoxymethyl]-16-hydroxy-4-oxo-1,4,13,15,16,17-hexahydro-12H-11-oxa-1,14-diaza-cyclopenta[a]phenanthrene-3-carboxylic acid;

(13S,16R)-1-cyclopropyl-7-fluoro-16-[2-fluoro-4-((R)-5-hydroxymethyl-2-oxo-oxazolidin-3-yl)-phenoxymethyl]-4-oxo-1,4,13,15,16,17-hexahydro-12H-11-oxa-1,14-diaza-cyclopenta[a]phenanthrene-3-carboxylic acid;

(13S,16S)-1-cyclopropyl-7-fluoro-16-[2-fluoro-4-((R)-5-hydroxymethyl-2-oxo-oxazolidin-3-yl)-phenoxymethyl]-4-oxo-1,4,13,15,16,17-hexahydro-12H-11-oxa-1,14-diaza-cyclopenta[a]phenanthrene-3-carboxylic acid;

(6aS,8R)-4-cyclopropyl-11-fluoro-8-[2-fluoro-4-((R)-5-hydroxymethyl-2-oxo-oxazolidin-3-yl)-phenoxymethyl]-8-hydroxy-1-oxo-1,4,6,6a,7,8,9,10-octahydro-5-oxa-4,10a-diaza-chrysene-2-carboxylic acid;

(6aS,8S)-4-cyclopropyl-11-fluoro-8-[2-fluoro-4-((R)-5-hydroxymethyl-2-oxo-oxazolidin-3-yl)-phenoxymethyl]-8-hydroxy-1-oxo-1,4,6,6a,7,8,9,10-octahydro-5-oxa-4,10a-diaza-chrysene-2-carboxylic acid;

(6aR,8R)-4-cyclopropyl-11-fluoro-8-[2-fluoro-4-((R)-5-hydroxymethyl-2-oxo-oxazolidin-3-yl)-phenoxymethyl]-8-hydroxy-1-oxo-1,4,6,6a,7,8,9,10-octahydro-5-oxa-4,10a-diaza-chrysene-2-carboxylic acid;

(6aR,8S)-4-cyclopropyl-11-fluoro-8-[2-fluoro-4-((R)-5-hydroxymethyl-2-oxo-oxazolidin-3-yl)-phenoxymethyl]-8-hydroxy-1-oxo-1,4,6,6a,7,8,9,10-octahydro-5-oxa-4,10a-diaza-chrysene-2-carboxylic acid;

(13S,16S)-1-cyclopropyl-7-fluoro-16-[2-fluoro-4-((R)-5-hydroxymethyl-2-oxo-oxazolidin-3-yl)-phenoxymethyl]-4-oxo-16-phosphonooxy-1,4,13,15,16,17-hexahydro-12H-11-oxa-1,14-diaza-cyclopenta[a]phenanthrene-3-carboxylic acid;

(13S,16S)-7-fluoro-16-[2-fluoro-4-((R)-5-hydroxymethyl-2-oxo-oxazolidin-3-yl)-phenoxymethyl]-16-hydroxy-4-oxo-1,4,13,15,16,17-hexahydro-12H-1-oxa-1,14-diaza-cyclopenta[a]phenanthrene-3-carboxylic acid;

(13S,16S)-1-cyclopropyl-7-fluoro-16-[2-fluoro-4-((R)-2-oxo-5-phosphonooxymethyl-oxazolidin-3-yl)-phenoxymethyl]-4-oxo-16-phosphonooxy-1,4,13,15,16,17-hexahydro-12H-11-oxa-1,14-diaza-cyclopenta[a]phenanthrene-3-carboxylic acid;

(13S,16S)-1-cyclopropyl-7-fluoro-16-[2-fluoro-4-((R)-2-oxo-5-phosphonooxymethyl-oxazolidin-3-yl)-phenoxymethyl]-4-oxo-16-hydroxy-1,4,13,15,16,17-hexahydro-12H-11-oxa-1,14-diaza-cyclopenta[a]phenanthrene-3-carboxylic acid;

(13S,16S)-16-{4-[(R)-5-((S)-2-amino-propionyloxymethyl)-2-oxo-oxazolidin-3-yl]-2-fluoro-phenoxymethyl}-1-cyclopropyl-7-fluoro-16-hydroxy-4-oxo-1,4,13,15,16,17-hexahydro-12H-11-oxa-1,14-diaza-cyclopenta[a]phenanthrene-3-carboxylic acid;

as well as salts thereof (and in particular pharmaceutically acceptable salts thereof).

Chimeric derivatives of formula I or $I_P$ are suitable for the use as medicaments, particularly as antimicrobial agents, in human medicine but also in veterinary medicine in the treatment of species like pigs, ruminants, horses, dogs, cats and poultry.

Chimeric derivatives of formula I or $I_P$ according to the present invention are also useful for the manufacture of a medicament for the treatment of infections (notably bacterial infections or protozoal infections) and disorders related to infections (notably disorders related to bacterial infections or to protozoal infections).

The compounds according to this invention are particularly active against bacteria and bacteria-like organisms. They are therefore particularly suitable in human, as well as in animals, for the prophylaxis and chemotherapy of local and systemic infections caused by these pathogens as well as disorders related to bacterial infections comprising pneumonia, otitis media, sinusitis, bronchitis, tonsillitis, and mastoiditis related to an infection by *Streptococcus pneumoniae, Haemophilus influenzae, Moraxella catarrhalis, Staphylococcus aureus, Enterococcus faecalis, E. faecium, E. casseliflavus, S. epidermidis, S. haemolyticus,* or *Peptostreptococcus* spp.; pharyngitis, rheumatic fever, and glomerulonephritis related to an infection by *Streptococcus pyogenes*, Groups C and G streptococci, *Corynebacterium diphtheriae,* or *Actinobacillus haemolyticum*; respiratory tract infections related to an infection by *Mycoplasma pneumoniae, Legionella pneumophila, Streptococcus pneumoniae, Haemophilus influenzae,* or *Chlamydia pneumoniae*; blood and tissue infections, including endocarditis and osteomyelitis, caused by *S. aureus, S. haemolyticus, E. faecalis, E. faecium, E. durans,* including strains resistant to known antibacterials such as, but not limited to, beta-lactams, vancomycin, aminoglycosides, quinolones, chloramphenicol, tetracyclines and macrolides; uncomplicated skin and soft tissue infections and abscesses, and puerperal fever related to an infection by *Staphylococcus aureus,* coagulase-negative staphylococci (i.e., *S. epidermidis, S. haemolyticus,* etc.), *Streptococcus pyogenes, Streptococcus agalactiae,* Streptococcal groups C-F (minute colony streptococci), viridans streptococci, *Corynebacterium minutissimum, Clostridium* spp., or *Bartonella henselae*; uncomplicated acute urinary tract infections related to an infection by *Staphylococcus aureus,* coagulase-negative staphylococcal species, or *Enterococcus* spp.; urethritis and cervicitis; sexually transmitted diseases related to infection by *Chlamydia trachomatis, Haemophilus ducreyi, Treponema pallidum, Ureaplasma urealyticum,* or *Neiserria gonorrhoeae*; toxin diseases related to an infection by *S. aureus* (food poisoning and toxic shock syndrome), or Groups A, B, and C streptococci; ulcers related to an infection by *Helicobacter pylori*; systemic febrile syndromes related to infection by *Borrelia recurrentis*; Lyme disease related to an infection by *Borrelia burgdorferi*; conjunctivitis, keratitis, and dacrocystitis related to an infection by *Chlamydia trachomatis, Neisseria gonorrhoeae, S. aureus, S. pneumoniae, S. pyogenes, H. influenzae,* or *Listeria* spp.; disseminated *Mycobacterium avium* complex (MAC) disease related to an infection by *Mycobacterium avium,* or *Mycobacterium intracellulare*; infections caused by *Mycobacterium tuberculosis, M leprae, M. paratuberculosis, M. kansasii,* or *M. chelonei*; gastroenteritis related to an infection by *Campylobacter jejuni*; intestinal protozoa related to infection by *Cryptosporidium* spp.; odontogenic infection related to an infection by viridans streptococci; persistent cough related to infection by *Bordetella pertussis*; gas gangrene related to an infection by *Clostridium perfringens* or *Bacteroides* spp.; and atherosclerosis or cardiovascular diseases related to an infection by *Helicobacter pylori* or *Chlamydia pneumoniae*.

Compounds of formula I or $I_P$ according to the present invention are further useful for the preparation of a medicament for the treatment of infections that are mediated by bacteria such as *E. coli, Klebsiella pneumoniae* and other Enterobacteriaceae, *Acinetobacter* spp., *Stenothrophomonas maltophilia, Neisseria meningitidis, Bacillus cereus, Bacillus anthracis, Corynebacterium* spp., *Propionibacterium acnes* and bacteroide spp. In addition, compounds of formula I according to the present invention are further useful for the preparation of a medicament for the treatment of infections that are mediated by *C. difficile*.

Compounds of formula I or $I_P$ according to the present invention are further useful to treat protozoal infections caused by *Plasmodium malaria, Plasmodium falciparum, Toxoplasma gondii, Pneumocystis carinii, Trypanosoma brucei* and *Leishmania* spp.

The preceding lists of pathogens are to be interpreted merely as examples and in no way as limiting.

As well as in humans, bacterial infections can also be treated in other species like pigs, ruminants, horses, dogs, cats and poultry.

Therefore, the compounds of formula I or $I_P$ or their pharmaceutically acceptable salts can be used for the preparation of a medicament, and are suitable, for the prevention or treatment of bacterial infections (notably those caused by the pathogens mentioned in the lists above).

The compounds of formula I or $I_P$ and their pharmaceutically acceptable salts can be used as medicaments, e.g. in the form of pharmaceutical compositions for enteral or parental administration.

The production of the pharmaceutical compositions can be effected in a manner which will be familiar to any person skilled in the art (see for example Mark Gibson, Editor, Pharmaceutical Preformulation and Formulation, 1HS Health Group, Englewood, Colo., USA, 2001; Remington, *The Science and Practice of Pharmacy,* 20th Edition, Philadelphia College of Pharmacy and Science) by bringing the described compounds of formula I or $I_P$ or their pharmaceutically acceptable salts, optionally in combination with other therapeutically valuable substances, into a galenical administration form together with suitable, non-toxic, inert, therapeutically compatible solid or liquid carrier materials and, if desired, usual pharmaceutical adjuvants.

Another aspect of the invention concerns a method for the treatment of an infection comprising the administration to the patient of a pharmaceutically active amount of a compound according to formula I or $I_P$ or of a pharmaceutically acceptable salt thereof.

Furthermore, the compounds of formula I or $I_P$ may also be used for cleaning purposes, e.g. to remove pathogenic microbes and bacteria from surgical instruments or to make a room or an area aseptic. For such purposes, the compounds of formula I could be contained in a solution or in a spray formulation.

Eventually, the invention also relates to certain new synthesis intermediates described in the instant application, namely the compounds of formulae XIa, XIb, $XII_{PG}$, $XII_H$, III, $III'_{PG}$, $III'_H$, $III'_S$, $III'_{ac}$, $III_{ep}$ which are all described in the part entitled "Preparation of compounds of formula I"), provided however that they are such that n represents 1, and to salts of such compounds.

The invention thus also relates to the compounds of the formula $III_{INT}$

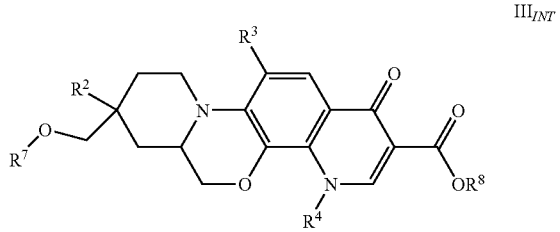

$III_{INT}$ wherein
$R^2$ represents H or OH,
$R^7$ represents H or $SO_2R^9$,
or also $R^2$ and $R^7$ are such that $R^2$ and $OR^7$ form, together with the carbon atoms that carry them, an acetonide ring,
or also $R^2$ and $R^7$ are such that $R^2$ and $OR^7$ form, together with the carbon atoms that carry them, an epoxide ring (in other words, $R^2$ and $R^7$ taken together represent a bond),
$R^3$ represents H or halogen,
$R^4$ represents H, $(C_1-C_3)$alkyl or cycloalkyl,
$R^8$ represents H, $(C_1-C_5)$alkyl, allyl, benzyl, p-nitrobenzyl, p-methoxybenzyl, tri-$(C_1-C_5)$alkylsilyl or diphenyl-$(C_1-C_5)$alkylsilyl, and
$R^9$ represents $(C_1-C_3)$alkyl, trifluoromethyl, phenyl or tolyl;
or to salts of such compounds.

Preferred compounds of formula $III_{INT}$ will be such that they possess at least one (and preferably a combination) of the following characteristics:
$R^2$ represents OH;
$R^7$ represents H or $SO_2R^9$, $R^9$ representing methyl, trifluoromethyl or p-tolyl;
$R^3$ represents halogen (especially fluorine);
$R^4$ represents cycloalkyl (especially cyclopropyl);
$R^8$ represents H or $(C_1-C_5)$alkyl.

Compounds of formula $III_{INT}$ and their salts will preferably be selected from the group consisting of:
(6aS,8R)-4-cyclopropyl-11-fluoro-8-hydroxy-8-hydroxymethyl-1-oxo-1,4,6,6a,7,8,9,10-octahydro-5-oxa-4,10a-diaza-chrysene-2-carboxylic acid ethyl ester;
(6aS,8S)-4-cyclopropyl-11-fluoro-8-hydroxy-8-hydroxymethyl-1-oxo-1,4,6,6a,7,8,9,10-octahydro-5-oxa-4,10a-diaza-chrysene-2-carboxylic acid ethyl ester;
(6aS,8R)-4-cyclopropyl-11-fluoro-8-hydroxy-8-hydroxymethyl-1-oxo-1,4,6,6a,7,8,9,10-octahydro-5-oxa-4,10a-diaza-chrysene-2-carboxylic acid;
(6aS,8S)-4-cyclopropyl-11-fluoro-8-hydroxy-8-hydroxymethyl-1-oxo-1,4,6,6a,7,8,9,10-octahydro-5-oxa-4,10a-diaza-chrysene-2-carboxylic acid;
(6aS,8R)-4-cyclopropyl-11-fluoro-8-hydroxy-8-hydroxymethyl-1-oxo-1,4,6,6a,7,8,9,10-octahydro-5-oxa-4,10a-diaza-chrysene-2-carboxylic acid benzyl ester;
(6aS,8S)-4-cyclopropyl-11-fluoro-8-hydroxy-8-hydroxymethyl-1-oxo-1,4,6,6a,7,8,9,10-octahydro-5-oxa-4,10a-diaza-chrysene-2-carboxylic acid benzyl ester;
(6aS,8R)-4-cyclopropyl-11-fluoro-8-hydroxy-8-methanesulfonyloxymethyl-1-oxo-1,4,6,6a,7,8,9,10-octahydro-5-oxa-4,10a-diaza-chrysene-2-carboxylic acid benzyl ester;
(6aS,8S)-4-cyclopropyl-11-fluoro-8-hydroxy-8-methanesulfonyloxymethyl-1-oxo-1,4,6,6a,7,8,9,10-octahydro-5-oxa-4,10a-diaza-chrysene-2-carboxylic acid benzyl ester;
(6aR,8R)-4-cyclopropyl-11-fluoro-8-hydroxy-8-hydroxymethyl-1-oxo-1,4,6,6a,7,8,9,10-octahydro-5-oxa-4,10a-diaza-chrysene-2-carboxylic acid ethyl ester;
(6aR,8S)-4-cyclopropyl-11-fluoro-8-hydroxy-8-hydroxymethyl-1-oxo-1,4,6,6a,7,8,9,10-octahydro-5-oxa-4,10a-diaza-chrysene-2-carboxylic acid ethyl ester;
(6aR,8R)-4-cyclopropyl-11-fluoro-8-hydroxy-8-hydroxymethyl-1-oxo-1,4,6,6a,7,8,9,10-octahydro-5-oxa-4,10a-diaza-chrysene-2-carboxylic acid;
(6aR,8S)-4-cyclopropyl-11-fluoro-8-hydroxy-8-hydroxymethyl-1-oxo-1,4,6,6a,7,8,9,10-octahydro-5-oxa-4,10a-diaza-chrysene-2-carboxylic acid;
(6aR,8R)-4-cyclopropyl-11-fluoro-8-hydroxy-8-hydroxymethyl-1-oxo-1,4,6,6a,7,8,9,10-octahydro-5-oxa-4,10a-diaza-chrysene-2-carboxylic acid benzyl ester;
(6aR,8S)-4-cyclopropyl-11-fluoro-8-hydroxy-8-hydroxymethyl-1-oxo-1,4,6,6a,7,8,9,10-octahydro-5-oxa-4,10a-diaza-chrysene-2-carboxylic acid benzyl ester;
(6aR,8R)-4-cyclopropyl-11-fluoro-8-hydroxy-8-methane sulfonyloxymethyl-1-oxo-1,4,6,6a,7,8,9,10-octahydro-5-oxa-4,10a-diaza-chrysene-2-carboxylic acid benzyl ester;
(6aR,8S)-4-cyclopropyl-11-fluoro-8-hydroxy-8-methane sulfonyloxymethyl-1-oxo-1,4,6,6a,7,8,9,10-octahydro-5-oxa-4,10a-diaza-chrysene-2-carboxylic acid benzyl ester;
and the salts of these compounds.

Any reference to a compound of formula I, $I_P$, $I_{CE}$, $I_{CEP}$, $I_{T1}$, $I_{5T1}$, $I_{6T1}$, $I_{T2}$, $I_{5T2}$, $I_{6T2}$, $I_{5C1}$, $I_{6C1}$, $I_{C2}$, $I_{5C2}$, $I_{6C2}$, $I_D$ or $I_{PDG}$ is to be understood as referring also to a salt (especially a pharmaceutically acceptable salt) of a compound of formula I, $I_P$, $I_{CE}$, $I_{CEP}$, $I_{T1}$, $I_{5T1}$, $I_{6T1}$, $I_{T2}$, $I_{5T2}$, $I_{6T2}$, $I_{C1}$, $I_{5C1}$, $I_{6C1}$, $I_{C2}$, $I_{5C2}$, $I_{6C2}$, $I_D$ or $I_{PDG}$ respectively, as appropriate and expedient. Besides, any preferences indicated for the compounds of formula I (whether for the compounds themselves, salts thereof, compositions containing the compounds or salts thereof, uses of the compounds or salts thereof, etc.) apply mutatis mutandis to compounds of formula $I_P$, $I_{CE}$, $I_{CEP}$, $I_{T1}$, $I_{5T1}$, $I_{6T1}$, $I_{T2}$, $I_{5T2}$, $I_{6T2}$, $I_{C1}$, $I_{5C1}$, $I_{6C1}$, $I_{C2}$, $I_{5C2}$, $I_{6C2}$, $I_D$ or $I_{PDG}$.

According to the invention, the compounds of formula I can be prepared by the process described hereafter.
Preparation of Compounds of Formula I
Abbreviations:
The following abbreviations are used throughout the specification and the examples:

| | |
|---|---|
| AcOH | acetic acid |
| AD-mix α | 1,4-bis(dihydroquinine)phthalazine, $K_3Fe(CN)_6$, $K_2CO_3$ and $K_2OsO_4 \cdot 2H_2O$ |
| AD-mix β | 1,4-bis(dihydroquinidine)phthalazine, $K_3Fe(CN)_6$, $K_2CO_3$ and $K_2OsO_4 \cdot 2H_2O$ |

| | |
|---|---|
| Alloc | allyloxycarbonyl |
| aq. | aqueous |
| 9-BBN | 9-borabicyclo[3.3.1]nonane |
| BnBr | benzyl bromide |
| Boc | tert-butoxycarbonyl |
| t-BuOK | potassium tert-butylate |
| Cbz | benzyloxycarbonyl |
| DBU | 1,8-diazabicyclo[5.4.0]undec-7-ene |
| DCM | dichloromethane |
| (DHQ)$_2$PHAL | 1,4-bis(dihydroquinine)phthalazine |
| DIAD | diisopropyl azo dicarboxylate |
| DIPEA | N,N-diisopropylethylamine |
| DMA | dimethylacetamide |
| DMAP | 4-dimethylaminopyridine |
| DMF | N,N-dimethylformamide |
| DMSO | dimethylsulfoxide |
| EA | ethyl acetate |
| EDC | 1-(dimethylaminopropy1)-3-ethylcarbodiimide hydrochloride |
| ESI | Electron Spray Ionisation |
| ether or Et$_2$O | diethyl ether |
| EtOH | ethanol |
| h | hour |
| Hex | n-hexane |
| Hept | n-heptane |
| HV | high vacuum conditions |
| MeCN | acetonitrile |
| MCPBA | meta-chloroperbenzoic acid |
| MeOH | methanol |
| ML | mother liquor |
| MS | Mass Spectroscopy |
| NaOMe | sodium methylate |
| NMP | N-methylpyrrolidinone |
| org. | organic |
| Pd/C or Pd(OH)$_2$/C | palladium or palladium dihydroxide on charcoal |
| PPh$_3$ | triphenylphosphine |
| Pt/C | platinum on charcoal |
| RF | retention factor |
| rt | room temperature |
| sat. | saturated |
| SiO$_2$ | silica gel |
| TBDMS | tert-butyldimethylsilyl |
| TBDPS | tert-butyldiphenylsilyl |
| TEA | triethylamine |
| TFA | trifluoroacetic acid |
| THF | tetrahydrofuran |
| THP | tetrahydropyranyl |
| TMS | trimethylsilyl |

General Preparation Routes:

The novel compounds of formula I can be manufactured in accordance with the present invention by a) reacting the compound of formula II

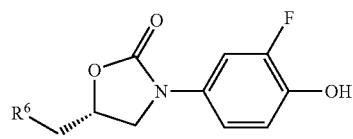

wherein $R^6$ represents OH or O-PG$^1$ and PG$^1$ is a protecting group for a primary alcohol such as acetyl, benzyl, THP, TBDMS, TBDPS or TMS,
with a compound of formula III

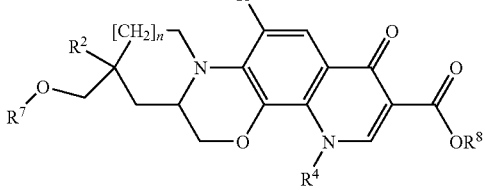

wherein n, $R^3$ and $R^4$ are as defined in formula I, $R^7$ is SO$_2$R$^9$, $R^9$ representing (C$_1$-C$_3$)alkyl (e.g. methyl), trifluoromethyl, phenyl or tolyl, $R^2$ is OH or H, or $R^2$ and $R^7$ together form also a bond (epoxide), or also $R^2$ and OR$^7$ form a cyclic carbonate, sulfate or phosphate, $R^8$ is H, (C$_1$-C$_5$)alkyl (e.g. methyl, ethyl or tert-butyl), allyl, aryl-(C$_1$-C$_5$)alkyl (e.g. benzyl, p-nitrobenzyl or p-methoxybenzyl), tri-(C$_1$-C$_5$)alkylsilyl (e.g. TMS or TBDMS) or diaryl-(C$_1$-C$_5$)alkylsilyl (e.g. TBDPS), preferably between about 10° C. and 100° C. (more preferably between about 40° C. and 80° C.), in the presence of an inorganic base such as K$_2$CO$_3$ or an organic base such as TEA in an organic solvent (e.g. DMF);

or b) ring closing a compound of formula IV

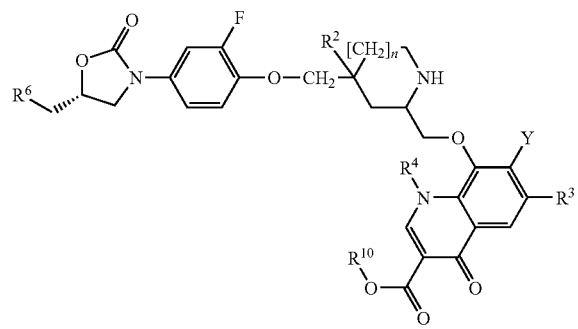

wherein n, $R^2$, $R^3$ and $R^4$ are as defined in formula I, $R^6$ is as defined in formula II, Y is halogen and $R^{10}$ is hydrogen, (C$_1$-C$_5$)alkyl (e.g. methyl, ethyl or tert-butyl), allyl, aryl-(C$_1$-C$_5$)alkyl (e.g. benzyl, p-nitrobenzyl or p-methoxybenzyl), tri-(C$_1$-C$_5$)alkylsilyl (e.g. TMS or TBDMS) or diaryl-(C$_1$-C$_5$)alkylsilyl (e.g. TBDPS), preferably between about 10° C. and 100° C., more preferably between about 40° C. and 80° C. in the presence of an organic base, such as TEA or DIPEA, in an organic solvent, e.g. NMP;

or c) ring closing a compound of formula V

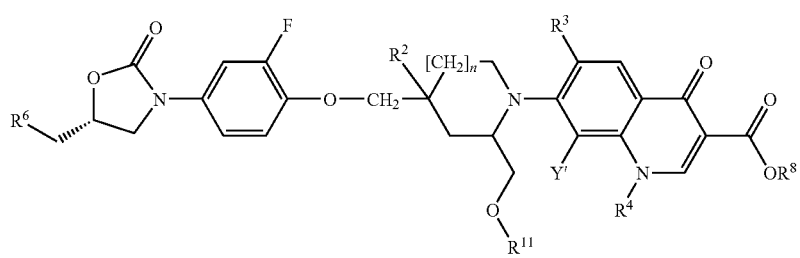

wherein n, $R^2$, $R^3$ and $R^4$ are as defined in formula I, $R^6$ is as defined in formula II, $R^8$ is as defined in formula III, Y' is OH or halogen and $R^{11}$ is H or an alkali metal such as Na or K;

or d) converting the group $R^{13}$ of a compound of formula VI

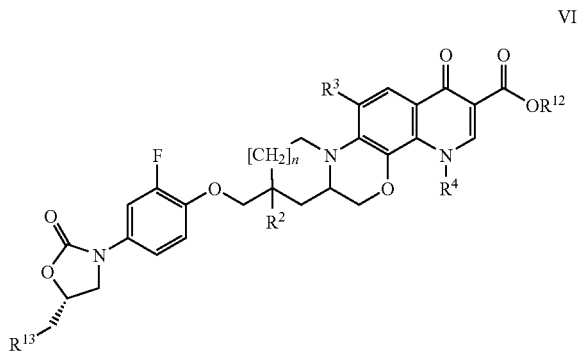

VI wherein n, $R^2$, $R^3$ and $R^4$ are as defined in formula I, $R^{12}$ represents H, aryl-($C_1$-$C_5$)alkyl (e.g. benzyl, p-nitrobenzyl or p-methoxybenzyl), tri-($C_1$-$C_5$)alkylsilyl (e.g. TMS or TBDMS) or diaryl-($C_1$-$C_5$)alkylsilyl (e.g. TBDPS), and $R^{13}$ is either OH or OPO(OR)$_2$, R representing allyl, tert-butyl or benzyl, into one of the groups $R^1$ of formula I as follows:

d1) by reaction of said compound of formula VI wherein $R^{13}$ is OH with the acid derivative of formula $R^5$—COOH in presence of a coupling reagent such as DCC, EDC, HOBT or HATU (G. Benz in *Comprehensive Organic Synthesis*, B. M. Trost, I. Fleming, Eds, Pergamon Press: New York (1991), vol. 6, p. 381), between −20° C. and 60° C. in a dry aprotic solvent like DCM, MeCN or DMF, preferably in the presence of a base such as DMAP, or d2) by deprotection of said compound of formula VI wherein $R^{13}$ is OPO(OR)$_2$ (according to the nature of R, various methods for deprotection may be used as reviewed in *Protecting Groups*, Kocienski, P., J., Thieme (1994), like for example catalytic hydrogenation over a noble catalyst such as palladium or hydrolysis with hydrobromic acid in a solvent such as AcOH when R is benzyl);

or e) converting a compound of formula VII

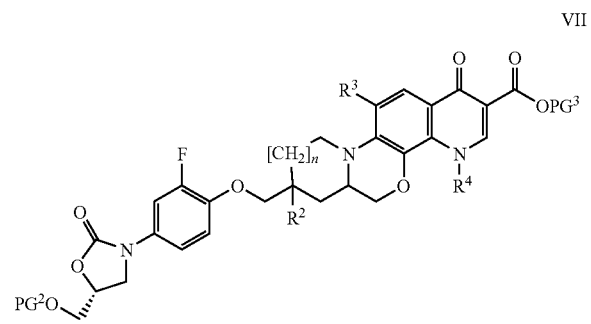

VII wherein n, $R^3$ and $R^4$ are as defined in formula I, $R^2$ is OH, $PG^2$ is tri-($C_1$-$C_5$)alkylsilyl (e.g. TMS or diaryl-($C_1$-$C_5$)alkylsilyl (e.g. TBDPS), $PG^3$ is ($C_1$-$C_5$) alkyl (e.g. methyl, ethyl or tert-butyl), aryl-($C_1$-$C_5$)alkyl (e.g. benzyl, p-nitrobenzyl or p-methoxybenzyl), allyl, tri-($C_1$-$C_5$)alkylsilyl (e.g. TMS or TBDMS) or diaryl-($C_1$-$C_5$)alkylsilyl (e.g. TBDPS), into a compound of formula I wherein $R^2$ is OPO$_3$H$_2$ following the methods described previously in paragraph d), part d2);

or f) converting a compound of formula VIII

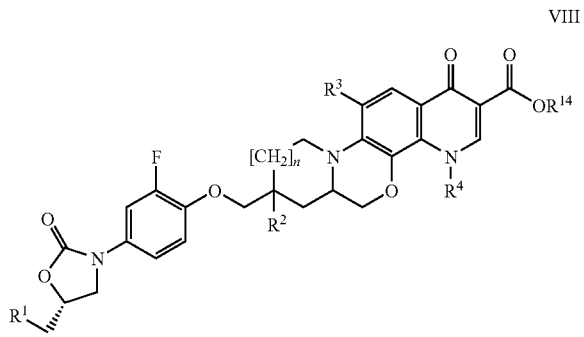

VIII wherein n, $R^2$, $R^3$ and $R^4$ are as defined in formula I and $R^{14}$ is ($C_1$-$C_5$)alkyl (e.g. methyl, ethyl or tert-butyl), aryl-($C_1$-$C_5$)alkyl (e.g. benzyl, p-nitrobenzyl or p-methoxybenzyl), allyl, tri-($C_1$-$C_5$)alkylsilyl (e.g. TMS or TBDMS) or diaryl-($C_1$-$C_5$)alkylsilyl (e.g. TBDPS) into a compound of formula I by hydrolysis, saponification or hydrogenolysis (e.g. as reviewed in *Protecting groups*, Kocienski, P. J., *Thieme* (1994));

or g) converting a compound of formula IX

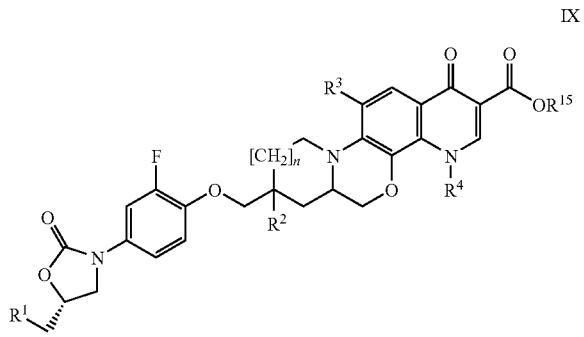

IX wherein n, $R^2$ and $R^3$ are as defined in formula I, $R^1$ is OH, tri-($C_1$-$C_5$)alkylsilyloxy (e.g. O-TMS or O-TBDMS) or diaryl-($C_1$-$C_5$)alkylsilyloxy (e.g. O-TBDPS), $R^4$ is cyclopropyl, and $R^{15}$ is H, ($C_1$-$C_5$)alkyl (e.g. methyl, ethyl or tert-butyl), aryl-($C_1$-$C_5$)alkyl (e.g. benzyl, p-nitrobenzyl or p-methoxybenzyl), tri-($C_1$-$C_5$)alkylsilyl (e.g. TMS or TBDMS) or diaryl-($C_1$-$C_5$)alkylsilyl (e.g. TBDPS) into a compound of formula I wherein $R^4$ is H by hydrogenolysis over a noble metal catalyst such as palladium or platinum in a polar solvent such as DMA and at a temperature between 20 and 120° C. (and preferably at a temperature between 70 and 90° C.).

Concerning the above process, the following should be noted:

regarding variants a), b) and c), when $R^6$ is O-PG$^1$, an additional deprotection step is required (general methods to perform such reactions have been reviewed in *Protecting groups*, Kocienski, P. J., Thieme (1994));

concerning variants a, b), c) and d), when $R^8$, $R^{10}$ or $R^{12}$ are not H, an additional hydrolysis step is required, which can be performed by applying one of the methods proposed in variant e);

regarding variant a), when $R^2=R^7=H$, the reaction is performed under Mitsunobu conditions (as described in *Synthesis* (1981), 1, 1-28);

regarding variant b), the compound of formula IV could also be replaced by an activated form thereof, i.e. the same compound except that $R^{10}$ would represent $BF_2$ or $B(OC(=O)(C_1-C_4)alkyl)_2$;

concerning variant c):
  when $R^{11}$ is H and Y' is OH, the reaction is performed under Mitsunobu conditions (as described in *Synthesis* (1981), 1, 1-28), and
  when $R^{11}$ is Na or K and Y' is halogen, the reaction is performed in a solvent such as THF, N,N-dimethylimidazoline-2-one or DMF at a temperature between about 40° C. and 80° C.;

concerning variant d), when $R^{12}$ is not H, an additional deprotection step such as the ones described in variant f) of the above process is required;

regarding variant e), additional deprotections step are required to remove the protecting groups $PG^2$ and $PG^3$ (general methods to perform such reactions have been reviewed in *Protecting groups*, Kocienski, P. J., Thieme (1994));

The compounds of formula I obtained according to the abovementioned general preparation methods may then, if desired, be converted into their salts, and notably into their pharmaceutically acceptable salts.

Besides, whenever the compounds of formula I are obtained in the form of mixtures of enantiomers, the enantiomers can be separated using methods known to one skilled in the art (e.g. by formation and separation of diastereomeric salts or by chromatography over a chiral stationary phase). Whenever the compounds of formula I are obtained in the form of mixtures of diasteromers they may be separated by an appropriate combination of silica gel chromatography, HPLC and crystallization techniques.

According to the invention, the compounds of formula I can be prepared by the methods described hereafter.

Preparation of the Various Synthesis Intermediates:
Preparation of the Compounds of Formula II The compounds of formula II can be obtained by hydrogenation of the compounds of formula X

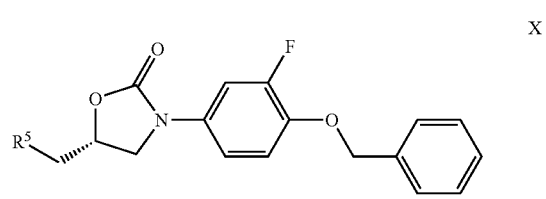

over a noble metal catalyst such as Pd/C or Pt/C in a solvent such as THF, MeOH or AcOEt between 0° C. and 40° C. or, for the compound of formula II wherein $R^6$ is OH, by hydrolysis in presence of a solution of HBr in water or in AcOH between 0° C. and 80° C. in a solvent such as AcOH. The compound of formula X wherein $R^6$ is OH was obtained according to WO 2004/096221. The compounds of formula X wherein $R^6$ is $OPO_3H_2$ or $OCOR^6$ can be prepared following the methods proposed in part d) of the "General preparation routes" section.

Preparation of the Compounds of Formula III

The compounds of formula III can be prepared according to the chemical routes shown in Scheme 1 hereafter.

Scheme 1

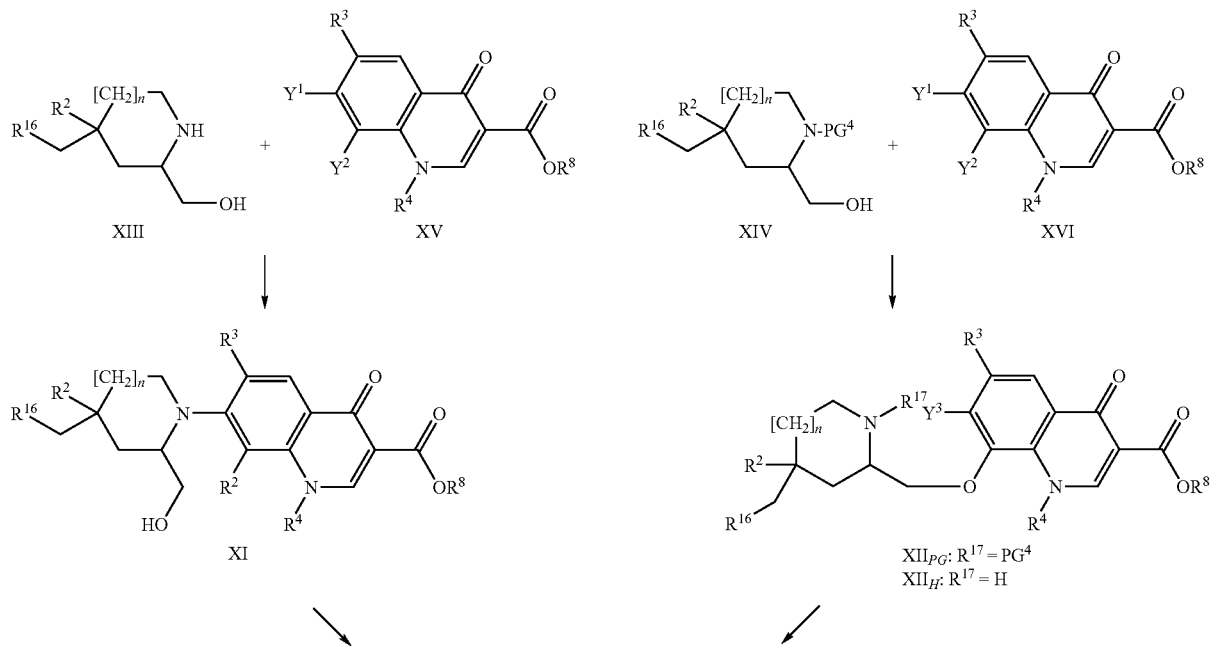

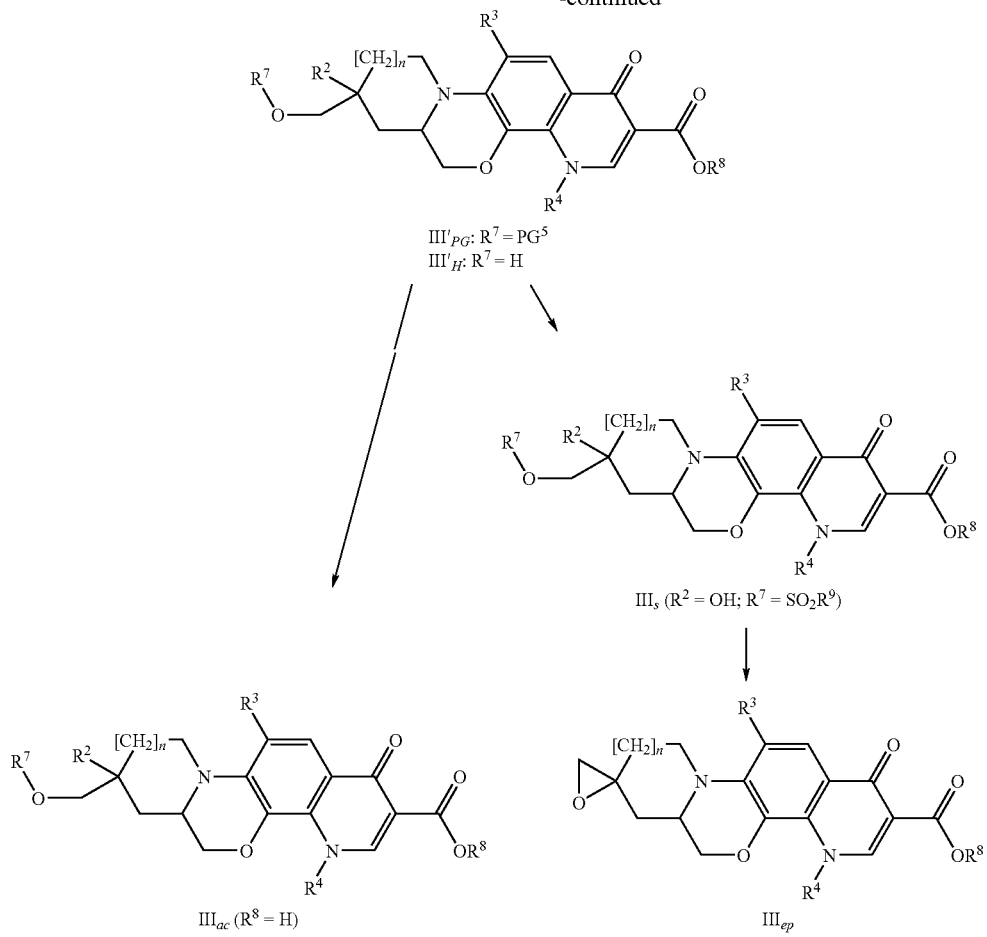

Compounds of formula III$_S$ (Scheme 1), wherein R$^2$ is OH, R$^7$ is SO$_2$R$^9$, R$^9$ being alkyl, trifluoromethyl or aryl like phenyl or p-tolyl are obtained from compounds of formula III'$_H$ (wherein R$^7$ is H) by reaction with the corresponding sulfonyl chlorides in presence of an organic base such as TEA in a solvent such as DCM or THF between −10° C. and 50° C. Compounds of formula III$_s$ can be used for the preparation of the spiro oxirane derivatives of formula III$_{ep}$, which reaction is carried out under basic conditions (e.g. with Na$_2$CO$_3$ in a solvent like DMF). Compounds of formula III'$_H$ (wherein R$^7$=H) are obtained from compounds of formula III$_{PG}$ wherein R$^7$ is PG$^5$. Typical protecting groups PG$^5$ that can be used are THP ethers, methoxymethyl or 2-methoxyethoxymethyl ethers, allyl ethers, trialkylsilyl ethers or alkyl esters; their formation and removal are described in *Protecting groups*, Kocienski, P. J., Thieme (1994). Compounds of formula III'$_{PG}$ (wherein R$^8$ is H, alkyl or arylalkyl) are prepared by intramolecular ring closure, either under Mitsunobu conditions (when Y$^2$ is OH) or, after prior transformation of the primary alcohol function of compound of formula XI (wherein Y$^2$ is OH) into its alkyl- or aryl-sulfonate followed by ring closure under basic conditions such as Na$_2$CO$_3$ or DBU in a solvent like THF or DMF between 20° C. and 100° C. Compounds of formula PG can also be prepared from compounds of formula XI wherein Y$^2$=F by intramolecular ring closure in presence of a strong base such as NaH, LDA, DBU or an alkali alkoxylate. When R$^{16}$ and R$^2$ together form an acetonide, the resulting acetonide derivative of formula III'$_H$ is treated with an acid to give the corresponding compound of formula III'$_H$ wherein R$^2$=OH and R$^7$=H. Alternatively, compounds of formula III'$_H$ or III'$_{PG}$ can be obtained from compounds of formula XII$_H$ (wherein R$^8$ is H, alkyl or arylalkyl and R$^{17}$ is H) after intramolecular ring closure in a solvent like THF, NMP or DMF between 20° C. and 100° C. If R$^8$ is alkyl or arylalkyl, the free acid of formula III$_{ac}$ is liberated according to standard procedures as described in *Protecting groups*, Kocienski, P. J., Thieme (1994) (e.g. hydrogenation over Pd/C for R$^8$=benzyl; acidic treatment with TFA or a solution of HCl in an organic solvent such as THF or MeOH for R$^8$=tert-butyl; acidic or basic hydrolysis for R$^8$=methyl or ethyl).

Compounds of formula XI are obtained (Scheme 1) from the 7,8-dihalo-1,4-dihydro-4-oxoquinoline-3-carboxylic acid derivatives of formula XV (wherein Y$^1$ and Y$^2$ are both halogen atoms and R$^8$ is H, alkyl or arylalkyl) by reaction with the pyrrolidine derivatives of formula XIII (wherein R$^{16}$ is O-PG$^5$, PG$^5$ being as defined for the compounds of formula III'$_{PG}$, and R$^2$ is H or OH or R$^{16}$ and R$^2$ together form an acetonide and the other symbols are as before), in a polar solvent such as NMP in the presence of an organic base like TEA or DIPEA, between about 30° C. and 100° C., preferably between about 50° C. and 80° C. Optionally, the compounds of formula XV can be transiently transformed into their corresponding borane derivatives (i.e. the same compounds except that R$^8$ would represent BF$_2$ or B(OC(=O)(C$_1$-C$_4$) alkyl)$_2$).

Compounds of formula XII$_H$ are obtained by removal of the protecting group of the compounds of formula XII$_{PG}$ (R$^{17}$=PG$^4$) using standard methods. According to the nature of the protecting group, several strategies may be used to unmask the amino group, such as using TFA in the case of Boc and Cbz or hydrogenolysis using a catalyst such as Pd/C and hydrogen in the case of the Cbz group.

Compounds of formula XII$_{PG}$ are obtained (Scheme 1) by reacting the 8-hydroxy-7-halo-1,4-dihydro-4-oxo-quinoline-3-carboxylic acid derivatives of formula XVI either with alcohol derivatives of formula XIV (wherein R$^{16}$ is O-PG$^5$, PG$^5$ being as defined for the compounds of formula III'$_{PG}$, and R$^2$ is H or OH, and PG$^4$ can be e.g. benzyl, Boc, Alloc or Cbz—a variety of other protecting groups may however be used as reviewed in *Protecting groups*, Kocienski, P. J., *Thieme* (1994)) under Mitsunobu conditions or with the corresponding alkyl or aryl sulfonates of the alcohols of formula XIV obtained after reaction with a (C$_1$-C$_3$)alkylsulfonyl halide (e.g. methylsulfonyl chloride) or aryl-sulfonyl halide (like phenyl- or p-toluenesulfonyl chloride) between about −30° C. and 60° C., preferably between about −10° C. and +30° C., in a solvent like THF or DCM in the presence of an organic base like TEA or pyridine.

Compounds of formula XIII are obtained by deprotection of compounds of formula XIV. Compounds of formula XIV wherein R$^{16}$ and R$^2$ are both OH can be prepared from the corresponding 4-methylidene derivatives by Sharpless asymmetric dihydroxylation using AD-mix α or β (*J. Org. Chem.* (1992), 57, 2768). The primary alcohol function is optionally transformed into its corresponding sulfonate by reaction with an alkyl or aryl sulfonyl chloride as described above.

Compounds of formula XIV wherein R$^2$ is H and R$^{16}$ is OH can be obtained by hydroboration of the corresponding 4-methylidene derivatives with borane-dimethyl sulfide complex or borabicyclo[3.3.1]nonane as described in *J. Am. Chem. Soc.* (1968), 90, 5281.

Preparation of the Compounds of Formula IV

The compounds of formula IV wherein Y=Y$^3$=halogen can be prepared as summarized in Scheme 2 hereafter.

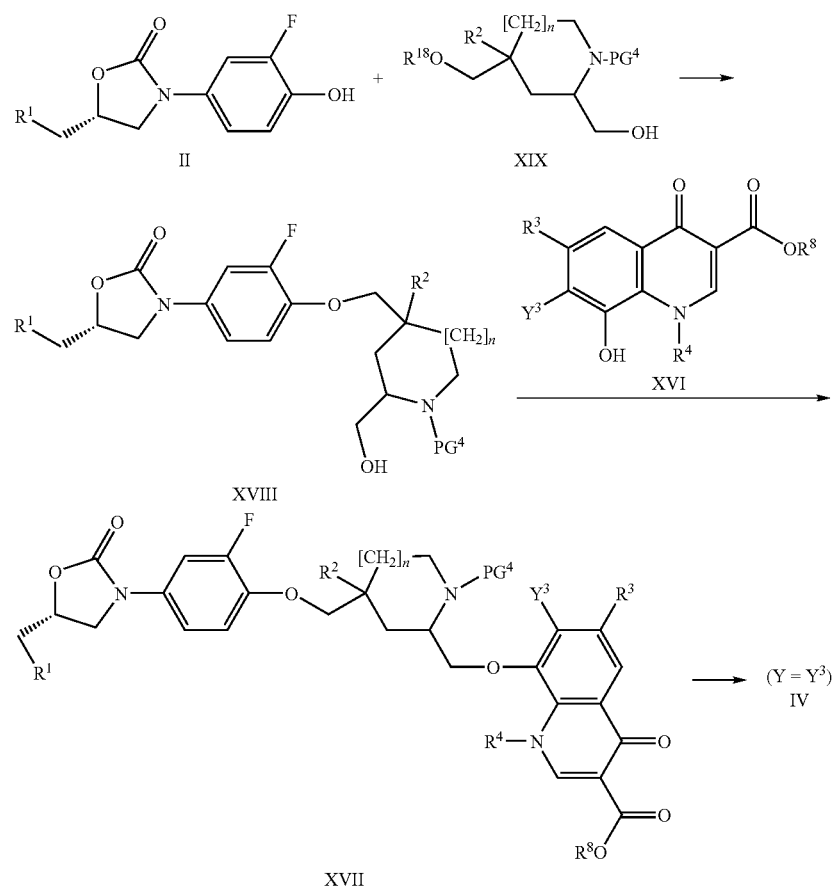

The compounds of formula IV wherein Y=Y$^3$=halogen are obtained (Scheme 2) by N-deprotecting compounds of formula XVII using standard conditions (e.g. TFA neat or diluted in an organic solvent such as DCM or HCl in an organic solvent such as ether or THF for Boc). Compounds of formula XVII are obtained by coupling the 8-hydroxy-7-halo-1,4-dihydro-4-oxo-quinoline-3-carboxylic acid derivatives of formula XVI previously described with compounds of formula XVIII either under Mitsunobu conditions or after prior transformation of the primary alcohol function of XVIII into its corresponding mesylate and treatment with an inorganic base such as Na$_2$CO$_3$ or an organic base such as DBU.

Compounds of formula XVIII are obtained by reacting the compounds of formula XIX wherein R$^{18}$ is alkyl-, trifluoromethyl- or aryl-sulfonyl and R$^2$ is H or OH or R$^2$ and R$^{18}$ close an epoxide ring, with a compound of formula II under the conditions described for the reaction of compounds of formula II with compounds of formula III.

Preparation of the Compounds of Formula V

The compounds of formula V wherein $R^{11}$ is H can be prepared as summarized in Scheme 3 hereafter.

for compounds of formula VI wherein $R^{12}$ represents aryl-$(C_1$-$C_5)$alkyl, tri-$(C_1$-$C_5)$alkylsilyl or diaryl-$(C_1$-$C_5)$ alkylsilyl, by coupling (as described in variant a) of the general preparation routes) compounds of formula II wherein $R^6$ is O-$PG^1$ with compounds of formula III wherein $R^2$ is H or OH and $R^8$ is aryl-$(C_1$-$C_5)$alkyl, Scheme 3

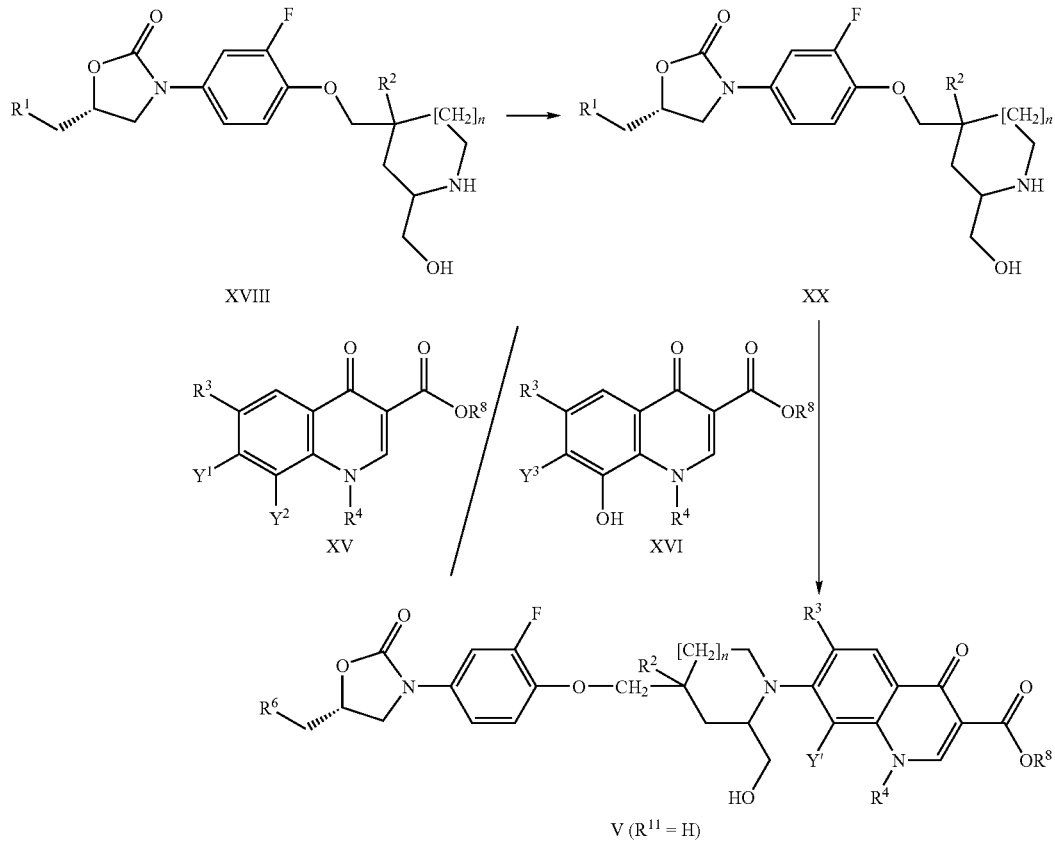

The compounds of formula V wherein $R^{11}$ is H are obtained (Scheme 3) by reacting compounds of formula XX either with the 7,8-dihalo-1,4-dihydro-4-oxoquinoline-3-carboxylic acid derivatives of formula XV or with the 7-halo-8-hydroxy-1,4-dihydro-4-oxoquinoline-3-carboxylic acid derivatives of formula XVI previously described under the same conditions as those described previously for the preparation of compounds of formula XIa. Optionally, the compounds of formula XV or XVI can be replaced by their borane derivatives (i.e. the same compounds except that $R^8$ would represent $BF_2$ or $B(OC(=O)(C_1$-$C_4)$alkyl$)_2$). Compounds of formula XX are prepared by deprotection of compounds of formula XVIII using standard methods.

The compounds of formula V wherein $R^{11}$ is an alkali metal can be obtained starting from the compounds of formula V wherein $R^{11}$ is H using standard methods.

Preparation of the Compounds of Formula VI

The compounds of formula VI wherein $R^{13}$ is OH can be obtained as follows:

for compounds of formula VI wherein $R^{12}$ represents H, by any route already described for obtaining compounds of formula I wherein $R^1$ represents OH;

tri-$(C_1$-$C_5)$alkylsilyl or diaryl-$(C_1$-$C_5)$alkylsilyl and removing afterwards the protecting group O-$PG^1$ by standard methods.

The compounds of formula VI wherein $R^{13}$ is OPO(OR)$_2$ can be obtained by converting compounds of formula VI wherein $R^{13}$ is OH with a phosphoramidite derivative of the formula XXI

XXI

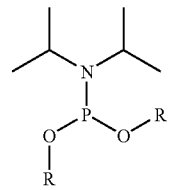

wherein R is benzyl, allyl or tert-butyl in presence of tetrazole or 4,5-dicyanoimidazole in a solvent such as DCM between −40° C. and 30° C. followed by in situ oxidation with an oxidizing agent such as tert-butyl hydroperoxide, hydrogen peroxide or an organic peracid such as MCPBA between 0° C. and 30° C.

Preparation of the Compounds of Formula VII

The compounds of formula VII can be obtained by coupling (as described in variant a) of the general preparation routes) the appropriate compounds of formula II wherein $R^6$ is O-$PG^1$ with the appropriate compounds of formula $III_S$ previously described wherein $R^8$ is not H.

Preparation of the Compounds of Formula VIII

The compounds of formula VIII wherein $R^1$ is OH can be obtained by coupling (as described in variant a) of the general preparation routes) the appropriate compounds of formula II wherein $R^6$ is OH with the appropriate compounds of formula $III_S$ previously described wherein $R^8$ is not H.

The compounds of formula VIII wherein $R^1$ is $OPO_3H_2$ can be obtained from compounds of formula VIII wherein $R^1$ is OH by reaction with a compound of formula XXI as described regarding the preparation of compounds of formula VI wherein $R^{13}$ is $OPO(OR)_2$.

The compounds of formula VIII wherein $R^1$ is $OCOR^5$ can be obtained from compounds of formula VIII wherein $R^1$ is OH by reaction with an acid derivative of formula $R^5$—COOH as described in variant d2) of the general preparation routes.

Preparation of the Compounds of Formula IX

The compounds of formula IX either are compounds of formula VI or VII or can be obtained from these compounds by using standard methods.

The following examples further illustrate the preparation of the pharmacologically active compounds of the invention but do not limit the scope thereof.

EXAMPLES

All temperatures are stated in ° C. All analytical and preparative HPLC investigations on non-chiral phases are performed using RP-C18 based columns. Analytical HPLC investigations are performed on two different instruments with cycle-times of ~2.5 min and ~3.5 min respectively. Unless otherwise stated, the values indicated for MS correspond to the main peaks ((M+H)$^+$ with a variation of +/−0.5 unit) obtained using the ESI method. In NMR spectra, coupling constants J are given in Hz.

Standard Work-Up Procedure:

After dilution in the appropriate org. solvent (see corresponding Example text), the org. phase is separated and sequentially washed with water and brine. In case of reaction performed in a water soluble solvent (e.g. MeOH, THF or DMF), the combined aq. layers are back-washed with the same solvent used to perform the workup. The combined org. phases are dried over $MgSO_4$ and filtered. The filtrate is evaporated under reduced pressure.

Standard Chromatography Procedure:

The crude material is dissolved in the minimum of eluent (see corresponding Example text) and chromatographed over $SiO_2$. The relevant fractions were pooled and evaporated under reduced pressure.

Example 1

(13S,16S)-1-cyclopropyl-7-fluoro-16-[2-fluoro-4-((R)-5-hydroxymethyl-2-oxo-oxazolidin-3-yl)-phenoxymethyl]-16-hydroxy-4-oxo-1,4,13,15,16,17-hexahydro-12H-11-oxa-1,14-diaza-cyclopenta[a]phenanthrene-3-carboxylic acid:

1.i. 1-cyclopropyl-6,7-difluoro-8-hydroxy-4-oxo-1,4-dihydro-quinoline-3-carboxylic acid A solution of 1-cyclopropyl-6,7-difluoro-8-methoxy-4-oxo-1,4-dihydro-quinoline-3-carboxylic acid (13.02 g) in HBr in AcOH (33%; 100 ml) was stirred at 100° C. for 1 day. The reaction mixture was cooled to 0° C. and diluted with water (400 ml). The resulting crystals were collected by filtration, affording, after drying, 12.4 g of a colourless material.

$^1$H NMR (DMSO$_{d6}$; δ ppm): 1.09-1.23 (4H, m); 4.32 (1H, m); 7.70 (dd, 1H, J=8 and J=10); 8.75 (1H, s); 11.66 (1H, broad); 14.78 (1H, s).

1.ii. 8-benzyloxy-1-cyclopropyl-6,7-difluoro-4-oxo-1,4-dihydro-quinoline-3-carboxylic acid A solution of intermediate 1.i (1 g) in DMF (15 ml) was treated with 1N NaOH (3.56 ml). After stirring for 15 min, the yellow solution was treated with BnBr (486 µl). The reaction mixture was stirred at rt for 1 h, diluted with water (50 ml) and the resulting colourless crystals were filtered, affording, after drying, 1.2 g of a solid.

MS: 372.1.

1.iii. 8-benzyloxy-1-cyclopropyl-6,7-difluoro-4-oxo-1,4-dihydro-quinoline-3-carboxylic acid ethyl ester A solution of intermediate 1.ii (59.23 g) in DMF (300 ml) was treated with $K_2CO_3$ (24.24 g) and ethyl bromide (14.28 ml) and heated at 50° C. for 1 h. The solvents were removed under reduced pressure and the residue was dissolved in DCM and washed with brine. The org. layer was dried over $MgSO_4$, filtered and evaporated under reduced pressure. The residue was suspended in EA/ether and stirred at 0° C. before filtration and drying under reduced pressure, affording 51.72 g of colourless crystals.

MS: 399.8.

1.iv. 1-cyclopropyl-6,7-difluoro-1,4-dihydro-8-hydroxy-4-oxo-3-quinolinecarboxylic acid ethyl ester A solution of intermediate 1.iii (52.38 g) in THF (900 ml) and EtOH (100 ml) was hydrogenated over Pd(OH)$_2$ (3 g) for 2 h. The suspension was diluted with DCM (1 l) and EtOH (100 ml), heated to 35° C. and filtered. The ML was concentrated in vacuo and the crystals were collected by filtration. The solid was suspended in hot EA (300 ml) and stirred for 1 h. The suspension was filtered to afford colourless crystals (37 g).

MS: 310.1.

1.v. 8-((2S)-1-tert-butoxycarbonyl-4-methylene-pyrrolidin-2-ylmethoxy)-1-cyclopropyl-6,7-difluoro-4-oxo-1,4-dihydro-quinoline-3-carboxylic acid ethyl ester A solution of (2S)-2-(hydroxymethyl)-4-methylene-1-pyrrolidinecarboxylic acid tert-butyl ester (2.58 g; *J. Org. Chem.* (2003), 68, 3923-3931), intermediate 1.iv (3.56 g) and PPh$_3$ (4.44 g) in THF (100 ml) was treated dropwise over 1.5 h with a solution of DIAD (2.85 ml) in THF (7 ml). The reaction was further stirred at rt for 16 h. The solvent was removed under reduced pressure and the residue was stirred in a mixture of ether/Hex (150 ml 1/1). The solid was filtered off and the filtrate was concentrated in vacuo. The residue was again stirred in the same solvent mixture and the second crop of crystals was filtered off. The filtrate was concentrated in vacuo and the residue was purified by chromatography over $SiO_2$ (EA/Hex 1:9). The relevant fractions were pooled, evaporated under reduced pressure and crystallized from EA/Hex (1:1) affording 4.48 g of title compound as a colourless solid.

MS: 505.5.

1.vi. 8-((2S)-1-tert-butoxycarbonyl-4-methylene-pyrrolidin-2-ylmethoxy)-1-cyclopropyl-6,7-difluoro-4-oxo-1,4-dihydro-quinoline-3-carboxylic acid A solution of intermediate 1.v (1.01 g) in dioxane (10 ml) was treated with lithium hydroxide monohydrate (0.17 mg) and water (1.5 ml). The reaction mixture was stirred at rt for 1 day. The org. solvent was removed under reduced pressure and the aq. residue was diluted with water (2 ml) and acidified to pH 2 with 1N HCl. The resulting solid was collected by filtration and dried under HV to afford 0.84 g of a colourless solid.

$^1$H NMR (DMSO$_{d6}$; δ ppm): 1.08-1.25 (4H, m); 1.40 (9H, s); 2.70 (1H, m); 2.90 (1H, m); 3.83 (1H, m); 4.00 (1H, m); 4.10-4.24 (3H, m); 4.30 (1H, m); 5.07 (2H, m); 8.05 (1H, m); 8.78 (1H, s); 14.50 (1H, s).

MS: 477.2.

1.vii. 8-((2S)-1-tert-butoxycarbonyl-4-methylene-pyrrolidin-2-ylmethoxy)-1-cyclopropyl-6,7-difluoro-4-oxo-1,4-dihydro-quinoline-3-carboxylic acid benzyl ester A solution of intermediate 1.vi (899 mg) in DMF (5 ml) was treated with K$_2$CO$_3$ (365 mg) and BnBr (0.23 ml). The reaction mixture was stirred at 60° C. for 3 h. The solvent was removed under reduced pressure and the residue was dissolved in DCM and washed with brine. The org. layer was dried over MgSO$_4$, filtered and evaporated. The residue was crystallized from ether/Hex to give a pale yellow solid (867 mg).

$^1$H NMR (DMSO$_{d6}$; δ ppm): 1.00-1.15 (4H, m); 1.40 (9H, s); 2.65 (1H, m); 2.87 (1H, m); 3.80 (1H, m); 3.93-4.26 (4H, m); 4.3 (1H, m); 5.06 (2H, m); 5.28 (2H, s); 7.30-7.42 (3H, m); 7.45-7.51 (2H, m) 7.87 (1H, m); 8.57 (1H, s).

MS: 567.5.

1.viii. 8-[(2S,4S))-(1-tert-butoxycarbonyl-4-hydroxy-4-hydroxymethyl-pyrrolidin-2-ylmethoxy)]-1-cyclopropyl-6,7-difluoro-4-oxo-1,4-dihydro-quinoline-3-carboxylic acid benzyl ester A mixture of tert-butanol (10 ml) and water (10 ml) was stirred with potassium ferricyanide III (1.51 g), potassium osmate dehydrate (0.006 g), K$_2$CO$_3$ (0.64 g) and (DHQ)$_2$PHAL (0.024 g) until two clear phases were formed. Intermediate 1.vii (0.867 g) was added and the reaction mixture stirred at 0° C. and monitored by HPLC. The reaction was stirred during 3 days and treated carefully at rt with sodium pyrosulfide (2.3 g). The mixture was diluted with DCM, the water layer washed twice with DCM. The combined org. layers were washed with brine, dried over MgSO$_4$/Fuller's earth and filtered. The filtrate was evaporated to dryness under reduced pressure. The residue was purified by chromatography (eluent: DCM/MeOH 95/5), affording a foam (0.914 g; 98% yield).

MS: 601.1.

1.ix. 1-cyclopropyl-6,7-difluoro-8-[(2S,4S)-4-hydroxy-4-hydroxymethyl-pyrrolidin-2-ylmethoxy]-4-oxo-1,4-dihydro-quinoline-3-carboxylic acid benzyl ester hydrochloride Intermediate 1.viii (900 mg) was dissolved in a 3.7M HCl solution in dioxane (10 ml). The solution was treated with a few drops of water and the mixture was stirred at rt for 30 min. The solvent was removed under reduced pressure and the residue was stirred in EA. The crystals were collected by filtration and dried under HV, affording a colourless solid (802 mg).

MS: 501.2.

1.x. (13S,16S)-1-cyclopropyl-7-fluoro-16-hydroxy-16-hydroxymethyl-4-oxo-1,4,13,15,16,17-hexahydro-12H-11-oxa-1,14-diaza-cyclopenta[a]phenanthrene-3-carboxylic acid benzyl ester A solution of intermediate 1.ix (802 mg) in NMP (4 ml) was treated with NaHCO$_3$ (313 mg) and DIPEA (0.256 ml). The mixture was stirred at 80° C. for 1 h. The solvent was removed under reduced pressure and the residue, dissolved in a DCM/MeOH (9:1) mixture, was washed with water and brine. The org. layer was dried over MgSO$_4$, filtered and concentrated in vacuo. The residue was crystallized from MeCN to afford a solid (215 mg).

$^1$H NMR (DMSO$_{d6}$; δ ppm): 0.9-1.10 (4H, m); 1.65 (1H, dd, J=13 and J=10); 2.34 (1H, dd, J=13 and J=8); 3.35 (1H, m); 3.44 (2H, d, J=4); 3.58 (1H, m); 3.75 (1H, m); 3.93 (1H, dd, J=10 and J=7); 4.07 (1H, m); 4.48 (1H, dd, J=10 and J=7); 4.86 (1H, s); 4.96 (1H, t, J=4); 5.15 (2H, s); 7.26-7.50 (6H, m); 8.45 (1H, s).

MS: 481.3.

1.xi. (13S,16S)-1-cyclopropyl-7-fluoro-16-hydroxy-16-methanesulfonyloxymethyl-4-oxo-1,4,13,15,16,17-hexahydro-12H-11-oxa-1,14-diaza-cyclopenta[a]phenanthrene-3-carboxylic acid benzyl ester A solution of intermediate 1.x (215 mg) in pyridine (0.7 ml) was treated with mesyl chloride (56 mg). The reaction was monitored by HPLC. The pyridine was evaporated under reduced pressure and the residue was dissolved in DCM. The org. layer was washed with water, 0.1N HCl and brine, dried over MgSO$_4$, filtered and the filtrate evaporated. The residue was purified by chromatography (eluent: DCM/MeOH 95/5). The residue was crystallized from an EA/Hex mixture to afford 205 mg (82% yield) of a colourless foam.

$^1$H NMR (DMSO$_{d6}$; δ ppm): 0.9-1.10 (4H, m); 1.82 (1H, dd, J=14 and J=3); 2.33 (1H, dd, J=14 and J=8); 3.24 (3H, s); 3.47 (1H, dd, J=10 and J=3); 3.65 (1H, m); 3.72 (1H, m); 3.93 (1H, dd, J=14 and J=3); 4.07 (1H, m); 4.30 (2H, s); 4.51 (1H, dd, J=10 and J=3); 5.16 (2H, s); 7.28-7.50 (6H, m); 8.47 (1H, s).

MS: 559.1.

1.xii. (R)-3-(3-fluoro-4-hydroxy-phenyl)-5-hydroxymethyl-oxazolidin-2-one

A solution of (R)-3-(4-benzyloxy-3-fluoro-phenyl)-5-hydroxymethyl-oxazolidin-2-one (6.34 g, prepared according to WO 2004/096221) in THF/MeOH (1:1; 200 ml) was hydrogenated over Pd/C 10% (1 g) overnight. The catalyst was filtered off, the filtrate evaporated under reduced pressure and the residue stirred in EA. The crystals were collected by filtration affording 3.16 g (70% yield) of a colourless solid.

$^1$H NMR (DMSO$_{d6}$; δ ppm): 3.5 (m, 1H), 3.64 (m, 1H), 3.74 (dd, J=9 and J=6, 1H), 3.99 (t, J=9, 1H), 4.64 (m, 1H), 5.16 (t, J=6, 1H), 6.93 (dd, J=10 and J=9, 1H), 7.08 (ddd, J=9, J=3 and J=1, 1H), 7.45 (dd, J=14 and J=3, 1H), 9.66 (s, 1H).

MS: 228.1.

1.xiii. (13S,16S)-1-cyclopropyl-7-fluoro-16-[2-fluoro-4-((R)-5-hydroxymethyl-2-oxo-oxazolidin-3-yl)-phenoxymethyl]-16-hydroxy-4-oxo-1,4,13,15,16,17-hexahydro-12H-11-oxa-1,14-diaza-cyclopenta[a]phenanthrene-3-carboxylic acid benzyl ester A solution of intermediates 1.xi (1.12 g) and 1.xii (477 mg) in dry DMF (10 ml) was treated with $K_2CO_3$ (414 mg). The reaction was stirred at 80° C. for 5 h. The DMF was evaporated under reduced pressure and the residue was dissolved in DCM/MeOH 9/1, worked up and chromatographed (DCM/MeOH 95:5) affording 0.923 g (67% yield) of an amorphous foam.
$^1$H NMR (DMSO$_{d6}$; δ ppm): 0.90-1.12 (4H, m); 1.86 (1H, dd, J=4 and J=14); 2.45 (1H, dd, J=9 and J=14); 3.51-3.60 (2H, m); 3.63-3.71 (2H, m); 3.78 (1H, t, J=10); 3.81 (1H, dd, J=6 and J=9); 4.01-4.10 (3H, m); 4.12 (2H, s); 4.53 (1H, dd, J=3 and J=10); 4.66-4.73 (1H, m); 5.20 (1H, t, J=6); 5.27 (2H, s); 5.35 (1H, s); 7.21-7.35 (3H, m); 7.37-7.42 (2H, m); 7.45-7.51 (3H, m); 7.57-7.53 (1H, m); 8.46 (1H, s).
MS: 689.8.

1.xiv. (13S,16S)-1-cyclopropyl-7-fluoro-16-[2-fluoro-4((R)5 hydroxymethyl-2-oxo-oxazolidin-3-yl)-phenoxymethyl]-16-hydroxy-4-oxo-1,4,13,15,16,17-hexahydro-12H-11-oxa-1,14-diaza-cyclopenta[a]phenanthrene-3 carboxylic acid A solution of intermediate 1.xiii (920 mg) in THF/MeOH (50 ml; 1:1) was hydrogenated overnight over 10% Pd(OH)$_2$/C (0.2 g). The catalyst was filtered off, the filtrate evaporated and the residue stirred in DCM/MeOH (8:2; 200 ml). The slurry was filtered, the filtrate was evaporated under reduced pressure and stirred in DCM (50 ml). The crystals were collected to afford 0.468 g (59% yield) of yellow solid.
$^1$H NMR (DMSO$_{d6}$; δ ppm): 0.98-1.15 (4H, m); 1.86 (1H, dd, J=4 and J=14); 2.40-2.46 (1H, m); 3.50-3.82 (6H, m); 4.00-4.08 (2H, m); 4.11 (2H, s); 4.17-4.26 (1H, m); 4.59 (1H, dd, J=2 and J=9); 4.63-4.71 (1H, m); 5.17 (1H, t, J=6); 5.37 (1H, s); 7.19-7.28 (2H, m); 7.54-7.62 (2H, m); 8.59 (1H, s). 15.25 (1H, s).
MS: 600.5.

Example 2

(13S,16S)-16-{4-[(R)-5-((R)-2-amino-propionyloxymethyl)-2-oxo-oxazolidin-3-yl]-2-fluoro-phenoxymethyl}-1-cyclopropyl-7-fluoro-16-hydroxy-4-oxo-1,4,13,15,16,17-hexahydro-12H-11-oxa-1,14-diaza-cyclopenta[a]phenanthrene-3-carboxylic acid:

2.i. (13S,16S)-16-{4-[(R)-5-((R)-2-tert-butoxycarbonylamino-propionyloxymethyl)-2-oxo-oxazolidin-3-yl]-2-fluoro-phenoxymethyl}-1-cyclopropyl-7-fluoro-16-hydroxy-4-oxo-1,4,13,15,16,17-hexahydro-12H-11-oxa-1,14-diaza-cyclopenta[a]phenanthrene-3-carboxylic acid benzyl ester:

A solution of intermediate 1.xiii (344 mg) in DMF (3 ml) was treated for 2 h at rt with Boc-D-Ala-OH (122 mg), EDC (124 mg) and DMAP (31 mg). The DMF was evaporated and the residue purified by chromatography (DCM/MeOH 95:5). The residue was stirred in ether, the solid filtered and dried in vacuum to afford 373 mg (87% yield) of a white solid.
MS: 861.2.

2.ii. (13S,16S)-16-{4-[(R)-5-((R)-2-tert-butoxycarbonylamino-propionyloxymethyl)-2-oxo-oxazolidin-3-yl]-2-fluoro-phenoxymethyl}-1-cyclopropyl-7-fluoro-16-hydroxy-4-oxo-1,4,13,15,16,17-hexahydro-12H-11-oxa-1,14-diaza-cyclopenta[a]phenanthrene-3-carboxylic acid:

A solution of intermediate 2.i (373 mg) in MeOH/dioxane 1:1 (20 ml) was hydrogenated for 6 h over 10% Pd/C (100 mg). The catalyst was filtered off and the filtrate was evaporated under reduced pressure. The residue was stirred in MeOH and the solid filtered and dried in vacuo to afford 242 mg (72% yield) of a yellow solid.
$^1$H NMR (DMSO$_{d6}$; δ ppm): 0.99-1.12 (4H, m); 1.20 (3H, d, J=7); 1.35 (9H, s); 1.89 (1H, dd, J=4 and J=14); 2.39-2.47 (1H, m); 3.65 (1H, dd, J=5 and J=11); 3.70-3.83 (3H, m); 4.03 (1H, t, J=7); 4.08 (1H, dd, J=3 and J=11); 4.12-4.19 (3H, m); 4.21-4.27 (1H, m); 4.29-4.40 (2H, m); 4.62 (1H, dd, J=3 and J=10); 4.90-4.96 (1H, m); 5.40 (1H, s); 7.20-7.32 (3H, m); 7.58 (1H, d, J=3 and J=14); 7.60 (1H, d, J=13); 8.63 (1H, s); 15.23 (1H, s).

2.iii. (13S,16S)-16-{4-[(R)-5-((R)-2-amino-propionyloxymethyl)-2-oxo-oxazolidin-3-yl]-2-fluoro-phenoxymethyl}-1-cyclopropyl-7-fluoro-16-hydroxy-4-oxo-1,4,13,15,16,17-hexahydro-12H-11-oxa-1,14-diaza-cyclopenta[a]phenanthrene-3-carboxylic acid:

A suspension of intermediate 2.ii (156 mg) in dioxane (2 ml) was treated with 5N HCl (0.24 ml). The mixture was stirred at rt overnight. The solvents were evaporated under reduced pressure and the residue was stirred in dioxane, collected by filtration and dried in vacuo to afford 143 mg (99% yield) of a yellow solid.
$^1$H NMR (DMSO$_{d6}$; δ ppm): 0.99-1.12 (4H, m); 1.35 (3H, d, J=7); 1.89 (1H, dd, J=4 and J=14); 2.43-2.49 (1H, m); 3.63 (1H, dd, J=5 and J=11); 3.69-3.88 (3H, m); 4.08 (1H, dd, J=3 and J=11); 4.10-4.26 (5H, m); 4.38-4.52 (2H, m); 4.59 (1H, dd, J=2 and J=9); 4.91-5.01 (1H, m); 7.19-7.31 (2H, m); 7.56 (1H, dd, J=3 and J=14); 7.58 (1H, d, J=13), 8.45 (2H, s broad); 8.61 (1H, s).
MS: 671.2.

Example 3

(13S,16S)-1-ethyl-7-fluoro-16-[2-fluoro-4-((R)-5-hydroxymethyl-2-oxo-oxazolidin-3-yl)-phenoxymethyl]-16-hydroxy-4-oxo-1,4,13,15,16,17-hexahydro-12H-11-oxa-1,14-diaza-cyclopenta[a]phenanthrene-3-carboxylic acid:

3.i. 1-ethyl-6,7-difluoro-8-hydroxy-4-oxo-1,4-dihydro-quinoline-3-carboxylic acid 48% aq. HBr (35 ml) was added to a solution of 1-ethyl-6,7-difluoro-8-methoxy-4-oxo-1,4-dihydro-quinoline-3-carboxylic acid ethyl ester (9.34 g; prepared according to EP 241 206) in AcOH (30 ml). The orange solution was stirred at 110° C. for 24 h. It was poured into water (200 ml) and the grey-white precipitate was filtered. The crystals were collected and dried in vacuo to afford 6.37 g (79% yield) of a beige solid. $^1$H NMR (DMSO$_{d6}$; δ ppm): 1.43 (3H, t, J=7); 4.85 (2H, q, J=7); 7.76 (1H, dd, J=8 and J=10); 8.91 (1H, s); 12.02 (1H, broad); 14.90 (1H, broad).
MS: 269.8.

3.ii. 1-ethyl-6,7-difluoro-8-hydroxy-4-oxo-1,4-dihydro-quinoline-3-carboxylic acid ethyl ester Chlorotrimethylsilane (30 ml) was added to a suspension of intermediate 3.i (6.26 g) in DCM (55 ml) and EtOH (55 ml). The reaction mixture was stirred at 60° C. for 6 days and afterwards concentrated under reduced pressure. The residue was taken up in water (100 ml), stirred at rt and filtered. The crystals were washed with ether (4×25 ml), collected and dried in vacuo to afford 6.21 g (90% yield) of a brownish solid.

$^1$H NMR (DMSO$_{d6}$; δ ppm): 1.28 (3H, t, J=7); 1.37 (3H, t, J=7); 4.22 (2H, q, J=7); 4.66 (2H, q, J=7); 7.63 (1H, dd, J=9 and J=11); 8.55 (1H, s); 11.51 (1H, s).

MS: 298.1.

3.iii. 8-((S)-1-tert-butoxycarbonyl-4-methylene-pyrrolidin-2-ylmethoxy)-1-ethyl-6,7-difluoro-4-oxo-1,4-dihydro-quinoline-3-carboxylic acid ethyl ester This compound was obtained as a beige solid in 52% yield, starting from intermediate 3.ii (2.50 g), (2S)-2-(hydroxymethyl)-4-methylene-1-pyrrolidinecarboxylic acid tert-butyl ester (1.98 g), PPh$_3$ (3.30 g) and DIAD (2.66 ml) and using the procedure of Example 1, step 1.v.

$^1$H NMR (DMSO$_{d6}$; δ ppm): 1.29 (3H, t, J=7); 1.33 (3H, t, J=7); 1.42 (9H, s); 2.65-2.75 (1H, m); 2.85-2.99 (1H, m); 3.75-3.93 (1H, m); 3.95-4.35 (4H, m); 4.23 (2H, q, J=7); 4.43-4.55 (2H, m); 5.06 (2H, s); 7.93 (1H, dd, J=9 and J=10); 8.62 (1H, s); (contaminated by 40% PPh$_3$O).

MS: 492.8.

3.iv. 8-((S)-1-tert-butoxycarbonyl-4-methylene-pyrrolidin-2-ylmethoxy)-1-ethyl-6,7-difluoro-4-oxo-1,4-dihydro-quinoline-3-carboxylic acid This compound was obtained as a colourless solid in 59% yield, starting from intermediate 3.iii (3.0 g) and LiOH (803 mg) and using the procedure of Example 1, step 1.vi. The crude reaction product was stirred in a mixture of dioxane/EA (1:1; 80 ml) and filtered prior to acidification.

$^1$H NMR (DMSO$_{d6}$; δ ppm): 1.38 (3H, t, J=7); 1.42 (9H, s); 2.65-2.75 (1H, m); 2.87-3.02 (1H, m); 3.75-3.93 (1H, m); 3.95-4.38 (4H, m); 4.60-4.75 (2H, m); 5.06 (2H, s); 8.10 (1H, dd, J=9 and J=10); 9.00 (1H, s); 14.71 (1H, s).

MS: 465.0.

3.v. 8-((S)-1-tert-butoxycarbonyl-4-methylene-pyrrolidin-2-ylmethoxy)-1-ethyl-6,7-difluoro-4-oxo-1,4-dihydro-quinoline-3-carboxylic acid benzyl ester This compound was obtained as an orange oil in 100% yield, starting from intermediate 3.iv (1.67 g), K$_2$CO$_3$ (747 mg) and BnBr (0.47 ml) and using the procedure of Example 1, step 1.vii.

$^1$H NMR (DMSO$_{d6}$; δ ppm): 1.32 (3H, t, J=7); 1.42 (9H, s); 2.65-2.75 (1H, m); 2.82-3.00 (1H, m); 3.75-3.93 (1H, m); 3.95-4.35 (4H, m); 4.45-4.58 (2H, m); 5.06 (2H, s); 5.30 (2H, s); 7.30-7.44 (3H, m); 7.47-7.52 (2H, m); 7.96 (1H, dd, J=9 and J=10); 8.68 (1H, s).

MS: 554.9.

3.vi. 8-((2S,4S)-1-tert-butoxycarbonyl-4-hydroxy-4-hydroxymethyl-pyrrolidin-2-ylmethoxy)-1-ethyl-6,7-difluoro-4-oxo-1,4-dihydro-quinoline-3-carboxylic acid benzyl ester This compound was obtained as a beige solid in 69% yield (dr 93:7), starting from intermediate 3.v (2.27 g) and AD-mix α and using the procedure of Example 1, step 1.viii.

$^1$H NMR (DMSO$_{d6}$; δ ppm): 1.30-1.45 (12H, m); 1.85-1.98 (1H, m); 2.15-2.33 (1H, m); 3.07-3.18 (1H, m); 3.30-3.37 (2H, m); 3.43-3.50 (1H, m); 4.12-4.37 (2H, m); 4.46 (1H, t, J=9); 4.50-4.65 (2H, m); 4.82-4.90 (1H, m); 4.93 (1H, t, J=6); 5.31 (2H, s); 7.31-7.43 (3H, m); 7.48-7.52 (2H, m); 7.95 (1H, dd, J=9 and J=10); 8.69 (1H, s).

MS: 588.8.

3.vii. 1-ethyl-6,7-difluoro-8-((2S,4S)-4-hydroxy-4-hydroxymethyl-pyrrolidin-2-ylmethoxy)-4-oxo-1,4-dihydro-quinoline-3-carboxylic acid benzyl ester hydrochloride This compound was obtained as a colourless solid in 81% yield, starting from intermediate 3.vi (1.66 g) and 6M HCl in dioxane (2.3 ml) and using the procedure of Example 1, step 1.ix.

$^1$H NMR (DMSO$_{d6}$; δ ppm): 1.35 (3H, t, J=7); 1.64-1.73 (1H, m); 2.35-2.43 (1H, m); 3.08-3.51 (4H, m); 4.15 (1H, m); 4.43-4.84 (5H, m); 5.31 (2H, s); 5.44 (1H, m); 7.29-7.46 (3H, m); 7.49-7.53 (2H, m); 7.97 (1H, dd, J=9 and J=11); 8.70 (1H, s), 9.52 (1H, broad); 10.03 (1H, broad).

MS: 489.0 (M+H−HCl)$^+$.

3.viii. (13S,16S)-1-ethyl-7-fluoro-16-hydroxy-16-hydroxymethyl-4-oxo-1,4,13,15,16,17-hexahydro-12H-11-oxa-1,14-diaza-cyclopenta[a]phenanthrene-3-carboxylic acid benzyl ester This compound was obtained as a colourless solid in 64% yield, starting from intermediate 3.vii (1.20 g), NaHCO$_3$ (383 mg) and DIPEA (0.78 ml) in MeCN (25 ml) and using the procedure of Example 1, step 1.x. The crude product was purified by stirring in EtOH (10 ml).

$^1$H NMR (DMSO$_{d6}$; δ ppm): 1.32 (3H, t, J=7); 1.65 (1H, dd, J=3 and J=13); 2.34 (1H, dd, J=9 and J=13); 3.30-3.40 (1H, m); 3.42 (2H, d, J=6); 3.53-3.65 (1H, m); 3.79 (1H, t, J=10); 3.93 (1H, dd, J=4 and J=11); 4.45-4.65 (3H, m); 4.87 (1H, s); 4.97 (1H, t, J=6); 5.28 (2H, s); 7.28-7.42 (3H, m); 7.45-7.55 (3H, m); 8.49 (1H, s).

MS: 468.8.

3.ix. (13S,16S)-1-ethyl-7-fluoro-16-hydroxy-16-methanesulfonyloxymethyl-4-oxo-1,4,13,15,16,17-hexahydro-12H-11-oxa-1,14-diaza-cyclopenta[a]phenanthrene-3-carboxylic acid benzyl ester A solution of intermediate 3.viii (265 mg) in THF (8 ml) was cooled to 0° C. and treated with TEA (0.16 ml). The resulting solution was treated with methanesulfonic anhydride (118 mg) in THF (1 ml). After 30 min at rt, the reaction mixture was further treated portionwise (0.1 ml portions) with a solution of methanesulfonic anhydride (30 mg) in THF (0.3 ml) until complete disappearance of starting material. The reaction mixture was diluted with water (4 ml) and DCM (20 ml) followed by sat. aq. NaHCO$_3$ until basic pH was obtained. The solid residue obtained after work up (DCM) was taken in DCM (2 ml), stirred at rt and filtered. The crystals were collected and dried in vacuo to afford 149 mg (48% yield) of a colourless solid.

$^1$H NMR (DMSO$_{d6}$; δ ppm): 1.32 (3H, t, J=7); 1.82 (1H, dd, J=4 and J=14); 2.34 (1H, dd, J=9 and J=14); 3.24 (3H, s); 3.47 (1H, dd, J=4 and J=11); 3.59-3.66 (1H, m); 3.77 (1H, t, J=10); 3.93 (1H, dd, J=3 and J=11); 4.29 (2H, s); 4.50-4.65 (3H, m); 5.28 (2H, s); 5.51 (1H, s); 7.26-7.42 (3H, m); 7.47-7.58 (3H, m); 8.50 (1H, s).

MS: 546.7.

3.x. (13S,16S)-1-ethyl-7-fluoro-16-[2-fluoro-4-((R)-5-hydroxymethyl-2-oxo-oxazolidin-3-yl)-phenoxymethyl]-16-hydroxy-4-oxo-1,4,13,15,16,17-hexahydro-12H-11-oxa-1,14-diaza-cyclopenta[a]phenanthrene-3-carboxylic acid Intermediate 1.xii (42 mg) and $K_2CO_3$ (51 mg) were added to a suspension of intermediate 3.ix (100 mg) in MeCN/dioxane (1:1; 3 ml) at rt. The reaction mixture was heated at 80° C. for 30 h and concentrated in vacuo. The residue obtained after work up (DCM/MeOH 9:1) was purified by chromatography (DCM/MeOH 92:8) to give 75 mg (60% yield) of a beige solid.

$^1$H NMR (DMSO$_{d6}$; δ ppm): 1.30 (3H, t, J=7); 1.86 (1H, dd, J=4 and J=14); 2.44 (1H, dd, J=9 and J=14); 3.48-3.56 (2H, m); 3.61-3.71 (2H, m); 3.75-3.85 (2H, m); 3.97-4.11 (4H, m); 4.45-4.72 (4H, m); 5.18 (1H, t, J=6); 5.27 (2H, s); 5.35 (1H, s); 7.17-7.25 (2H, m); 7.26-7.43 (3H, m); 7.47-7.61 (4H, m); 8.49 (1H, s).

MS: 677.8.

3.xi. (13S,16S)-1-ethyl-7-fluoro-16-[2-fluoro-4-((R)-5-hydroxymethyl-2 oxo-oxazolidin-3-yl)-phenoxymethyl]-16-hydroxy-4-oxo-1,4,13,15,16,17 hexahydro-12H-11-oxa-1,14-diaza-cyclopenta[a]phenanthrene-3 carboxylic acid This compound was prepared in 27% yield as a yellow solid by hydrogenation of intermediate 3.x (50 mg) over 10% Pd/C (20 mg) following the procedure described in Example 1, step 1.xiv. The crude product was stirred in EA (3 ml) instead of DCM.

$^1$H NMR (DMSO$_{d6}$; δ ppm; contained traces of an unknown side product): 1.34 (3H, t, J=7); 1.86 (1H, dd, J=3 and J=13); 2.47 (1H, m, overlapped with DMSO signal); 3.48-3.83 (6H, m); 3.97-4.11 (4H, m); 4.45-4.76 (4H, m); 5.18 (1H, t, J=6); 5.37 (1H, s); 7.21 (1H, d, J=1); 7.23 (1H, t, J=9); 7.56 (1H, dd, J=3 and J=15); 7.62 (1H, d, J=13); 8.74 (1H, s); 15.37 (1H, s).

MS: 587.8.

Example 4

(13S,16R)-1-cyclopropyl-7-fluoro-16-[2-fluoro-4-((R)-5-hydroxymethyl-2-oxo-oxazolidin-3-yl)-phenoxymethyl]-4-oxo-1,4,13,15,16,17-hexahydro-12H-11-oxa-1,14-diaza-cyclopenta[a]phenanthrene-3-carboxylic acid:

4.i. (S)-2-(2,2-dimethyl-propionyloxymethyl)-4-oxo-pyrrolidine-1-carboxylic acid tert-butyl ester A colourless solution of (2S,4R)-4-hydroxy-2-hydroxymethyl-pyrrolidine-1-carboxylic acid tert-butyl ester (660 g; *J. Org. Chem.* (2003), 68, 3923-3931) in DCM (6.6 l) was cooled down to 0° C. and treated with TEA (510 ml) and, dropwise, with pivaloyl chloride (378 ml). The reaction mixture was stirred for 24 h at rt. The reaction mixture was cooled to −8° C. and treated with DIPEA (1506 ml). A solution of sulfur trioxide pyridine complex (1036 g) in DMSO (4 l) was added dropwise over 90 min. The reaction mixture was stirred at 0° C. for 1 h and was quenched with the addition of water (4 l). The aq. layer was extracted with $Et_2O$/Hex (1:1; 2×1 l) and the combined org. layers were concentrated in vacuo. The residue obtained after work up ($Et_2O$/Hex 1:1) was crystallized from Hex (2 l) affording 675 g (74%) of a colourless powder.

$^1$H NMR (DMSO$_{d6}$; δ ppm): 1.08 (9H, s); 1.42 (9H, s); 2.28-2.34 (1H, d, J=18); 2.89-3.10 (1H, m); 3.52 (1H, m); 3.82-3.89 (1H, d, J=18); 4.03-4.07 (1H, m); 4.22-4.25 (1H, m); 4.47 (1H, m).

MS: 300.5.

4.ii. (S)-2-(2,2-dimethyl-propionyloxymethyl)-4-methylene-pyrrolidine-1-carboxylic acid tert-butyl ester t-BuOK (56.2 g) was added in one portion to a white suspension of methyl triphenylphosphonium bromide (178.9 g) in THF (600 ml) at rt under nitrogen. The resulting yellow suspension was stirred at rt for 1 h. A solution of intermediate 4.i (60 g) in THF (150 ml) was added dropwise at such a rate that the temperature stayed below 25° C. The reaction mixture was stirred at rt for 1 h and quenched by the addition of water (20 ml). The reaction mixture was concentrated to a volume of 50 ml and diluted with $Et_2O$ (100 ml) and Hept (250 ml). The mixture was stirred at 0° C. for 2 h and filtered. The filtrate was washed with MeOH/water (2:1; 3×200 ml) and brine, dried over $MgSO_4$, filtered and the filtrate was concentrated in vacuo. The residue was purified by chromatography (eluents: Hept and Hept/EA (97:3 to 95:5)), affording 47.75 g (80% yield) of a yellow liquid.

$^1$H NMR (DMSO$_{d6}$; δ ppm): 1.12 (9H, s); 1.40 (9H, s); 2.32-2.43 (1H, t, J=15); 2.72-2.84 (1H, m); 3.75-3.84 (1H, m); 3.95-4.03 (4H, m); 4.99 (2H, s).

MS: 298.2.

4.iii (2S,4RS)-2-(2,2-dimethyl-propionyloxymethyl)-4-hydroxymethyl-pyrrolidine-1-carboxylic acid tert-butyl ester A 0.5M solution of 9-BBN in THF (85 ml) was added to a solution of intermediate 4.ii (4.85 g) in THF (40 ml) at 0° C. under nitrogen. The orange mixture was stirred at rt for 2 h. MeOH (20 ml) and pH 7.2 phosphate buffer (20 ml) were added dropwise at 0° C., followed by aq. $H_2O_2$ (35%; 11.7M; 7 ml). The reaction mixture was stirred at rt for 16 h. Sat. aq. $Na_2S_2O_3$ and EA were added and the mixture was vigorously stirred for 15 min. The org. layer was separated and washed with sat. aq. $NH_4Cl$, sat. aq. $NaHCO_3$, water, brine, dried over $MgSO_4$ and filtered. The filtrate was concentrated in vacuo and the residue purified by chromatography (Hex/EA 8:2 to 6:4) to give 4.60 g (89% yield) of a yellowish oil.

$^1$H NMR (DMSO$_{d6}$; δ ppm): 1.12-1.16 (9H, m); 1.39 (9H, s); 1.35-1.90 (1H, m); 2.00-2.50 (2H, m); 2.75-3.15 (1H, m); 3.22-3.50 (2H, m); 3.55-3.70 (1H, m); 3.80-4.30 (3H, m); 4.60-4.70 (1H, m).

MS: 338.1 (M+Na)$^+$.

4.iv. (2S,4RS)-4-(tert-butyl-dimethyl-silanyloxymethyl)-2-(2,2-dimethyl-propionyloxymethyl)-pyrrolidine-1-carboxylic acid tert-butyl ester Imidazole (1.49 g) was added to a colourless solution of intermediate 4.iii (4.60 g) in DCM (50 ml) at 0° C. A solution of TBDMSCl (2.75 g) in DCM (10 ml) was added and the mixture stirred at rt for 16 h. The residue obtained after work up (DCM) was purified by chromatography (Hex/EA 95:5) to give 5.52 g (88% yield) of a yellowish oil.

$^1$H NMR (DMSO$_{d6}$; δ ppm): 0.02-0.06 (6H, m); 0.84-0.88 (9H, m); 1.12-1.16 (9H, m); 1.39 (9H, s); 1.45-1.90 (1H, m); 2.00-2.50 (2H, m); 2.75-3.20 (1H, m); 3.45-3.65 (3H, m); 3.85-4.30 (3H, m).

MS: 429.9.

4.v. (2S,4R)-4-(tert-butyl-dimethyl-silanyloxymethyl)-2-hydroxymethyl-pyrrolidine-1-carboxylic acid tert-butyl ester and (2S,4S)-4-(tert-butyl-dimethyl-silanyloxymethyl)-2-hydroxymethyl-pyrrolidine-1-carboxylic acid tert-butyl ester A solution of intermediate 4.iv (5.5 g) in MeOH (50 ml) was treated at rt with NaOMe (700 mg). The reaction mixture was stirred at rt for 60 h, then quenched with sat. aq. NH$_4$Cl and concentrated in vacuo. The residue was diluted with EA, washed with sat. aq. NaHCO$_3$ and brine, dried over MgSO$_4$, filtered and concentrated in vacuo to give a yellow oil (4.70 g). After repeated chromatography (Hex/EA 85:15), the two diastereoisomers could be separated.

(R)-diastereoisomer: 0.98 g (22% yield) as a yellowish oil.
$^1$H NMR (DMSO$_{d6}$; δ ppm): 0.03 (6H, s); 0.86 (9H, s); 1.38 (9H, s); 1.52-1.68 (1H, m); 1.83-1.99 (1H, m); 2.8 (1H, quint., J=7); 2.98-3.12 (1H, m); 3.19-3.36 (2H, m); 3.39-3.58 (3H, m); 3.61-3.77 (1H, m); 4.62-4.73 (1H, broad).
MS: 346.4.

(S)-diastereoisomer: 2.68 g (61% yield) as a yellowish oil.
$^1$H NMR (DMSO$_{d6}$; δ ppm): 0.03 (6H, s); 0.86 (9H, s); 1.38 (9H, s); 1.48-1.66 (1H, m); 2.01 (1H, dt, J=8 and J=13); 2.11-2.29 (1H, m); 2.70-2.93 (1H, m); 3.34 (1H, dd, J=6 and J=10); 3.47-3.74 (5H, m); 4.62-4.73 (1H, broad).
MS: 346.4.

4.vi. 8-[(2S,4R)-1-tert-butoxycarbonyl-4-(tert-butyl-dimethyl-silanyloxymethyl)-pyrrolidin-2-yl-methoxy]-1-cyclopropyl-6,7-difluoro-4-oxo-1,4-dihydro-quinoline-3-carboxylic acid ethyl ester A solution of intermediate 4.v ((R)-diastereoisomer; 980 mg) and intermediate 1.1v (800 mg) in dry THF (10 ml) was treated with PPh$_3$ (1.02 g). The white suspension was treated dropwise over 2 h with DIAD (0.82 ml). The clear orange solution was further stirred at rt for 16 h and the reaction mixture was then concentrated in vacuo. The residue was purified by chromatography over SiO$_2$ (Hex/EA 8:2 to 6:4) to give 1.73 g (quantitative yield) of a white foam.
MS: 637.1.

4.vii. 8-[(2S,4R)-1-tert-butoxycarbonyl-4-(tert-butyl-dimethyl-silanyloxymethyl)-pyrrolidin-2-yl-methoxy]-1-cyclopropyl-6,7-difluoro-4-oxo-1,4-dihydro-quinoline-3-carboxylic acid A solution of intermediate 4.vi (1.65 g) in dioxane/water (9:1; 18 ml) was treated at rt with LiOH (342 mg) for 16 h. The reaction mixture was concentrated in vacuo. The residue was suspended in water (20 ml) and treated at 0° C. with 2M HCl (6 ml). The suspension was stirred for 2 h at 0° C. and filtered. The white solid was dried in vacuo to give 1.34 g (85% yield) of a yellow foam.
MS: 609.3.

4.viii. 8-[(2S,4R)-1-tert-butoxycarbonyl-4-(tert-butyl-dimethyl-silanyloxymethyl)-pyrrolidin-2-yl-methoxy]-1-cyclopropyl-6,7-difluoro-4-oxo-1,4-dihydro-quinoline-3-carboxylic acid benzyl ester K$_2$CO$_3$ (445 mg) and BnBr (0.28 ml) were added to a solution of intermediate 4.vii (1.31 g) in DMF (6 ml). The suspension was stirred at 60° C. for 3 h. The reaction mixture was concentrated in vacuo. The residue obtained after work up (DCM) was purified by chromatography (Hex/EA 85:15 to 75:25) to give 1.08 g (72% yield) of an orange foam.

$^1$H NMR (DMSO$_{d6}$; δ ppm): 0.04 (6H, s); 0.87 (9H, m); 0.98-1.14 (4H, m); 1.38 (9H, s); 1.77-1.95 (1H, m); 2.04-2.19 (1H, m); 3.03-3.20 (1H, m); 3.24-3.37 (1H, m, overlapped with water signal); 3.45-3.64 (2H, m); 3.92-4.23 (4H, m); 4.69-4.84 (1H, m); 5.29 (2H, s); 7.27-7.43 (3H, m); 7.44-7.53 (2H, m); 7.82-7.92 (1H, m); 8.53 (1H, s).
MS: 699.3.

4.ix. (13S,16R)-1-cyclopropyl-7-fluoro-16-hydroxymethyl-4-oxo-1,4,13,15,16,17-hexahydro-12H-11-oxa-1,14-diaza-cyclopenta[a]phenanthrene-3-carboxylic acid benzyl ester Pure intermediate 4.viii (1.08 g) was treated with TFA (4.8 ml) and stirred at rt for 1 h. Water (3 ml) was added and the reaction mixture further stirred at rt for 2 h. The reaction mixture was concentrated and dried in vacuo. The residue was taken in MeCN (10 ml), treated with NaHCO$_3$ (260 mg) and DIPEA (0.53 ml), and stirred at 80° C. for 2 h. The reaction mixture was concentrated in vacuo. The residue obtained after work up (DCM) was purified by chromatography (DCM/MeOH 98:2 to 96:4) to give a beige solid. It was taken in EA (60 ml), the slurry stirred for 1 h at rt and filtered. The crystals were collected and dried in vacuo to give 467 mg (65% yield) of a white solid.

$^1$H NMR (DMSO$_{d6}$; δ ppm): 0.89-1.11 (4H, m); 1.65-1.78 (1H, m); 1.94-2.05 (1H, m); 2.31-2.44 (1H, m); 3.34-3.50 (4H, m); 3.51-3.60 (1H, m); 3.71-3.81 (1H, m); 4.02-4.09 (1H, m); 4.53 (1H, dd, J=3 and J=10); 4.77 (1H, t, J=5); 5.26 (2H, s); 7.29-7.52 (6H, m); 8.44 (1H, s).
MS: 465.0.

4.x. (R)-3-(4-benzyloxy-3-fluoro-phenyl)-5-(tert-butyl-dimethyl-silanyloxymethyl)-oxazolidin-2-one A solution of TBDMSCl (3.77 g) in DCM (5 ml) was added dropwise to a solution of (R)-3-(4-benzyloxy-3-fluoro-phenyl)-5-hydroxymethyl-oxazolidin-2-one (6.35 g, prepared according to WO 2004/096221) and imidazole (2.04 g) in DMF (15 ml) at 0° C. The reaction mixture was stirred at rt for 16 h. The solvents were removed in vacuo and the residue dissolved in DCM, washed with 1N HCl, sat. aq. NaHCO$_3$ and worked up affording 8.41 g (97% yield) of a colourless solid.

$^1$H NMR (DMSO$_{d6}$; δ ppm): 0.04 (6H, s); 0.79 (9H, s); 3.69-3.78 (2H, m), 3.86 (1H, dd, J=3 and J=12); 4.07 (1H, t, J=9); 4.69-4.77 (1H, m); 5.15 (2H, s); 7.15-7.21 (1H, m); 7.25 (1H, t, J=9); 7.30-7.36 (1H, m); 7.37-7.50 (4H, m); 7.57 (1H, dd, J=3 and J=14).
MS: 432.4.

4.xi. (R)-5-(tert-butyl-dimethyl-silanyloxymethyl)-3-(3-fluoro-4-hydroxy-phenyl)-oxazolidin-2-one A solution of intermediate 4.x (7.22 g) in THF/MeOH (1:1; 150 ml) was hydrogenated over 10% Pd/C (150 mg) for 3 h at rt. The catalyst was filtered off and the filtrate concentrated in vacuo, affording 5.51 g (96% yield) of a colourless solid.

$^1$H NMR (DMSO$_{d6}$; δ ppm): 0.04 (6H, s); 0.80 (9H, s); 3.69-3.78 (2H, m), 3.86 (1H, dd, J=3 and J=12); 4.07 (1H, t, J=9); 4.68-4.75 (1H, m); 6.94 (1H, t, J=9); 7.04-7.10 (1H, m); 7.45 (1H, dd, J=3 and J=14); 9.65 (1H, s).
MS: 342.2.

4.xii. (13S,16R)-16-{4-[(R)-5-(tert-butyl-dimethyl-silanyloxymethyl)-2-oxo-oxazolidin-3-yl]-2-fluoro-phenoxymethyl}-1-cyclopropyl-7-fluoro-4-oxo-1,4,13,15,16,17-hexahydro-12H-11-oxa-1,14-diaza-cyclopenta[a]phenanthrene-3-carboxylic acid benzyl ester A suspension of intermediate 4.ix (150 mg) and intermediate 4.xi (105 mg) in dry dioxane (2 ml) was treated at rt under nitrogen with PPh$_3$ (121 mg). The white suspension was heated to 60° C. and treated dropwise over 2 h with DIAD (0.10 ml). The clear orange solution was further stirred at 60° C. for 2 h and the reaction mixture was then concentrated in vacuo. The residue was diluted in toluene/hexane (1:2, 10 ml) and the org. layer was extracted with MeOH/water (2:1, 3×5 ml). The aq. layers were back-extracted with toluene/hexane (1:2, 2×5 ml) and the combined org. layers were worked up (DCM). The residue was purified by chromatography (DCM/MeOH, 99:1 to 98:2) to give a yellow solid that was taken in EA (5 ml), the slurry stirred for 1 h at rt and filtered. The crystals were collected and dried in vacuo, affording 86 mg (36% yield) of a white solid.

$^1$H NMR (DMSO$_{d6}$; δ ppm): 0.04 (6H, s); 0.79 (9H, s); 0.89-1.12 (4H, m); 1.81-1.94 (1H, m); 2.07-2.18 (1H, m); 2.70-2.82 (1H, m); 3.45 (1H, t, J=10); 3.52-3.69 (2H, m); 3.69-3.79 (1H, m); 3.73 (1H, dd, J=3 and J=12); 3.82-3.92 (1H, m); 3.87 (1H, dd, J=3 and J=12); 4.02-4.14 (4H, m); 4.57 (1H, dd, J=3 and J=10); 4.69-4.79 (1H, m); 5.26 (2H, s); 7.17-7.25 (2H, m); 7.29-7.43 (3H, m); 7.44-7.52 (3H, m); 7.58 (1H, dd, J=3 and J=14); 8.46 (1H, s).
MS: 788.3.

4.xiii. (13S,16R)-1-cyclopropyl-7-fluoro-16-[2-fluoro-4-((R)-5-hydroxymethyl-2-oxo-oxazolidin-3-yl)-phenoxymethyl]-4-oxo-1,4,13,15,16,17-hexahydro-12H-11-oxa-1,14-diaza-cyclopenta[a]phenanthrene-3-carboxylic acid benzyl ester TFA (0.5 ml) was added at rt to intermediate 4.xii (80 mg) and the reaction mixture was stirred at rt for 10 min. Water (0.4 ml) was then added and further stirring at rt carried out for 2 h. The reaction mixture was concentrated to dryness and the residue was dissolved in DCM (5 ml). The solution was washed with sat. NaHCO$_3$ aq (5 ml), dried over MgSO$_4$, filtered and concentrated in vacuo. The solid residue was taken in EA (5 ml), the slurry stirred for 1 h at rt and filtered. The crystals were collected and dried in vacuo to give 36 mg (53% yield) of a pale yellow solid.

$^1$H NMR (DMSO$_{d6}$; δ ppm): 0.90-1.14 (4H, m); 1.81-1.94 (1H, m); 2.08-2.20 (1H, m); 2.70-2.83 (1H, m); 3.46 (1H, t, J=10); 3.51-3.73 (4H, m); 3.80 (1H, dd, J=6 and J=9); 3.83-3.92 (1H, m); 4.01-4.16 (4H, m); 4.57 (1H, dd, J=3 and J=10); 4.64-4.74 (1H, m); 5.20 (1H, t, J=6); 5.26 (2H, s); 7.19-7.27 (2H, m); 7.29-7.43 (3H, m); 7.44-7.52 (3H, m); 7.60 (1H, dd, J=3 and J=14); 8.47 (1H, s).
MS: 674.2.

4.xiv. (13S,16R)-1-cyclopropyl-7-fluoro-16-[2-fluoro-4-((R)-5-hydroxymethyl-2-oxo-oxazolidin-3-yl)-phenoxymethyl]-4-oxo-1,4,13,15,16,17-hexahydro-12H-11-oxa-1,14-diaza-cyclopenta[a]phenanthrene-3 carboxylic acid This compound was obtained in 43% yield as a yellow solid by hydrogenation of intermediate 4.xiii (32 mg) over 10% Pd/C (2 mg) following the procedure of Example 1, step 1.xiv. The crude product was however stirred in EA (10 ml) instead of DCM.

$^1$H NMR (DMSO$_{d6}$; δ ppm; contained 20% of des-cyclopropyl product): 0.90-1.20 (4H, m); 1.82-1.96 (1H, m); 2.08-2.24 (1H, m); 2.74-2.88 (1H, m); 3.43-3.61 (2H, m); 3.62-3.75 (3H, m); 3.80 (1H, dd, J=6 and J=9); 3.85-3.97 (1H, m); 4.05 (1H, t, J=9); 4.13 (2H, d, J=7); 4.17-4.29 (1H, s); 4.61-4.75 (2H, m); 5.20 (1H, t, J=6); 7.19-7.31 (2H, m); 7.60 (2H, dd, J=2 and J=12); 8.62 (1H, s), 15.20 (1H, s).
MS: 584.4.

Example 5

(13S,16S)-1-cyclopropyl-7-fluoro-16-[2-fluoro-4-((R)-5-hydroxymethyl-2-oxo-oxazolidin-3-yl)-phenoxymethyl]-4-oxo-1,4,13,15,16,17-hexahydro-12H-11-oxa-1,14-diaza-cyclopenta[a]phenanthrene-3-carboxylic acid:

5.i. 8-[(2S,4S)-1-tert-butoxycarbonyl-4-(tert-butyl-dimethyl-silanyloxymethyl)-pyrrolidin-2-yl-methoxy]-1-cyclopropyl-6,7-difluoro-4-oxo-1,4-dihydro-quinoline-3-carboxylic acid ethyl ester This compound was obtained as a white foam in 69% yield, starting from intermediate 4.v ((S)-diastereoisomer; 2.60 g), intermediate 1.iv (2.12 g), PPh$_3$ (2.69 g) and DIAD (2.16 ml) and following the procedure of Example 4, step 4.vi.
MS: 637.5.

5.ii. 8-[(2S,4S)-1-tert-butoxycarbonyl-4-(tert-butyl-dimethyl-silanyloxymethyl)-pyrrolidin-2-yl-methoxy]-1-cyclopropyl-6,7-difluoro-4-oxo-1,4-dihydro-quinoline-3-carboxylic acid This compound was obtained as a white powder in 94% yield, starting from intermediate 5.i (3.00 g) and LiOH (593 mg) and following the procedure of Example 4, step 4.vii.

$^1$H NMR (DMSO$_{d6}$; δ ppm): 0.04 (6H, s); 0.85 (9H, s); 1.03-1.26 (4H, m); 1.38 (9H, s); 1.82-1.97 (1H, m); 2.17-2.38 (2H, m); 2.82-3.05 (1H, m); 3.55-3.74 (3H, m); 4.01-4.38 (4H, m); 7.99-8.11 (1H, m); 8.78 (1H, s); 14.50 (1H, s).

5.iii. 8-[(2S,4S)-1-tert-butoxycarbonyl-4-(tert-butyl-dimethyl-silanyloxymethyl)-pyrrolidin-2-yl-methoxy]-1-cyclopropyl-6,7-difluoro-4-oxo-1,4-dihydro-quinoline-3-carboxylic acid benzyl ester This compound was obtained as a white foam in 84% yield, starting from intermediate 5.ii (2.68 g), K$_2$CO$_3$ (913 mg) and BnBr (0.58 ml) and following the procedure of Example 4, step 4.viii.

$^1$H NMR (DMSO$_{d6}$; δ ppm): 0.04 (6H, s); 0.85 (9H, s); 0.98-1.14 (4H, m); 1.38 (9H, s); 1.82-1.97 (1H, m); 2.14-2.41 (2H, m); 2.82-3.05 (1H, m); 3.55-3.73 (3H, m); 3.93-4.35 (4H, m); 5.31 (2H, s); 7.28-7.44 (3H, m); 7.46-7.54 (2H, m); 7.83-7.94 (1H, m); 8.54 (1H, s).
MS: 699.2.

5.iv. (13S,16S)-1-cyclopropyl-7-fluoro-16-hydroxymethyl-4-oxo-1,4,13,15,16,17-hexahydro-12H-11-oxa-1,14-diaza-cyclopenta[a]phenanthrene-3-carboxylic acid benzyl ester This compound was obtained as a white solid in 78% yield, starting from intermediate 5.iii (2.11 g), TFA (9.27 ml), DIPEA (1.04 ml) and NaHCO$_3$ (508 mg) and following the procedure of Example 4, step 4.ix.

$^1$H NMR (DMSO$_{d6}$; δ ppm): 0.84-1.14 (4H, m); 1.19-1.35 (1H, m); 2.09-2.22 (1H, m); 2.41-2.57 (1H, m, overlapped with DMSO signal); 3.13 (1H, dt, J=3 and J=10); 3.33-3.56 (3H, m); 3.56-3.70 (1H, m); 3.96-4.11 (2H, m); 4.60 (1H, dd, J=3 and J=10); 4.71 (1H, t, J=5); 5.26 (2H, s); 7.30-7.52 (6H, m); 8.45 (1H, s).

MS: 465.0.

5.v. (13S,16S)-16-{4-[(R)-5-(tert-butyl-dimethyl-silanyloxymethyl)-2-oxo-oxazolidin-3-yl]-2-fluoro-phenoxymethyl}-1-cyclopropyl-7-fluoro-4-oxo-1,4,13,15,16,17-hexahydro-12H-11-oxa-1,14-diaza-cyclopenta[a]phenanthrene-3-carboxylic acid benzyl ester:

This compound was obtained as a white solid in 38% yield, starting from intermediate 5.iv (71 mg), intermediate 4.xi (50 mg), PPh$_3$ (58 mg) and DIAD (0.044 ml), and following the procedure of Example 4, step 4.xii.

$^1$H NMR (DMSO$_{d6}$; δ ppm): 0.04 (6H, s); 0.79 (9H, s); 0.86-1.10 (4H, m); 1.34-1.48 (1H, m); 2.24-2.39 (1H, m); 2.77-2.93 (1H, m); 3.23 (1H, dt, J=3 and J=10); 3.44 (1H, t, J=10); 3.61-3.80 (3H, m); 3.85 (1H, dd, J=3 and J=12); 3.99-4.22 (5H, m); 4.64 (1H, dd, J=4 and J=11); 4.70-4.79 (1H, m); 5.26 (2H, s); 7.18-7.25 (2H, m); 7.27-7.51 (6H, m); 7.54-7.61 (1H, m); 8.46 (1H, s).

MS: 788.5.

5.vi. (13S,16S)-1-cyclopropyl-7-fluoro-16-[2-fluoro-4-((R)-5-hydroxymethyl-2-oxo-oxazolidin-3-yl)-phenoxymethyl]-4-oxo-1,4,13,15,16,17-hexahydro-12H-11-oxa-1,14-diaza-cyclopenta[a]phenanthrene-3-carboxylic acid benzyl ester This compound was obtained as a yellow solid in 76% yield, starting from intermediate 5.v (40 mg) and TFA (0.19 ml) and following the procedure described in Example 4, step 4.xiii.

$^1$H NMR (DMSO$_{d6}$; δ ppm): 0.87-1.12 (4H, m); 1.36-1.51 (1H, m); 2.25-2.39 (1H, m); 2.80-2.94 (1H, m); 3.25 (1H, dt, J=2 and J=10); 3.46 (1H, t, J=10); 3.51-3.60 (1H, m); 3.62-3.75 (2H, m); 3.79 (1H, dd, J=6 and J=9); 3.99-4.23 (5H, m); 4.60-4.74 (2H, m); 5.16-5.22 (1H, m); 5.26 (2H, s); 7.19-7.27 (2H, m); 7.27-7.53 (6H, m); 7.59 (1H, dd, J=2 and J=13); 8.46 (1H, s).

MS: 674.1.

5.vii. (13S,16S)-1-cyclopropyl-7-fluoro-16-[2-fluoro-4-((R)-5-hydroxymethyl-2-oxo-oxazolidin-3-yl)-phenoxymethyl]-4-oxo-1,4,13,15,16,17 hexahydro-12H-11-oxa-1,14-diaza-cyclopenta[a]phenanthrene-3 carboxylic acid This compound was prepared in 79% yield as a yellow solid by hydrogenation of intermediate 5.vi (20 mg) over 10% Pd/C (2 mg) following the procedure described in Example 1, step 1.xiv. The crude product was stirred in EA (5 ml) instead of DCM.

$^1$H NMR (DMSO$_{d6}$; δ ppm): 0.96-1.19 (4H, m); 1.37-1.52 (1H, m); 2.25-2.39 (1H, m); 2.81-2.96 (1H, m); 3.39 (1H, dt, J=3 and J=10); 3.50 (1H, t, J=10); 3.50-3.80 (3H, m); 3.80 (1H, dd, J=6 and J=9); 4.05 (1H, t, J=9); 4.11-4.28 (4H, m); 4.60-4.74 (1H, m); 4.72 (1H, dd, J=3 and J=10); 5.16-5.25 (1H, m); 7.19-7.30 (2H, m); 7.55-7.63 (2H, m); 8.61 (1H, s); 15.20 (1H, s).

MS: 584.4.

Example 6

(6aS,8RS)-4-cyclopropyl-11-fluoro-8-[2-fluoro-4-((R)-5-hydroxymethyl-2-oxo-oxazolidin-3-yl)-phenoxymethyl]-8-hydroxy-1-oxo-1,4,6,6a,7,8,9,10-octahydro-5-oxa-4,10a-diaza-chrysene-2-carboxylic acid

6.i. (2S,4R)-4-hydroxy-piperidine-1,2-dicarboxylic acid 1-tert-butyl ester 2-methyl ester A solution of (1S,5R)-2-[(R)-2-phenylethyl]-6-oxa-2-azabicyclo[3.2.1]octan-7-one (13.36 g; prepared according to Gillard et al., *J. Org. Chem.* (1996), 61, 2226-2231) in MeOH/dioxane (2:1; 110 ml) was treated with 1.25M HCl in MeOH (50 ml) and hydrogenated over 10% Pd(OH)$_2$/C (6 g) overnight at rt. The catalyst was filtered off and the filtrate concentrated in vacuo. The residue was suspended in DCM (200 ml), treated with TEA (9.88 ml) and stirred at rt for 15 min. The solution was treated with di-tert-butyl dicarbonate (13.41 g) and the reaction mixture stirred at rt overnight. The residue obtained after work up (DCM) was purified by chromatography (Hex/EA 1:1) to give 8.61 g (65% yield) of a colourless oil.

$^1$H NMR (DMSO$_{d6}$; δ ppm): 1.37 (9H, s, broad); 1.44-1.54 (2H, m); 1.77 (1H, dd, J=14 and J=7); 2.16 (1H, d, J=13); 3.19-3.35 (1H, m); 3.60 (4H, s); 3.87-3.88 (1H, m); 4.45-4.50 (1H, m); 4.58 (1H, d, J=2).

MS: 260.3.

6.ii. (2S,4R)-4-hydroxy-2-hydroxymethyl-piperidine-1-carboxylic acid tert-butyl ester A solution of intermediate 6.i (8.61 g) in EtOH (400 ml) was treated with NaBH$_4$ (6.28 g) at 0° C. under nitrogen. The reaction mixture was stirred for 20 h and was allowed to warm to rt during that time. The reaction was quenched with 1M aq. NaOH (35 ml) and the reaction mixture was concentrated in vacuo. The residue obtained after work up (EA) was purified by chromatography (Hex/EA 1:1) to give 6.70 g (87% yield) of a colourless oil.

$^1$H NMR (DMSO$_{d6}$; δ ppm): 1.38 (9H, s); 1.48-1.52 (2H, m); 1.60-1.66 (2H, m); 3.03-3.13 (1H, m); 3.50-3.56 (1H, m); 3.61-3.69 (2H, m); 3.87-3.90 (1H, m); 3.98-4.02 (1H, m); 4.57-4.61 (1H, t, J=6); 4.76 (1H, d, J=3).

MS: 232.4.

6.iii. (2S,4R)-2-(tert-butyl-dimethyl-silanyloxymethyl)-4-hydroxy piperidine-1-carboxylic acid tert-butyl ester A solution of intermediate 6.ii (11.75 g) in pyridine (60 ml) was treated dropwise with a solution of TBDMSCl (8.04 g) in pyridine (17.5 ml) at 0° C. The reaction mixture was stirred overnight and allowed to warm to rt during that time. The residue obtained after work up (EA) was purified by chromatography (Hex/EA 9:1 to 8:2) to give 17.94 g (100% yield) of a colourless oil.

$^1$H NMR (DMSO$_{d6}$; δ ppm): 0.00 (6H, 2s, rotamers); 0.84 (9H, s); 1.36 (9H, s); 1.45-1.67 (4H, m); 2.98-3.07 (1H, m); 3.61-3.72 (2H, m); 3.85-3.90 (2H, m); 4.00-4.09 (1H, m); 4.59 (1H, d, J=3).

6.iv. (S)-2-(tert-butyl-dimethyl-silanyloxymethyl)-4-oxo-piperidine-1-carboxylic acid tert-butyl ester A solution of intermediate 6.iii (17.94 g) in DCM (115 ml) was cooled to −8° C. and was treated with DIPEA (26 ml). A solution of sulfur trioxide pyridine complex (18.4 g) in DMSO (63 ml) was added dropwise over 15 min. The reaction mixture was stirred at 0° C. for 2 h and was quenched with the addition of H$_2$O (70 ml). The aq. layer was extracted with Et$_2$O/Hex (1:1; 3×30 ml) and the combined org. layers were concentrated in vacuo. The residue obtained after work up (Et$_2$O/Hex 1:1) was dried to give 15.69 g (88% yield) of a yellow oil.

$^1$H NMR (DMSO$_{d6}$; δ ppm): 0.00 (6H, 2s, rotamers); 0.82 (9H, s); 1.41 (9H, s); 2.21-2.42 (3H, m); 2.63 (1H, dd, J=15 and J=7); 3.42 (1H, s, broad); 3.57 (1H, dd, J=10 and J=5); 3.66 (1H, dd, J=10 and J=5); 3.91-3.99 (1H, m); 4.30 (1H, s, broad).

6.v. (S)-2-(tert-butyl-dimethyl-silanyloxymethyl)-4-methylene-piperidine-1-carboxylic acid tert-butyl ester This compound was obtained as a yellow oil in 92% yield, starting from intermediate 6.iv (15.69 g), t-BuOK (12.80 g) and methyl triphenylphosphonium bromide (40.80 g), and following the procedure of Example 4, step 4.ii. The residue was purified by chromatography (Hex/EA 9:1 to 8:2).

$^1$H NMR (DMSO$_{d6}$; δ ppm): 0.01 (6H, s); 0.84 (9H, s); 1.38 (9H, s); 1.98-2.30 (4H, m); 2.67-2.76 (1H, m); 3.45 (1H, dd, J=10 and J=7); 3.51 (1H, dd, J=10 and J=7); 3.91-3.97 (1H, m); 4.18 (1H, s, broad); 4.70 (1H, s); 4.80 (1H, s).

6.vi. ((S)-4-methylene-piperidin-2-yl)-methanol hydrochloride

A solution of intermediate 6.v (7.57 g) in 2M HCl in MeOH (60 ml) was stirred at 40° C. for 4 h. The reaction mixture was concentrated in vacuo and the residue was taken in EA (50 ml). The suspension was stirred 1 h at rt and filtered. The crystals were collected and dried in vacuo to give 2.93 g (81% yield) of a white solid.

$^1$H NMR (DMSO$_{d6}$; δ ppm): 2.27-2.48 (4H, m); 2.80-2.89 (1H, td, J=12 and J=5); 3.04-3.13 (1H, m); 3.27-3.34 (1H, m); 3.57-3.70 (2H, m); 4.90 (2H, s); 5.48-5.51 (1H, t, J=5); 9.25 (2H, s, broad).

6.vii. ((S)-1-benzyl-4-methylene-piperidin-2-yl)-methanol

A solution of intermediate 6.vi (2.93 g) in DMF (35 ml) was treated with K$_2$CO$_3$ (3.70 g) and BnBr (2.15 ml). The reaction mixture was stirred at rt for 5 h and concentrated in vacuo. The residue obtained after work up (EA) was purified by chromatography (Hex/EA 1:1) to give 3.56 g (92% yield) of a brown oil.

$^1$H NMR (DMSO$_{d6}$; δ ppm): 1.99-2.23 (4H, m); 2.31 (1H, dd, J=13 and J=4); 2.40-2.55 (1H, m); 2.65-2.73 (1H, m); 3.39-3.50 (2H, m); 3.58-3.65 (1H, m); 3.99 (1H, d, J=14); 4.46 (1H, t, J=5); 4.66 (2H, d, J=3); 7.19-7.45 (5H, m).

6.viii. 8-((S)-1-benzyl-4-methylene-piperidin-2-ylmethoxy)-1-cyclopropyl-6,7-difluoro-4-oxo-1,4-dihydro-quinoline-3-carboxylic acid ethyl ester A solution of intermediate 6.vii (1.00 g), intermediate 1.1v (1.24 g) and PPh$_3$ (1.37 g) in THF (16 ml) was treated dropwise over 2 h with DIAD (1.1 ml) at rt. The reaction mixture was further stirred at rt for 16 h and concentrated in vacuo. The residue was stirred in EA (10 ml) at 0° C. for 1 h and filtered. The filtrate was concentrated, dissolved in water/MeOH (2:1; 20 ml) and extracted with Hex/toluene (2:1; 3×10 ml). The combined org. layers were worked up and the residue was purified by chromatography (Hex/EA 9:1 to 1:1) to give 1.57 g (77% yield) of a yellow oil.

$^1$H NMR (DMSO$_{d6}$; δ ppm, contained traces of a unknown side product): 0.92-1.00 (4H, m); 1.23-1.28 (3H, m); 2.02-2.52 (5H, m); 2.55-2.83 (1H, m); 3.02-3.09 (1H, m); 3.43-3.63 (1H, m); 3.90-3.94 (1H, d, J=13); 4.00-4.08 (1H, m); 4.16-4.24 (3H, m); 4.32-4.41 (1H, m); 4.70-4.81 (2H, d, J=16); 7.13-7.30 (5H, m); 7.69-7.83 (1H, m); 8.40-8.47 (1H, s).

MS: 508.9.

6.ix. 8-((2S,4RS)-1-benzyl-4-hydroxy-4-hydroxymethyl-piperidin-2-ylmethoxy)-1-cyclopropyl-6,7-difluoro-4-oxo-1,4-dihydro-quinoline-3-carboxylic acid ethyl ester This compound was obtained as a yellow oil in 59% yield, starting from intermediate 6.viii (1.57 g) and AD-mix a (4.33 g), and following the procedure of Example 1, step 1.viii. The reaction mixture was stirred at rt for 8 days.

MS: 543.3.

6.x. (6aS,8RS)-4-cyclopropyl-11-fluoro-8-hydroxy-8-hydroxymethyl-1-oxo-1,4,6,6a,7,8,9,10-octahydro-5-oxa-4,10a-diaza-chrysene-2-carboxylic acid ethyl ester A solution of intermediate 6.ix (993 mg) in THF/MeOH (8:2; 100 ml) was hydrogenated over 10% Pd(OH)$_2$/C (80 mg) overnight at rt. Solid NaHCO$_3$ (310.0 mg) was added, the reaction mixture was stirred at rt for 30 min and concentrated in vacuo. The residue was taken in DCM/MeOH (9:1; 20 ml), the suspension stirred at rt for 30 min and filtered. The filtrate was concentrated in vacuo and the residue purified chromatography (DCM/MeOH 95:5 to 9:1) to give 412 mg (52% yield) of a yellow solid.

$^1$H NMR (DMSO$_{d6}$; δ ppm): 0.92-1.06 (4H, m); 1.24 (3H, 2t, 2 diastereoisomers, J=7); 1.35-2.01 (4H, m); 3.07-3.53 (3H, m); 3.60-4.09 (3H, m); 4.09-4.35 (4H, m); 4.38 (1H, s, broad); 4.64 (1H, 2t, J=6, 2 diastereoisomers); 7.37-7.43 (1H, 2d, 2 diastereoisomers); 8.37-8.41 (1H, 2s, 2 diastereoisomers).

MS: 433.4.

6.xi. (6aS,8RS)-4-cyclopropyl-11-fluoro-8-hydroxy-8-hydroxymethyl-1-oxo-1,4,6,6a,7,8,9,10-octahydro-5-oxa-4,10a-diaza-chrysene-2-carboxylic acid This compound was obtained as a yellow solid in 66% yield, starting from intermediate 6.x (412 mg) and lithium hydroxide monohydrate (180 mg), and following the procedure of Example 1, step 1.vi.

$^1$H NMR (DMSO$_{d6}$; δ ppm): 1.05-1.98 (8H, m); 3.14-3.44 (3H, m); 3.57-3.80 (1H, m); 3.98-4.23 (3H, m); 4.31-4.38 (1H, m); 4.42-4.43 (1H, 2s, 2 diastereomers); 4.62-4.68 (1H, 2t, J=6, 2 diastereomers); 7.52-7.58 (1H, 2d, 2 diastereomers); 8.58-8.62 (1H, 2s, 2 diastereomers); 15.00-15.10 (1H, 2s, broad, 2 diastereomers);

MS: 405.2.

6.xii. (6aS,8RS)-4-cyclopropyl-11-fluoro-8-hydroxy-8-hydroxymethyl-1-oxo-1,4,6,6a,7,8,9,10-octahydro-5-oxa-4,10a-diaza-chrysene-2-carboxylic acid benzyl ester This compound was obtained as a yellow solid in 54% yield, starting from intermediate 6.xi (245 mg), K$_2$CO$_3$ (126 mg) and BnBr (0.11 ml), and following the procedure of Example 1, step 1.vii. The crude product was not crystallized but purified by chromatography (DCM/MeOH 95:5 to 9:1).

$^1$H NMR (DMSO$_{d6}$; δ ppm): 0.9-1.97 (8H, m); 3.07-3.38 (2H, m); 3.42-3.73 (1H, m); 3.92-4.09 (2H, m); 4.17-4.34 (2H, m); 4.38 (1H, s); 4.57 (1H, s); 4.61-4.69 (1H, m); 5.24 (2H, s); 7.28-7.60 (6H, m); 8.43-8.46 (1H, 2s, 2 diastereoisomers).

MS: 495.4.

6.xiii. (6aS,8RS)-4-cyclopropyl-11-fluoro-8-hydroxy-8-methanesulfonyloxymethyl-1-oxo-1,4,6,6a,7,8,9,10-octahydro-5-oxa-4,10a-diaza-chrysene-2-carboxylic acid benzyl ester This compound was obtained as a yellow solid in 90% yield, starting from intermediate 6.xii (163 mg), TEA (0.092 ml) and methanesulfonic anhydride (70 mg), and following the procedure described in Example 3, step 3.1× The product was not crystallized from DCM but used crude in the next step.

MS: 573.0.

6.xiv. (6aS,8RS)-4-cyclopropyl-11-fluoro-8-[2-fluoro-4-((R)-5-hydroxymethyl-2-oxo-oxazolidin-3-yl)-phenoxymethyl]-8-hydroxy-1-oxo-1,4,6,6a,7,8,9,10-octahydro-5-oxa-4,10a-diaza-chrysene-2-carboxylic acid benzyl ester This compound was obtained as a yellow foam in 56% yield, starting from intermediate 6.xiii (169 mg), intermediate 1.xii (70 mg) and K$_2$CO$_3$ (61 mg), and following the procedure of Example 1, step 1.xiii. The reaction mixture was stirred at 80° C. for 22 h before concentration and work up.

MS: 704.3.

6.xv. (6aS,8RS)-4-cyclopropyl-11-fluoro-8-[2-fluoro-4-((R)-5-hydroxymethyl-2-oxo-oxazolidin-3-yl)-phenoxymethyl]-8-hydroxy-1-oxo-1,4,6,6a,7,8,9,10-octahydro-5-oxa-4,10a-diaza-chrysene-2-carboxylic acid This compound was prepared in 31% yield as a yellow solid by hydrogenation of intermediate 6.xiv (117 mg) over 10% Pd/C (20 mg) following the procedure of Example 1, step 1.xiv. The crude product was stirred in EtOH (5 ml) instead of DCM.

$^1$H NMR (DMSO$_{d6}$; δ ppm): 1.01-1.18 (4H, m); 1.61-1.77 (3H, m); 1.97-2.16 (1H, m); 3.23-3.58 (3H, m); 3.61-3.84 (3H, m); 3.85-4.06 (2H, 2s, 2 diastereoisomers); 3.98-4.07 (1H, m); 4.12-4.21 (2H, m); 4.34-4.42 (1H, m); 4.62-4.71 (1H, m); 4.96-5.01 (1H, 2s, 2 diastereoisomers); 5.13-5.20 (1H, 2t, J=6, 2 diastereoisomers); 7.15-7.26 (2H, m); 7.51-7.60 (2H, m); 8.58-8.62 (1H, 2s, 2 diastereoisomers); 15.00-15.10 (1H, 2s, broad, 2 diastereoisomers).

MS: 614.3.

Example 7

(6aR,8RS)-4-cyclopropyl-11-fluoro-8-[2-fluoro-4-((R)-5-hydroxymethyl-2-oxo-oxazolidin-3-yl)-phenoxymethyl]-8-hydroxy-1-oxo-1,4,6,6a,7,8,9,10-octahydro-5-oxa-4,10a-diaza-chrysene-2-carboxylic acid

7.i. (2R,4S)-4-hydroxy-piperidine-1,2-dicarboxylic acid 1-tert-butyl ester 2-methyl ester This compound was obtained as a yellow solid in 87% yield by hydrogenation of (1R,5S)-2-[(R)-2-phenylethyl]-6-oxa-2-azabicyclo[3.2.1]octan-7-one (31.09 g; prepared according to Gillard et al., *J. Org. Chem.* (1996), 61, 2226-2231) over 10% Pd(OH)$_2$/C (6 g) in 5M HCl in MeOH (31 ml), followed by treatment with TEA (21 ml) and di-tert-butyl dicarbonate (35.55 g), and following the procedure of Example 6, step 6.i.

$^1$H NMR (DMSO$_{d6}$; δ ppm): 1.36 (9H, s); 1.46-1.58 (2H, m); 1.76 (1H, dd, J=14 and J=7); 2.14 (1H, d, J=13); 3.12-3.38 (1H, m); 3.58 (4H, s); 3.83-3.89 (1H, m); 4.46 (1H, s, broad); 4.54 (1H, d, J=2).

7.ii. (2R,4S)-4-hydroxy-2-hydroxymethyl-piperidine-1-carboxylic acid tert-butyl ester This compound was obtained as a yellow oil in 86% yield, starting from intermediate 7.i (7.71 g) and NaBH$_4$ (5.62 g), and following the procedure described in Example 6, step 6.ii. The product was not purified by chromatography but used in the next step as the crude product after work up (EA).

$^1$H NMR (DMSO$_{d6}$; δ ppm): 1.37 (9H, s); 1.44-1.51 (2H, m); 1.55-1.68 (2H, m); 3.02-3.13 (1H, m); 3.46-3.55 (1H, m); 3.58-3.69 (2H, m); 3.83-3.91 (1H, m); 3.93-4.01 (1H, m); 4.56 (1H, t, J=5); 4.73 (1H, d, J=3).

7.iii. (2R,4S)-2-(tert-butyl-dimethyl-silanyloxymethyl)-4-hydroxy-piperidine-1-carboxylic acid tert-butyl ester This compound was obtained as a colourless oil in 84% yield, starting from intermediate 7.ii (33.23 g) and TBDMSCl (23.82 g), and following the procedure of Example 6, step 6.iii.

$^1$H NMR (DMSO$_{d6}$; δ ppm): 0.00 (6H, s); 0.83 (9H, s); 1.36 (9H, s); 1.45-1.49 (2H, m); 1.54-1.61 (2H, m); 3.00 (1H, m); 3.60-3.66 (2H, m); 3.85-3.92 (2H, m); 4.03 (1H, m); 4.60 (1H, d, J=3).

7.iv. (R)-2-(tert-butyl-dimethyl-silanyloxymethyl)-4-oxo-piperidine-1-carboxylic acid tert-butyl ester This compound was obtained as a yellow oil in 98% yield, starting from intermediate 7.iii (41.81 g), DIPEA (60 ml), sulfur trioxide pyridine complex (43 g) and DMSO (148 ml), and following the procedure of Example 6, step 6.iv.

$^1$H NMR (DMSO$_{d6}$; δ ppm): 0.01 (6H, s); 0.84 (9H, s); 1.41 (9H, s); 2.28-2.38 (3H, m); 2.64 (1H, dd, J=15 and J=7); 3.40 (1H, s, broad); 3.58 (1H, dd, J=10 and J=5); 3.66 (1H, dd, J=10 and J=5); 3.95 (1H, s, broad); 4.30 (1H, s, broad).

MS: 344.0.

7.v. (R)-2-(tert-butyl-dimethyl-silanyloxymethyl)-4-methylene-piperidine-1-carboxylic acid tert-butyl ester This compound was obtained as a yellow oil in 94% yield, starting from intermediate 7.iv (40.54 g), t-BuOK (33.10 g) and methyl triphenylphosphonium bromide (105.38 g), and following the procedure of Example 4, step 4.ii. The residue was not purified by chromatography but used crude in the next step.

$^1$H NMR (DMSO$_{d6}$; δ ppm): 0.00 (6H, s); 0.83 (9H, s); 1.37 (9H, s); 1.96-2.25 (4H, m); 2.67-2.76 (1H, m); 3.45 (1H, dd, J=10 and J=7); 3.51 (1H, dd, J=10 and J=7); 3.91-3.97 (1H, m); 4.20 (1H, s, broad); 4.70 (1H, s); 4.80 (1H, s).

MS: 342.1.

7.vi. ((R)-4-methylene-piperidin-2-yl)-methanol hydrochloride

This compound was obtained as a white solid in 100% yield, starting from intermediate 7.v (37.91 g) and 5M HCl in MeOH (120 ml), and following the procedure of Example 6, step 6.vi.

$^1$H NMR (DMSO$_{d6}$; δ ppm): 2.22-2.43 (4H, m); 2.72-2.73 (1H, m); 3.05 (1H, m); 3.25-3.29 (1H, m); 3.43-3.66 (2H, m); 4.87 (2H, s); 5.44 (1H, s, broad); 9.27 (2H, s, broad).

7.vii. ((R)-1-benzyl-4-methylene-piperidin-2-yl)-methanol

This compound was obtained as a brown oil in 46% yield, starting from intermediate 7.vi (13.38 g), K$_2$CO$_3$ (22 g) and BnBr (12.60 ml), and following the procedure of Example 6, step 6.vii.

$^1$H NMR (DMSO$_{d6}$; δ ppm): 1.95-2.23 (4H, m); 2.30 (1H, dd, J=13 and J=4); 2.40-2.55 (1H, m); 2.60-2.70 (1H, m); 3.37-3.49 (2H, m); 3.56-3.63 (1H, m); 3.97 (1H, d, J=14); 4.42 (1H, t, J=5); 4.64 (2H, d, J=3); 7.16-7.33 (5H, m).

7.viii. 8-((R)-1-benzyl-4-methylene-piperidin-2-ylmethoxy)-1-cyclopropyl-6,7-difluoro-4-oxo-1,4-dihydro-quinoline-3-carboxylic acid ethyl ester This compound was obtained as a yellow oil in 90% yield, starting from intermediate 7.vii (1.00 g), intermediate 1.iv (1.24 g), PPh$_3$ (1.38 g) and DIAD (1.1 ml), and following the procedure of Example 6, step 6.viii.

$^1$H NMR (DMSO$_{d6}$; δ ppm; contained traces of a unknown side product): 0.90-1.02 (4H, m); 1.26 (3H, t, J=7); 2.02-2.12 (1H, m); 2.15-2.52 (4H, m); 2.61-2.73 (1H, m); 3.05 (1H, m); 3.61 (1H, d, J=14); 3.92 (1H, d, J=14); 4.00-4.09 (1H, m); 4.14-4.27 (3H, m); 4.34 (1H, dd, J=9 and J=4); 4.72 (2H, d, J=15); 7.12-7.30 (5H, m); 7.80 (1H, dd, J=10 and J=9); 8.47 (1H, s)

MS: 509.0.

7.ix. 8-((R)-1-benzyl-4-hydroxy-4-hydroxymethyl-piperidin-2-ylmethoxy)-1-cyclopropyl-6,7-difluoro-4-oxo-1,4-dihydro-quinoline-3-carboxylic acid ethyl ester This compound was obtained as a beige foam in 58% yield, starting from intermediate 7.viii (1.84 g) and AD-mix α (5.06 g), and following the procedure described in Example 6, step 6.ix.

MS: 543.3.

7.x. (6aR,8RS)-4-cyclopropyl-11-fluoro-8-hydroxy-8-hydroxymethyl-1-oxo-1,4,6,6a,7,8,9,10-octahydro-5-oxa-4,10a-diaza-chrysene-2-carboxylic acid ethyl ester This compound was obtained as a yellow solid in 45% yield by hydrogenation of intermediate 7.ix (1.13 g) over 10% Pd(OH)$_2$/C (80 mg), and following the procedure of Example 6, step 6.x.

$^1$H NMR (DMSO$_{d6}$; δ ppm): 0.89-1.11 (4H, m); 1.25 (3H, 2t, 2 diastereoisomers, J=7); 1.32-2.01 (4H, m); 3.07-3.53 (3H, m); 3.61-4.09 (3H, m); 4.12-4.35 (4H, m); 4.38 (1H, s, broad); 4.64 (1H, 2t, J=6, 2 diastereoisomers); 7.37-7.42 (1H, 2d, 2 diastereoisomers); 8.37-8.40 (1H, 2s, 2 diastereoisomers).

MS: 433.4.

7.xi. (6aR,8RS)-4-cyclopropyl-11-fluoro-8-hydroxy-8-hydroxymethyl-1-oxo-1,4,6,6a,7,8,9,10-octahydro-5-oxa-4,10a-diaza-chrysene-2-carboxylic acid This compound was obtained as a yellow solid in 55% yield, starting from intermediate 7.x (410 mg) and lithium hydroxide monohydrate (120 mg), and following the procedure of Example 1, step 1.vi.

$^1$H NMR (DMSO$_{d6}$; δ ppm): 1.01-2.02 (8H, m); 3.14-3.44 (3H, m); 3.55-3.81 (1H, m); 3.96-4.23 (3H, m); 4.31-4.38 (1H, m); 4.42-4.43 (1H, 2s, 2 diastereoisomers); 4.62-4.68 (1H, 2t, J=6; 2 diastereoisomers); 7.52-7.58 (1H, 2d, 2 diastereoisomers); 8.58-8.62 (1H, 2s, 2 diastereoisomers); 15.0-15.1 (1H, s, broad).

MS: 405.1.

7.xii. (6aR,8RS)-4-cyclopropyl-11-fluoro-8-hydroxy-8-hydroxymethyl-1-oxo-1,4,6,6a,7,8,9,10-octahydro-5-oxa-4,10a-diaza-chrysene-2-carboxylic acid benzyl ester This compound was obtained as a yellow solid in 96% yield, starting from intermediate 7.xi (185 mg), K$_2$CO$_3$ (95 mg) and BnBr (0.082 ml), and following the procedure described in Example 6, step 6.xii.

$^1$H NMR (DMSO$_{d6}$; δ ppm): 0.89-1.99 (8H, m); 3.10-3.39 (2H, m); 3.42-3.73 (1H, m); 3.91-4.07 (2H, m); 4.17-4.34 (2H, m); 4.38 (1H, s); 4.57 (1H, s); 4.61-4.68 (1H, m); 5.23 (2H, s); 7.28-7.60 (6H, m); 8.43-8.46 (1H, 2s, 2 diastereoisomers).

MS: 495.2.

7.xiii. (6aR,8RS)-4-cyclopropyl-11-fluoro-8-hydroxy-8-methanesulfonyloxymethyl-1-oxo-1,4,6,6a,7,8,9,10-octahydro-5-oxa-4,10a-diaza-chrysene-2-carboxylic acid benzyl ester This compound was obtained as a brown solid in 83% yield, starting from intermediate 7.xii (217 mg), TEA (0.13 ml) and methanesulfonic anhydride (93 mg), and following the procedure of Example 3, step 3.ix The product was not crystallized from DCM but used crude in the next step.

MS: 573.2.

7.xiv. (6aR,8RS)-4-cyclopropyl-11-fluoro-8-[2-fluoro-4-((R)-5-hydroxymethyl-2-oxo-oxazolidin-3-yl)-phenoxymethyl]-8-hydroxy-1-oxo-1,4,6,6a,7,8,9,10-octahydro-5-oxa-4,10a-diaza-chrysene-2-carboxylic acid benzyl ester This compound was obtained as a yellow foam in 56% yield, starting from intermediate 7.xiii (209 mg), intermediate 1.xii (87 mg) and K$_2$CO$_3$ (76 mg), and following the procedure of Example 1, step 1.xiii. The reaction mixture was stirred at 80° C. for 22 h before concentration and work up.

MS: 704.4.

7.xv. (6aR,8RS)-4-cyclopropyl-11-fluoro-8-[2-fluoro-4-((R)-5-hydroxymethyl-2-oxo-oxazolidin-3-yl)-phenoxymethyl]-8-hydroxy-1-oxo-1,4,6,6a,7,8,9,10-octahydro-5-oxa-4,10a-diaza-chrysene-2-carboxylic acid This compound was prepared in 28% yield as a yellow solid by hydrogenation of intermediate 7.xiv (143 mg) over 10% Pd/C (25 mg) following the procedure of Example 1, step 1.xiv. The crude product was stirred in EtOH (10 ml) instead of DCM. $^1$H NMR (DMSO$_{d6}$; δ ppm): 0.99-1.24 (4H, m); 1.58-1.90 (3H, m); 1.96-2.19 (1H, m); 3.24-3.59 (3H, m); 3.60-3.82 (3H, m); 3.83-4.09 (2H, 2s, 2 diastereoisomers); 3.97-4.09 (1H, m); 4.09-4.32 (2H, m); 4.34-4.42 (1H, m); 4.60-4.73 (1H, m); 4.93-5.04 (1H, 2s, 2 diastereoisomers); 5.12-5.22 (1H, m); 7.15-7.26 (2H, m); 7.50-7.64 (2H, m); 8.55-8.66 (1H, 2s, 2 diastereoisomers); 15.0-15.1 (1H, 2s, broad, 2 diastereoisomers).

MS: 614.3.

Example 8

(13S,16S)-1-cyclopropyl-7-fluoro-16-[2-fluoro-4-((R)-5-hydroxymethyl-2-oxo-oxazolidin-3-yl)-phenoxymethyl]-4-oxo-16-phosphonooxy-1,4,13,15,16,17-hexahydro-12H-11-oxa-1,14-diaza-cyclopenta[a]phenanthrene-3-carboxylic acid 8.i. (13S,16S)-16-{4-[(R)-5-(tert-butyl-dimethyl-silanyloxymethyl)-2-oxo-oxazolidin-3-yl]-2-fluoro-phenoxymethyl}-1-cyclopropyl-7-fluoro-16-hydroxy-4-oxo-1,4,13,15,16,17-hexahydro-12H-11-oxa-1,14-diaza-cyclopenta[a]phenanthrene-3-carboxylic acid benzyl estersilyl benzyl ester:

Imidazole (75 mg) and TBDMSCl (181 mg) were added to a solution of intermediate 1.xiii. (689 mg) in DMF (6 ml). After stirring at rt for 4 h the solvent was evaporated under reduced pressure and the residue was worked up (DCM) and purified by chromatography (DCM/MeOH, 97.5:2.5), affording 445 mg (55% yield) of a white powder.

MS: 804.3.

8.ii. (13S,16S)-16-(bis-benzyloxy-phosphoryloxy)-16-{4-[(R)-5-(tert-butyl-dimethyl-silanyloxymethyl)-2-oxo-oxazolidin-3-yl]-2-fluoro-phenoxymethyl}-1-cyclopropyl-7-fluoro-4-oxo-1,4,13,15,16,17-hexahydro-12H-11-oxa-1,14-diazacyclopenta[a]phenanthrene-3-carboxylic acid benzyl ester A suspension of intermediate 8.i (455 mg) and 4,5-dicyanoimidazole (120 mg) in DCM (3 ml) was treated with dibenzyl N,N-diisopropylphosphoramidite (335 µl). The reaction mixture, after being stirred for 1 h at rt, was treated with tert-butyl hydroperoxide (163 µl) for an additional hour. After evaporation of the solvent under reduced pressure, work up (DCM) and purification by chromatography (DCM/MeOH; 95:5), 459 mg (77% yield) of a yellow powder were isolated.

MS: 1064.4.

8.iii. (13S,16S)-1-cyclopropyl-7-fluoro-16-[2-fluoro-4-((R)-5-hydroxymethyl-2-oxo-oxazolidin-3-yl)-phenoxymethyl]-4-oxo-16-phosphonooxy-1,4,13,15,16,17-hexahydro-12H-11-oxa-1,14-diaza-cyclopenta[a]phenanthrene-3-carboxylic acid benzyl ester A suspension of intermediate 8.ii (80 mg) in AcOH (1 ml) was treated with HBr (33% in AcOH; 1 ml). After stirring at rt for 4 h, the solvent was evaporated under reduced pressure and the residue was treated with water (4 ml). The resulting solid was collected by filtration and treated after drying with ether, affording 54 mg (93% yield) of a yellow powder.

MS: 680.4 and 770.3.

8.iv. (13S,16S)-1-cyclopropyl-7-fluoro-16-[2-fluoro-4-((R)-5-hydroxymethyl-2-oxo-oxazolidin-3-yl)-phenoxymethyl]-4-oxo-16 phosphonooxy-1,4,13,15,16,17-hexahydro-12H-11-oxa-1,14-diaza-cyclopenta[a]phenanthrene-3-carboxylic acid A solution of intermediate 8.iii in dioxane/MeOH/water (1:1:1; 1.5 ml) was treated with sodium acetate (9 mg) and hydrogenated over 10% Pd/C (5 mg) at rt. The catalyst was filtered off and washed with some water. The filtrate was concentrated under reduced pressure to about 1 ml and treated with 1N HCl (1 ml). After filtration, 29 mg of a solid were collected, which were taken up in 2 ml MeOH. K$_2$CO$_3$ was added and the mixture was stirred at rt for 1 h. MeOH was evaporated (at 23° C.), and the solid collected taken up in 2 ml water. 1M HCl was added until pH 0.5. The precipitate thus obtained was collected by filtration and dried under HV to yield 23 mg (58% yield) of a yellow solid.

$^1$H NMR (DMSO$_{d6}$; δ ppm): 0.99-1.15 (4H, m); 2.24-2.46 (2H, m); 2.54-2.71 (2H, m); 3.51-3.56 (3H, m); 3.72-3.83 (3H, m); 4.04 (1H, t, J=9); 4.17 (2H, d, J=4); 4.23 (1H, m); 4.45 (2H, s); 4.62-4.71 (2H, m); 5.18 (1H, m); 7.22 (2H, m); 7.58 (1H, d, J=13); 7.59 (1H, dd, J=2 and J=13.8); 8.61 (1H, s).

MS: 680.3.

Example 9

(13S,16S)-7-fluoro-16-[2-fluoro-4-((R)-5-hydroxymethyl-2-oxo-oxazolidin-3-yl)-phenoxymethyl]-16-hydroxy-4-oxo-1,4,13,15,16,17-hexahydro-12H-11-oxa-1,14-diaza-cyclopenta[a]phenanthrene-3-carboxylic acid A solution of intermediate 1.xiv (200 mg) in DMA (10 ml) was hydrogenated over 10% Pd/C (60 mg) for 16 h at 80° C. The reaction mixture was concentrated in vacuo, taken in DCM/MeOH 90:10 (25 ml) and stirred at rt for 30 min. The catalyst was filtered off and the filtrate concentrated in vacuo. The residue was taken EA (5 ml), stirred at rt for 16 h and filtered. The crystals were collected and dried in vacuo to give 136 mg (73% yield) of a beige solid.

$^1$H NMR (DMSO$_{d6}$; δ ppm): 1.80-1.92 (1H, m); 2.39-2.54 (1H, m); 3.48-3.82 (5H, m); 3.89 (1H, t, J=10); 3.97-4.09 (1H, m); 4.04 (1H, t, J=9); 4.11 (2H, s); 4.62-4.72 (2H, m); 5.17 (1H, t, J=6); 5.38 (1H, s); 7.18-7.29 (2H, m); 7.50 (1H, d, J=13); 7.58 (1H, dd, J=2 and J=14); 8.44 (1H, s); 12.75 (1H, broad); 15.45 (1H, s).

MS: 560.4.

Example 10

(13S,16S)-1-cyclopropyl-7-fluoro-16-[2-fluoro-4-((R)-2-oxo-5-phosphonooxymethyl-oxazolidin-3-yl)-phenoxymethyl]-4-oxo-16-phosphonooxy-1,4,13,15,16,17-hexahydro-12H-11-oxa-1,14-diaza-cyclopenta[a]phenanthrene-3-carboxylic acid and (13S,16S)-1-cyclopropyl-7-fluoro-16-[2-fluoro-4-((R)-2-oxo-5-phosphonooxymethyl-oxazolidin-3-yl)-phenoxymethyl]-4-oxo-16-hydroxy-1,4,13,15,16,17-hexahydro-12H-11-oxa-1,14-diaza-cyclopenta[a]phenanthrene-3-carboxylic acid 10.i. (13S,16S)-16-(bis-benzyloxy-phosphoryloxy)-16-{4-[(R)-5-(bis-benzyloxy-phosphoryloxymethyl)-2-oxo-oxazolidin-3-yl]-2-fluoro-phenoxymethyl}-1-cyclopropyl-7-fluoro-4-oxo-1,4,13,15,16,17-hexahydro-12H-11-oxa-1,14-diaza-cyclopenta[a]phenanthrene-3-carboxylic acid (10.i.a) and (13S,16S)-16-{4-[(R)-5-(bis-benzyloxy-phosphoryloxymethyl)-2-oxo-oxazolidin-3-yl]-2-fluoro-phenoxymethyl}-1-cyclopropyl-7-fluoro-16-hydroxy-4-oxo-1,4,13,15,16,17-hexahydro-12H-11-oxa-1,14-diaza-cyclopenta[a]phenanthrene-3-carboxylic acid (10.i.b)

A suspension of the compound of Example 1 (695 mg) in DCM (50 ml) and 4,5-dicyano-imidazole (220 mg) was treated dropwise with dibenzyl N,N-diisopropylphosphoramidite (0.56 ml). The reaction was stirred for 4 h at rt then treated with a solution of tert-butyl hydroperoxide in water (0.177 ml) and further stirred for 2 h. The reaction mixture was washed with water and brine, dried over $MgSO_4$, filtered and the filtrate purified by chromatography (DCM/MeOH 95:5) leaving 822 mg (83% yield) of a pale yellow oil containing mainly the diphosphoryloxy derivative 10.i.a and traces of the monophosphoryloxy derivative 10.i.b. This mixture was used in the next step without further purification.
Compound 10.i.a:
$^1$H NMR ($DMSO_{d6}$; δ ppm): 0.99-1.20 (4H, m); 2.30 (1H, dd, J=5 and J=14); 2.60-2.77 (1H, m); 3.58 (1H, t, J=10); 3.70-3.82 (2H, m); 4.06-4.32 (6H, m); 4.45-4.62 (3H, m); 4.78-5.09 (9H, m); 7.04-7.42 (22H, m); 7.49-7.61 (2H, m); 8.58 (1H, s)
MS: 1120.4.
Compound 10.i.b:
MS: 860.1.

10.ii. (13S,16S)-1-cyclopropyl-7-fluoro-16-[2-fluoro-4-((R)-2-oxo-5-phosphonooxymethyl-oxazolidin-3-yl)-phenoxymethyl]-4-oxo-16-phosphonooxy-1,4,13,15,16,17-hexahydro-12H-11-oxa-1,14-diaza-cyclopenta[a]phenanthrene-3-carboxylic acid (10.11.a) and (13S,16S)-1-cyclopropyl-7-fluoro-16-[2-fluoro-4-((R)-2-oxo-5-phosphonooxymethyl-oxazolidin-3-yl)-phenoxymethyl]-4-oxo-16-hydroxy-1,4,13,15,16,17-hexahydro-12H-11-oxa-1,14-diaza-cyclopenta[a]phenanthrene-3 carboxylic acid (10.11.b)

A solution of intermediates 10.i.a and 10.i.b (243 mg) in dioxane/MeOH/water (3:6:2; 11 ml), was hydrogenated at 8° C. for 8 h over $Pd(OH)_2$ (10 mg) in presence of sodium acetate (46.4 mg). The catalyst was filtered off and the filtrate evaporated. The residue was taken in water (7 ml) and treated dropwise with 1N HCl until precipitation (pH 1). The resulting crystals were collected by filtration, washed with water and dried affording 100 mg (61% yield) of orange powder containing the diphosphoryloxy derivative 10.ii.a and traces of the monophosphoryloxy derivative 10.ii.b.
Compound 10.ii.a:
$^1$H NMR ($DMSO_{d6}$; δ ppm): 0.97-1.23 (4H, m); 2.20-2.45 (1H, m); 2.50-2.70 (1H, m); 3.70-3.84 (3H, m); 3.92-4.24 (6H, m); 4.44 (2H, s); 4.55-4.66 (1H, m); 4.79-4.92 (1H, m); 7.18-7.26 (2H, m); 7.57 (2H, d, J=13); 8.60 (1H, s).
MS: 740.4.
Compound 10.ii.b:
MS: 680.4.

Example 11

(13S,16S)-16-{4-[(R)-5-((S)-2-amino-propionyloxymethyl)-2-oxo-oxazolidin-3-yl]-2-fluoro-phenoxymethyl}-1-cyclopropyl-7-fluoro-16-hydroxy-4-oxo-1,4,13,15,16,17-hexahydro-12H-11-oxa-1,14-diaza-cyclopenta[a]phenanthrene-3-carboxylic acid hydrochloride 11.i. (13S,16S)-16-{4-[(R)-5-((S)-2-tert-butoxycarbonylamino-propionyloxymethyl)-2-oxo-oxazolidin-3-yl]-2-fluoro-phenoxymethyl}-1-cyclopropyl-7-fluoro-16-hydroxy-4-oxo-1,4,13,15,16,17-hexahydro-12H-11-oxa-1,14-diaza-cyclopenta[a]phenanthrene-3-carboxylic acid benzyl ester:

This compound was obtained as a white solid (1100 mg; 86% yield), starting from intermediate 1.xiii (1034 mg), Boc-L-Ala-OH (369 mg), EDC (373 mg) and DMAP (91 mg) and following the procedure of Example 2, step 2.i.
MS: 861.1.

11.ii. (13S,16S)-16-{4-[(R)-5-((S)-2-tert-butoxycarbonylamino-propionyloxymethyl)-2-oxo-oxazolidin-3-yl]-2-fluoro-phenoxymethyl}-1-cyclopropyl-7-fluoro-16-hydroxy-4-oxo-1,4,13,15,16,17-hexahydro-12H-11-oxa-1,14-diaza-cyclopenta[a]phenanthrene-3-carboxylic acid This compound was obtained as a yellow solid (116 mg; 65% yield), starting from intermediate 11.i (200 mg) and following the procedure of Example 2, step 2.ii. $^1$H NMR ($DMSO_{d6}$; δ ppm): 0.99-1.12 (4H, m); 1.19 (3H, d, J=7); 1.32 (9H, s); 1.87 (1H, dd, J=4 and J=14), 2.40-2.45 (1H, m), 3.62 (1H, dd, J=6 and J=12); 3.69-3.85 (3H, m); 3.95-4.25 (7H, m), 4.44 (1H, dd, J=3 and J=13), 4.58 (1H, dd, J=2 and J=9); 4.86-4.96 (1H, m); 5.37 (1H, s); 7.19-7.30 (3H, m); 7.56 (1H, dd, J=3 and J=14); 7.58 (1H, d, J=13); 8.60 (1H, s).
MS: 771.3.

11.iii. (13S,16S)-16-{4-[(R)-5-((S)-2-amino-propionyloxymethyl)-2-oxo-oxazolidin-3-yl]-2-fluoro-phenoxymethyl}-1-cyclopropyl-7-fluoro-16-hydroxy-4-oxo-1,4,13,15,16,17-hexahydro-12H-11-oxa-1,14-diaza-cyclopenta[a]phenanthrene-3-carboxylic acid hydrochloride This compound was obtained as a yellow solid (96 mg; 95% yield) by acidic treatment (5N HCl) of intermediate 11.ii (116 mg) following the procedure of Example 2, step 2.iii.
$^1$H NMR ($DMSO_{d6}$; δ ppm): 0.99-1.12 (m, 4H); 1.36 (3H, d, J=7); 1.87 (1H, dd, J=4 and J=14); 2.42 (1H, m); 3.62 (1H, dd, J=6 and J=12); 3.69-3.91 (3H, m); 4.05 (1H, dd, J=3 and J=11); 4.10-4.25 (5H, m), 4.31-4.38 (1H, m); 4.52-4.61 (2H, m); 4.91-5.00 (1H, m); 7.19-7.30 (2H, m); 7.56 (1H, dd, J=3 and J=14); 7.58 (1H, d, J=13); 8.44 (2H, s broad); 8.60 (1H, s).

MS: 671.2.

Example 12

(13S,16S)-1-cyclopropyl-7-fluoro-16-{2-fluoro-4-[(R)-2-oxo-5-(piperidine-4-carbonyloxymethyl)-oxazolidin-3-yl]-phenoxymethyl}-16-hydroxy-4-oxo-1,4,13,15,16,17-hexahydro-12H-11-oxa-1,14-diaza-cyclopenta[a]phenanthrene-3-carboxylic acid:

12.i. (13S,16S)-piperidine-1,4-dicarboxylic acid 1-benzyl ester 4-{(R)-3-[3-fluoro-4-(7-fluoro-16-hydroxy-3-benzyloxycarbonyl-1-cyclopropylyl-4-oxo-1,4,13,15,16,17-hexahydro-12H-11-oxa-1,14-diaza-cyclopenta[a]phenanthren-16-ylmethoxy)-phenyl]-2-oxo-oxazolidin-5-ylmethyl}ester A solution of the intermediate 1.xiii (689 mg) in DMF (10 ml) was treated dropwise with N-carbobenzyloxy-4-piperidinecarboxylic acid (394 mg), EDC (249 mg) and DMAP (61 mg). The reaction was stirred at rt overnight. The DMF was removed under reduced pressure and the residue was purified by chromatography over $SiO_2$ (DCM/MeOH 95:5), leaving a colourless solid (264 mg, 28% yield).

MS (ESI$^+$): 985.5 (M+H)$^+$.

12.ii. (13S,16S)-1-cyclopropyl-7-fluoro-16-{2-fluoro-4-[(R)-2-oxo-5-(piperidine-4-carbonyloxymethyl)-oxazolidin-3-yl]-phenoxymethyl}-16-hydroxy-4-oxo-1,4,13,15,16,17-hexahydro-12H-11-oxa-1,14-diaza-cyclopenta[a]phenanthrene-3-carboxylic acid A solution of intermediate 12.i (264 mg) in DMF (15 mL) was hydrogenated over 10% Pd/C (100 mg) for 3 h. The catalyst was removed by filtration and the filtrate was treated with a palladium scavenger (Deloxan THP®). The mixture was filtered and the filtrate was evaporated under reduced pressure. The residue was crystallized from DMF/MeOH, affording after filtration and drying an off white solid (145 mg, 72% yield).

$^1$H NMR (DMSO$_{d6}$; δ ppm): 0.98-1.15 (4H, m); 1.29-1.44 (2H, m); 1.61-1.71 (2H, m); 1.82-1.90 (1H, m); 2.33-2.47 (4H, m); 2.78-2.85 (2H, m); 3.63 (1H, dd, J=5 and J=10); 3.70-3.81 (3H, m); 4.05 (1H, dd, J=3 and J=11); 4.1-4.36 (6H, m); 3.59 (1H, dd, J=2 and J=9); 4.87-4.96 (1H, m); 5.37 (1H, m); 7.18-7.29 (2H, m); 7.55 (1H, dd, J=2 and J=13); 7.58 (1H, d, J=13); 8.6 (1H, s).

MS (ESI$^+$): 985.5 (M+H)$^+$.

Example 13

(13S,16S)-1-cyclopropyl-7-fluoro-16-[2-fluoro-4-((R)-2-oxo-5-phosphonooxymethyl-oxazolidin-3-yl)-phenoxymethyl]-16-hydroxy-4-oxo-1,4,13,15,16,17-hexahydro-12H-11-oxa-1,14-diaza-cyclopenta[a]phenanthrene-3-carboxylic acid 13.i. (13S,16S)-16-{4-[(R)5-(bis-benzyloxy-phosphoryloxymethyl)-2-oxo-oxazolidin-3-yl]-2-fluoro-phenoxymethyl}-1-cyclopropyl-7-fluoro-16-hydroxy-4-oxo-1,4,13,15,16,17-hexahydro-12H-11-oxa-1,14-diaza-cyclopenta[a]phenanthrene-3-carboxylic acid benzyl ester 4,5-dicyanoimidazole (274 mg) was added to a milky suspension of intermediate 1.xiii (1000 mg) in dry DCM (10 mL). The clear yellow reaction mixture was cooled to 0° C. and treated dropwise over 1 h with dibenzyl N,N-diisopropylphosphoramidite (0.548 mL). The yellow reaction mixture was further stirred at 0° C. for 1 h and diluted with water (10 mL). The organic layer was separated, washed with water (10 mL) and treated at 0° C. with a 70% solution of tert-butyl hydroperoxide in water (0.25 mL). The reaction was stirred at 0° C. for 1 h and further stirred overnight at rt. The reaction mixture was washed with water, sat. NaHCO$_3$ solution, dried over MgSO$_4$, filtered and the filtrate evaporated under reduced pressure. The residue was purified by chromatography over SiO$_2$ using a DCM/MeOH (95:5) mixture as eluent. The fractions with a RF of 0.4 (DCM/MeOH 9:1) were collected and evaporated. The residue was stirred in ether (100 ml) affording 0.650 mg (47% yield) of yellow material.

$^1$H NMR (DMSO$_{d6}$; δ ppm): 0.89-1.10 (4H, m); 1.89-1.90 (1H, m); 2.38-2.44 (1H, m); 3.52 (1H, dd, J=5 and J=10); 3.60-3.70 (1H, m); 3.71-3.82 (2H, m); 3.98-4.31 (7H, m); 4.52 (1H, dd, J=3 and J=10); 4.85-4.95 (1H, m); 5.00 (4H, t, J=7.5); 5.24 (2H, s); 5.35 (2H, s); 7.15-7.57 (8H, m); 8.45 (1H, s).

MS (ESI$^+$): 950.5 (M+H)$^+$.

13.ii. (13S,16S)-1-cyclopropyl-7-fluoro-16-[2-fluoro-4-((R)-2-oxo-5-phosphonooxymethyl-oxazolidin-3-yl)-phenoxymethyl]-16-hydroxy-4-oxo-1,4,13,15,16,17-hexahydro-12H-11-oxa-1,14-diaza-cyclopenta[a]phenanthrene-3-carboxylic acid:

A solution of 0.65 g of intermediate 13.i in DMF (15 ml) was hydrogenated for 2 h over 10% Pd/C (0.5 g). The DMF was evaporated, the residue was dissolved in DMF (2 ml) and diluted with MeOH (5 ml). The resulting solid was filtered and washed with MeOH and ether affording a yellow solid (372 mg, 81% yield).

$^1$H NMR (DMSO$_{d6}$; δ ppm): 0.98-1.14 (4H, m); 1.83-1.90 (1H, dd, J=3 and J=13); 3.62 (1H, dd, J=6 and J=11); 3.68-3.84 (4H, m); 3.94-4.14 (6H, dd, J=6 and J=11); 4.17-4.27 (1H, m); 4.58 (1H, dd, J=2 and J=9); 4.81-4.89 (1H, m); 7.20-7.25 (2H, m); 7.54-760 (2H, dd, J=2 and J=12.5); 8.59 (1H, s).

MS (ESI$^+$): 680.4 (M+H)$^+$.

Biological Assays

In Vitro Assay

Experimental Method:

These assays have been performed following the description given in "Methods for dilution Antimicrobial Susceptibility Tests for Bacteria that Grow Aerobically, 4th ed.; Approved standard: NCCLS Document M7-A4; National Committee for Clinical Laboratory Standards Villanova, Pa., USA, 1997". Minimal inhibitory concentrations (MICs; mg/l) were determined in cation-adjusted Mueller-Hinton Broth (BBL) by a microdilution method following NCCLS guidelines (National Committee for Clinical Laboratory Standards. Methods for Dilution Antimicrobial Susceptibility). The pH of the test medium was 7.2-7.3.

Results:

All the above Examples were tested against several Gram positive and Gram negative bacteria. Typical antibacterial spectra are given in the table below (MIC in mg/l).

| Example No. | S. aureus A798 | S. Pneumoniae 49619 | M. catarrhalis A894 |
|---|---|---|---|
| 3 | 0.5 | 0.25 | 0.125 |
| 6 | 0.5 | 0.25 | 0.5 |

Besides, the following results have been obtained for the Example compounds corresponding to formula $I_D$ on *S. Pneumoniae* 49619 (MIC in mg/l):

| Example No. | S. Pneumoniae 49619 |
|---|---|
| 1 | ≦0.063 |
| 2 | 0.125 |
| 3 | 0.25 |
| 4 | 0.25 |
| 5 | 0.25 |
| 6 | 0.25 |
| 7 | 0.25 |
| 9 | 0.25 |

Moreover, in physiological environment (comprising phosphatases and esterases), the compounds of formula $I_{PDG}$ are rapidly converted into the corresponding compounds of formula $I_D$. Indeed:

the compound of Example 8, in the presence of human alkaline phosphatase, has a MIC of 0.25 mg/l against *S. aureus* A798, whereas the same compound has a MIC of 4 mg/l against *S. aureus* A798 when the phosphatase is absent; and the compound of Example 11, even in the absence of human serum, has a MIC≦0.063 mg/l against *S. Pneumoniae* 49619.

the compound of Example 12, in the presence of human serum, has a MIC of 2 mg/l against *S. aureus* A798 whereas the same compound has a MIC of 8 mg/l against *S. aureus* A798 when the human serum is absent.

The invention claimed is:

1. A compound of formula I

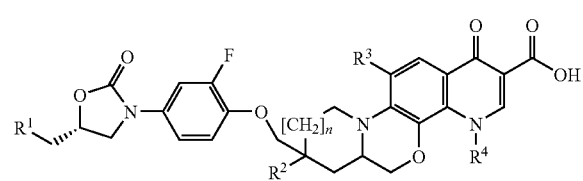

wherein
$R^1$ is OH, OPO$_3$H$_2$ or OCOR$^5$;
$R^2$ is H, OH or OPO$_3$H$_2$;
$R^3$ is H or halogen;
$R^4$ is H, (C$_1$-C$_3$)alkyl or cycloalkyl;
$R^5$ is piperidin-4-yl or $R^5$ is the residue of a naturally occurring amino acid, of the enantiomer of a naturally occurring amino acid or of dimethylaminoglycine;
n is 0 or 1;
or a salt of the compound.

2. The compound of claim 1, of formula $I_P$:

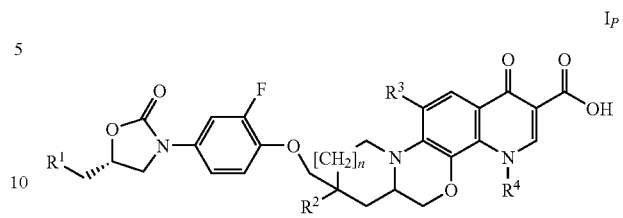

wherein
$R^1$ is OH, OPO$_3$H$_2$ or OCOR$^5$;
$R^2$ is H, OH or OPO$_3$H$_2$;
$R^3$ is H or halogen;
$R^4$ is H, (C$_1$-C$_3$)alkyl or cycloalkyl;
$R^5$ is the residue of a naturally occurring amino acid, of the enantiomer of a naturally occurring amino acid or of dimethylaminoglycine;
n is 0 or 1;
or a salt of the compound.

3. The compound according to claim 1, wherein n is 0.
4. The compound according to claim 1, wherein n is 1.
5. The compound according to claim 1, wherein $R^2$ is H or OH.
6. The compound according to claim 1, wherein $R^3$ is fluorine.
7. The compound according to claim 1, wherein $R^4$ is cycloalkyl.
8. The compound according to claim 1, wherein the compound is:

(13S,16S)-1-cyclopropyl-7-fluoro-16-[2-fluoro-4-((R)-5-hydroxymethyl-2-oxo-oxazolidin-3-yl)-phenoxymethyl]-16-hydroxy-4-oxo-1,4,13,15,16,17-hexahydro-12H-11-oxa-1,14-diaza-cyclopenta[a]phenanthrene-3-carboxylic acid;

(13S,16S)-16-{4-[(R)-5-((R)-2-amino-propionyloxymethyl)-2-oxo-oxazolidin-3-yl]-2-fluoro-phenoxymethyl}-1-cyclopropyl-7-fluoro-16-hydroxy-4-oxo-1,4,13,15,16,17-hexahydro-12H-11-oxa-1,14-diaza-cyclopenta[a]phenanthrene-3-carboxylic acid;

(13S,16S)-1-ethyl-7-fluoro-16-[2-fluoro-4-((R)-5-hydroxymethyl-2-oxo-oxazolidin-3-yl)-phenoxymethyl]-16-hydroxy-4-oxo-1,4,13,15,16,17-hexahydro-12H-11-oxa-1,14-diaza-cyclopenta[a]phenanthrene-3-carboxylic acid;

(13S,16R)-1-cyclopropyl-7-fluoro-16-[2-fluoro-4-((R)-5-hydroxymethyl-2-oxo-oxazolidin-3-yl)-phenoxymethyl]-4-oxo-1,4,13,15,16,17-hexahydro-12H-11-oxa-1,14-diaza-cyclopenta[a]phenanthrene-3-carboxylic acid;

(13S,16S)-1-cyclopropyl-7-fluoro-16-[2-fluoro-4-((R)-5-hydroxymethyl-2-oxo-oxazolidin-3-yl)-phenoxymethyl]-4-oxo-1,4,13,15,16,17-hexahydro-12H-11-oxa-1,14-diaza-cyclopenta[a]phenanthrene-3-carboxylic acid;

(6aS,8R)-4-cyclopropyl-11-fluoro-8-[2-fluoro-4-((R)-5-hydroxymethyl-2-oxo-oxazolidin-3-yl)-phenoxymethyl]-8-hydroxy-1-oxo-1,4,6,6a,7,8,9,10-octahydro-5-oxa-4,10a-diaza-chrysene-2-carboxylic acid;

(6aS,8S)-4-cyclopropyl-11-fluoro-8-[2-fluoro-4-((R)-5-hydroxymethyl-2-oxo-oxazolidin-3-yl)-phenoxymethyl]-8-hydroxy-1-oxo-1,4,6,6a,7,8,9,10-octahydro-5-oxa-4,10a-diaza-chrysene-2-carboxylic acid;

(6aR,8R)-4-cyclopropyl-11-fluoro-8-[2-fluoro-4-((R)-5-hydroxymethyl-2-oxo-oxazolidin-3-yl)-phenoxymethyl]-8-hydroxy-1-oxo-1,4,6,6a,7,8,9,10-octahydro-5-oxa-4,10a-diaza-chrysene-2-carboxylic acid;

(6aR,8S)-4-cyclopropyl-11-fluoro-8-[2-fluoro-4-((R)-5-hydroxymethyl-2-oxo-oxazolidin-3-yl)-phenoxymethyl]-8-hydroxy-1-oxo-1,4,6,6a,7,8,9,10-octahydro-5-oxa-4,10a-diaza-chrysene-2-carboxylic acid;

(13S,16S)-1-cyclopropyl-7-fluoro-16-[2-fluoro-4-((R)-5-hydroxymethyl-2-oxo-oxazolidin-3-yl)-phenoxymethyl]-4-oxo-16-phosphonooxy-1,4,13,15,16,17-hexahydro-12H-11-oxa-1,14-diaza-cyclopenta[a]phenanthrene-3-carboxylic acid;

(13S,16S)-7-fluoro-16-[2-fluoro-4-((R)-5-hydroxymethyl-2-oxo-oxazolidin-3-yl)-phenoxymethyl]-16-hydroxy-4-oxo-1,4,13,15,16,17-hexahydro-12H-11-oxa-1,14-diaza-cyclopenta[a]phenanthrene-3-carboxylic acid;

(13S,16S)-1-cyclopropyl-7-fluoro-16-[2-fluoro-4-((R)-2-oxo-5-phosphonooxymethyl-oxazolidin-3-yl)-phenoxymethyl]-4-oxo-16-phosphonooxy-1,4,13,15,16,17-hexahydro-12H-11-oxa-1,14-diaza-cyclopenta[a]phenanthrene-3-carboxylic acid;

(13S,16S)-1-cyclopropyl-7-fluoro-16-[2-fluoro-4-((R)-2-oxo-5-phosphonooxymethyl-oxazolidin-3-yl)-phenoxymethyl]-4-oxo-16-hydroxy-1,4,13,15,16,17-hexahydro-12H-11-oxa-1,14-diaza-cyclopenta[a]phenanthrene-3-carboxylic acid;

(13S,16S)-16-{4-[(R)-5-((S)-2-amino-propionyloxymethyl)-2-oxo-oxazolidin-3-yl]-2-fluoro-phenoxymethyl}-1-cyclopropyl-7-fluoro-16-hydroxy-4-oxo-1,4,13,15,16,17-hexahydro-12H-11-oxa-1,14-diaza-cyclopenta[a]phenanthrene-3-carboxylic acid;

(13S,16S)-1-cyclopropyl-7-fluoro-16-{2-fluoro-4-[(R)-2-oxo-5-(piperidine-4-carbonyloxymethyl)-oxazolidin-3-yl]phenoxymethyl}-16-hydroxy-4-oxo-1,4,13,15,16,17-hexahydro-12H-11-oxa-1,14-diaza-cyclopenta[a]phenanthrene-3-carboxylic acid; or (13S,16S)-1-cyclopropyl-7-fluoro-16-[2-fluoro-4-((R)-2-oxo-5-phosphonooxymethyl-oxazolidin-3-yl)-phenoxymethyl]-16-hydroxy-4-oxo-1,4,13,15,16,17-hexahydro-12H-11-oxa-1,14-diaza-cyclopenta[a]phenanthrene-3-carboxylic acid;

or a salt thereof.

9. A pharmaceutical composition comprising as active principle, the compound of claim 1 or a pharmaceutically acceptable salt of the compound, and at least one therapeutically inert excipient.

10. A method for treatment of bacterial infections comprising administering the compound of claim 1 or a pharmaceutically acceptable salt of the compound to a patient in need thereof.

11. The compound according to claim 2, wherein n is 0.

12. The compound according to claim 2, wherein n is 1.

13. The compound according to claim 2, wherein $R^2$ is H or OH.

14. The compound according to claim 2, wherein $R^3$ is fluorine.

15. The compound according to claim 2, wherein $R^4$ is cycloalkyl.

16. A pharmaceutical composition comprising the compound of claim 2 or a pharmaceutically acceptable salt of the compound, and at least one therapeutically inert excipient.

17. A method for treatment of bacterial infections comprising administering the compound of claim 2 or a pharmaceutically acceptable salt of the compound to a patient in need thereof.

18. The compound according to claim 2, wherein $R^1$ is $OCOR^5$, and $R^5$ is the residue of a naturally occurring amino acid, of the enantiomer of a naturally occurring amino acid or of dimethylaminoglycine.

* * * * *